US007425209B2

(12) United States Patent
Fowles et al.

(10) Patent No.: US 7,425,209 B2

(45) **Date of Patent: *Sep. 16, 2008**

(54) SLIDING RECONSTITUTION DEVICE FOR A DILUENT CONTAINER

(75) Inventors: Thomas A. Fowles, McHenry, IL (US); Robert J. Weinberg, Richmond, IL (US)

(73) Assignee: Baxter International Inc., Deerfield, IL (US)

( * ) Notice: Subject to any disclaimer, the term of this patent is extended or adjusted under 35 U.S.C. 154(b) by 713 days.

This patent is subject to a terminal disclaimer.

(21) Appl. No.: 10/744,953

(22) Filed: Dec. 23, 2003

(65) Prior Publication Data

US 2004/0199139 A1 Oct. 7, 2004

Related U.S. Application Data

(63) Continuation-in-part of application No. 10/106,716, filed on Mar. 26, 2002, now Pat. No. 7,074,216, which is a continuation-in-part of application No. 09/561,666, filed on May 2, 2000, now Pat. No. 6,582,415, which is a continuation of application No. 09/153,816, filed on Sep. 15, 1998, now Pat. No. 6,113,583.

(51) Int. Cl.
*A61B 19/00* (2006.01)

(52) U.S. Cl. ........................ 604/415; 604/411; 604/403

(58) Field of Classification Search .......... 604/411–416
See application file for complete search history.

(56) References Cited

U.S. PATENT DOCUMENTS 2,362,025 A 11/1944 Price (Continued)

FOREIGN PATENT DOCUMENTS

DE 1766151 4/1968

(Continued)

OTHER PUBLICATIONS

Notification Concerning Transmittal of International Preliminary Report on Patentability dated Jul. 6, 2006.

*Primary Examiner*—Leslie R Deak
(74) *Attorney, Agent, or Firm*—Austin J. Foley; Bell, Boyd & Lloyd LLC

(57) ABSTRACT

The present invention provides a connector device or reconstitution device (10) for placing a first container (12), such as a liquid container (e.g. flexible container or syringe), in fluid communication with a second container (14), such as a drug vial. The connector device (10) has a first sleeve (32) having a first end (36) and a second end (38). The first sleeve (32) has at the first end (36), a first attaching member (30) adapted to attach to the liquid container (12). The connector device (10) also has a second sleeve (34) having a first end (48) and a second end (50). A second attaching member (28) is attached on the second end (50) of the second sleeve (34) and is adapted to attach to the second container (14). The second attaching member (28) has a sealing member (84). A piercing member (76) projects within the sleeves (32,34) for providing a fluid flow path from the first container (12) to the second container (14). The connector device (10) is movable from the inactivated position to the activated position wherein the second sleeve (34) moves axially with respect to the first sleeve (32) and wherein the piercing member places the first container (12) and the second container (14) in fluid communication. The connector device (10) includes structure for preventing premature activation of the connector device (10).

48 Claims, 35 Drawing Sheets

U.S. PATENT DOCUMENTS 3,330,281 A 7/1967 Visser
3,330,282 A 7/1967 Visser et al.
3,336,924 A 8/1967 Sarnoff et al.
3,552,387 A 1/1971 Stevens
3,785,481 A 1/1974 Allet-Coche
3,788,369 A 1/1974 Killinger
3,796,303 A 3/1974 Allet-Coche
3,809,225 A 5/1974 Allet-Coche
3,826,261 A 7/1974 Killinger
3,902,489 A 9/1975 Carter
3,917,063 A 11/1975 Chibret et al.
3,923,059 A 12/1975 Ogle
4,014,330 A 3/1977 Genese
4,031,895 A 6/1977 Porter
4,059,112 A 11/1977 Tischlinger
4,116,196 A 9/1978 Kaplan et al.
4,161,949 A * 7/1979 Thanawalla ................ 604/411
4,170,994 A 10/1979 Komatsu
4,210,142 A 7/1980 Wörder
4,210,173 A 7/1980 Choksi et al.
4,226,330 A 10/1980 Butler
4,243,080 A 1/1981 Choksi et al.
4,247,651 A 1/1981 Ohno et al.
4,270,533 A 6/1981 Andreas
4,303,071 A 12/1981 Smith
4,328,802 A 5/1982 Curley et al.
4,373,526 A 2/1983 Kling
4,392,850 A 7/1983 Elias et al.
4,392,851 A 7/1983 Elias
4,396,383 A 8/1983 Hart
4,410,321 A 10/1983 Pearson et al.
4,411,358 A 10/1983 Bennwik et al.
4,411,662 A 10/1983 Pearson
4,424,056 A 1/1984 Urquhart et al.
4,424,057 A 1/1984 House
4,432,754 A 2/1984 Urquhart et al.
4,432,755 A 2/1984 Pearson
4,432,756 A 2/1984 Urquhart et al.
4,439,182 A 3/1984 Huang
4,458,733 A 7/1984 Lyons
4,458,811 A 7/1984 Wilkinson
4,465,471 A 8/1984 Harris et al.
4,465,488 A 8/1984 Richmond et al.
4,467,588 A 8/1984 Carveth
4,469,872 A 9/1984 Anderson et al.
4,474,574 A 10/1984 Wolfe et al.
4,479,793 A 10/1984 Urquhart et al.
4,479,794 A 10/1984 Urquhart et al.
4,484,909 A 11/1984 Urquhart et al.
4,484,920 A 11/1984 Kaufman et al.
4,493,703 A 1/1985 Butterfield
4,496,646 A 1/1985 Ito
4,505,709 A 3/1985 Froning et al.
4,507,113 A 3/1985 Dunlap
4,507,114 A 3/1985 Bohman et al.
4,511,351 A 4/1985 Theeuwes
4,511,352 A 4/1985 Theeuwes et al.
4,511,353 A 4/1985 Theeuwes
4,515,351 A 5/1985 Nakayama et al.
4,515,585 A 5/1985 Urquhart et al.
4,516,967 A 5/1985 Kopfer
4,516,977 A 5/1985 Herbert
4,518,386 A 5/1985 Tartaglia
4,519,499 A 5/1985 Stone et al.
4,521,211 A 6/1985 Theeuwes
4,525,162 A 6/1985 Urquhart et al.
4,525,978 A 7/1985 Hayase et al.
4,533,348 A 8/1985 Wolfe et al.
4,534,757 A 8/1985 Geller
4,534,758 A 8/1985 Akers et al.
4,538,918 A 9/1985 Mittleman
4,539,793 A 9/1985 Malek
4,540,089 A 9/1985 Maloney
4,540,403 A 9/1985 Theeuwes
4,543,094 A 9/1985 Barnwell
4,543,101 A 9/1985 Crouch
4,548,598 A 10/1985 Theeuwes
4,548,599 A 10/1985 Urquhart et al.
4,548,606 A 10/1985 Larkin
4,550,825 A 11/1985 Sutryn et al.
4,552,277 A 11/1985 Richardson et al.
4,552,555 A 11/1985 Theeuwes
4,552,556 A 11/1985 Urquhart et al.
4,561,110 A 12/1985 Herbert
4,564,054 A 1/1986 Gustavsson
4,568,331 A 2/1986 Fischer et al.
4,568,336 A 2/1986 Cooper
4,568,346 A 2/1986 van Dijk
4,573,967 A 3/1986 Hargrove et al.
4,573,993 A 3/1986 Hoag et al.
4,576,211 A 3/1986 Valentini et al.
4,579,553 A 4/1986 Urquhart et al.
4,581,016 A 4/1986 Gettig
4,583,971 A 4/1986 Bocquet et al.
4,583,981 A 4/1986 Urquhart et al.
4,586,922 A 5/1986 Theeuwes
4,589,867 A 5/1986 Israel
4,589,879 A 5/1986 Pearson
4,590,234 A 5/1986 Tasaka et al.
4,596,555 A 6/1986 Theeuwes
4,601,704 A 7/1986 Larkin
4,602,910 A 7/1986 Larkin
4,606,734 A 8/1986 Larkin et al.
4,607,671 A 8/1986 Aalto et al.
4,608,043 A 8/1986 Larkin
4,610,684 A 9/1986 Knox et al.
4,613,326 A 9/1986 Szwarc
4,614,267 A 9/1986 Larkin
4,614,515 A 9/1986 Tripp et al.
4,623,334 A 11/1986 Riddell
4,629,080 A 12/1986 Carveth
4,630,727 A 12/1986 Feriani et al.
4,632,244 A 12/1986 Landau
4,637,934 A 1/1987 White
4,650,475 A 3/1987 Smith et al.
4,662,878 A 5/1987 Lindmayer
4,664,650 A 5/1987 Urquhart et al.
4,668,219 A 5/1987 Israel
4,673,404 A 6/1987 Gustavsson
4,675,020 A 6/1987 McPhee
4,692,144 A 9/1987 Carpenter
4,693,706 A 9/1987 Ennis, III
4,695,272 A 9/1987 Berglund et al.
4,703,864 A 11/1987 Larkin et al.
4,715,854 A 12/1987 Vaillancourt
4,717,388 A 1/1988 Steer et al.
4,722,733 A 2/1988 Howson
4,723,956 A 2/1988 Schnell et al.
4,727,985 A 3/1988 McNeirney et al.
4,731,053 A 3/1988 Hoffman
4,735,608 A 4/1988 Sardam
4,740,103 A 4/1988 Theeuwes
4,740,197 A 4/1988 Theeuwes
4,740,198 A 4/1988 Theeuwes
4,740,199 A 4/1988 Theeuwes
4,740,200 A 4/1988 Theeuwes
4,740,201 A 4/1988 Theeuwes
4,741,734 A 5/1988 Theeuwes
4,741,735 A 5/1988 Theeuwes
4,743,229 A 5/1988 Chu
4,747,834 A 5/1988 Prindle
4,752,292 A 6/1988 Lopez et al.
4,757,911 A 7/1988 Larkin et al.
4,759,756 A * 7/1988 Forman et al. .............. 604/413

| | | | | |
|---|---|---|---|---|
| 4,778,453 | A | | 10/1988 | Lopez |
| 4,781,679 | A | | 11/1988 | Larkin |
| 4,782,841 | A | | 11/1988 | Lopez |
| 4,784,259 | A | | 11/1988 | Grabenkort |
| 4,784,658 | A | | 11/1988 | Grabenkort |
| 4,785,858 | A | | 11/1988 | Valentini et al. |
| 4,786,279 | A | | 11/1988 | Wilkinson et al. |
| 4,787,429 | A | | 11/1988 | Valentini et al. |
| 4,790,820 | A | | 12/1988 | Theeuwes |
| 4,804,360 | A | | 2/1989 | Kamen |
| 4,804,366 | A | | 2/1989 | Zdeb et al. |
| 4,808,381 | A | | 2/1989 | McGregor et al. |
| 4,816,024 | A | | 3/1989 | Sitar et al. |
| 4,819,659 | A | | 4/1989 | Sitar |
| 4,820,269 | A | | 4/1989 | Riddell |
| 4,822,351 | A | | 4/1989 | Purcell |
| 4,832,690 | A | | 5/1989 | Kuu |
| 4,834,149 | A | | 5/1989 | Fournier et al. |
| 4,834,152 | A | | 5/1989 | Howson et al. |
| 4,842,028 | A | | 6/1989 | Kaufman et al. |
| 4,850,978 | A | | 7/1989 | Dudar et al. |
| 4,857,052 | A | | 8/1989 | Theeuwes |
| 4,861,335 | A | | 8/1989 | Reynolds |
| 4,861,585 | A | | 8/1989 | Galef, Jr. et al. |
| 4,865,354 | A | | 9/1989 | Allen |
| 4,871,354 | A | | 10/1989 | Conn et al. |
| 4,871,360 | A | | 10/1989 | Theeuwes |
| 4,871,463 | A | | 10/1989 | Taylor et al. |
| 4,872,494 | A | | 10/1989 | Coccia |
| 4,874,366 | A | | 10/1989 | Zdeb et al. |
| 4,874,368 | A | | 10/1989 | Miller et al. |
| 4,883,483 | A | | 11/1989 | Lindmayer |
| 4,886,495 | A | | 12/1989 | Reynolds |
| 4,898,209 | A | * | 2/1990 | Zbed .................... 137/614.04 |
| 4,906,103 | A | | 3/1990 | Kao |
| 4,908,019 | A | | 3/1990 | Urquhart et al. |
| 4,909,290 | A | | 3/1990 | Coccia |
| 4,911,708 | A | | 3/1990 | Maezaki et al. |
| 4,915,689 | A | | 4/1990 | Theeuwes |
| 4,927,013 | A | | 5/1990 | Van Brunt et al. |
| 4,927,423 | A | | 5/1990 | Malmborg |
| 4,927,605 | A | | 5/1990 | Dorn et al. |
| 4,931,048 | A | | 6/1990 | Lopez |
| 4,936,445 | A | | 6/1990 | Grabenkort |
| 4,936,829 | A | | 6/1990 | Zdeb et al. |
| 4,936,841 | A | | 6/1990 | Aoki et al. |
| 4,944,736 | A | | 7/1990 | Holtz |
| 4,948,000 | A | | 8/1990 | Grabenkort |
| 4,950,237 | A | | 8/1990 | Henault et al. |
| 4,961,495 | A | | 10/1990 | Yoshida et al. |
| 4,968,299 | A | | 11/1990 | Ahlstrand et al. |
| 4,969,883 | A | | 11/1990 | Gilbert et al. |
| 4,973,307 | A | | 11/1990 | Theeuwes |
| 4,978,337 | A | | 12/1990 | Theeuwes |
| 4,979,942 | A | | 12/1990 | Wolf et al. |
| 4,982,875 | A | | 1/1991 | Pozzi et al. |
| 4,983,164 | A | | 1/1991 | Hook et al. |
| 4,985,016 | A | | 1/1991 | Theeuwes et al. |
| 4,986,322 | A | | 1/1991 | Chibret et al. |
| 4,994,031 | A | | 2/1991 | Theeuwes |
| 4,994,056 | A | | 2/1991 | Ikeda |
| 4,996,579 | A | | 2/1991 | Chu |
| 4,997,083 | A | | 3/1991 | Loretti et al. |
| 4,997,430 | A | | 3/1991 | Van der Heiden et al. |
| 5,002,530 | A | | 3/1991 | Recker et al. |
| 5,023,119 | A | | 6/1991 | Yamakoshi |
| 5,024,657 | A | | 6/1991 | Needham et al. |
| 5,030,203 | A | | 7/1991 | Wolf, Jr. et al. |
| 5,032,117 | A | | 7/1991 | Motta |
| 5,045,081 | A | | 9/1991 | Dysarz |
| 5,049,129 | A | | 9/1991 | Zdeb et al. |
| 5,049,135 | A | | 9/1991 | Davis |
| 5,061,264 | A | | 10/1991 | Scarrow |
| 5,064,059 | A | | 11/1991 | Ziegler et al. |
| 5,069,671 | A | | 12/1991 | Theeuwes |
| 5,074,844 | A | | 12/1991 | Zdeb et al. |
| 5,074,849 | A | | 12/1991 | Sachse |
| D323,389 | S | | 1/1992 | Aoki et al. |
| 5,080,652 | A | | 1/1992 | Sancoff et al. |
| 5,084,040 | A | | 1/1992 | Sutter |
| 5,088,996 | A | | 2/1992 | Kopfer et al. |
| 5,100,394 | A | | 3/1992 | Dudar et al. |
| 5,102,408 | A | | 4/1992 | Hamacher |
| 5,104,375 | A | | 4/1992 | Wolf et al. |
| 5,114,004 | A | | 5/1992 | Isono et al. |
| 5,114,411 | A | | 5/1992 | Haber et al. |
| 5,116,315 | A | | 5/1992 | Capozzi et al. |
| 5,116,316 | A | | 5/1992 | Sertic et al. |
| 5,117,875 | A | | 6/1992 | Marrucchi |
| 5,122,123 | A | | 6/1992 | Vaillancourt |
| 5,125,892 | A | | 6/1992 | Drudik |
| 5,125,908 | A | | 6/1992 | Cohen |
| 5,126,175 | A | | 6/1992 | Yamakoshi |
| 5,129,894 | A | | 7/1992 | Sommermeyer et al. |
| 5,137,511 | A | | 8/1992 | Reynolds |
| 5,147,324 | A | | 9/1992 | Skakoon et al. |
| 5,152,965 | A | | 10/1992 | Fisk et al. |
| 5,156,598 | A | | 10/1992 | Skakoon et al. |
| 5,158,546 | A | | 10/1992 | Haber et al. |
| 5,160,320 | A | | 11/1992 | Yum et al. |
| 5,167,642 | A | | 12/1992 | Fowles |
| 5,169,388 | A | | 12/1992 | McPhee |
| 5,171,214 | A | | 12/1992 | Kolber et al. |
| 5,171,219 | A | | 12/1992 | Fujioka et al. |
| 5,171,220 | A | | 12/1992 | Morimoto |
| 5,176,634 | A | | 1/1993 | Smith et al. |
| 5,176,673 | A | | 1/1993 | Marrucchi |
| 5,181,909 | A | | 1/1993 | McFarlane |
| 5,186,323 | A | | 2/1993 | Pfleger |
| 5,188,615 | A | | 2/1993 | Haber et al. |
| 5,188,629 | A | | 2/1993 | Shimoda |
| 5,195,658 | A | | 3/1993 | Hoshino |
| 5,195,986 | A | | 3/1993 | Kamen |
| 5,196,001 | A | | 3/1993 | Kao |
| 5,199,947 | A | | 4/1993 | Lopez et al. |
| 5,199,948 | A | | 4/1993 | McPhee |
| 5,200,200 | A | | 4/1993 | Veech |
| 5,201,705 | A | | 4/1993 | Berglund et al. |
| 5,207,509 | A | | 5/1993 | Herbert |
| 5,209,201 | A | | 5/1993 | Horie et al. |
| 5,209,347 | A | | 5/1993 | Fabisiewicz et al. |
| 5,211,201 | A | | 5/1993 | Kamen et al. |
| 5,211,285 | A | | 5/1993 | Haber et al. |
| 5,222,946 | A | | 6/1993 | Kamen |
| 5,226,878 | A | | 7/1993 | Young |
| 5,226,900 | A | | 7/1993 | Bancsi et al. |
| RE34,365 | E | | 8/1993 | Theeuwes |
| 5,232,029 | A | | 8/1993 | Knox et al. |
| 5,232,109 | A | | 8/1993 | Tirrell et al. |
| 5,246,142 | A | | 9/1993 | DiPalma et al. |
| 5,247,972 | A | | 9/1993 | Tetreault |
| 5,250,028 | A | | 10/1993 | Theeuwes et al. |
| 5,257,985 | A | | 11/1993 | Puhl |
| 5,257,986 | A | | 11/1993 | Herbert et al. |
| 5,257,987 | A | | 11/1993 | Athayde et al. |
| 5,259,843 | A | | 11/1993 | Watanabe et al. |
| 5,259,954 | A | | 11/1993 | Taylor |
| 5,261,902 | A | | 11/1993 | Okada et al. |
| 5,267,646 | A | | 12/1993 | Inoue et al. |
| 5,267,957 | A | | 12/1993 | Kriesel et al. |
| 5,279,576 | A | | 1/1994 | Loo et al. |
| 5,279,579 | A | | 1/1994 | D'Amico |
| 5,279,583 | A | | 1/1994 | Shober, Jr. et al. |
| 5,279,605 | A | * | 1/1994 | Karrasch et al. ........... 604/403 |
| 5,281,198 | A | | 1/1994 | Haber et al. |
| 5,281,206 | A | | 1/1994 | Lopez |

5,286,257 A 2/1994 Fischer
5,287,961 A 2/1994 Herran
5,289,585 A 2/1994 Kock et al.
5,289,858 A 3/1994 Grabenkort
5,302,603 A 4/1994 Crawley et al.
5,303,751 A 4/1994 Slater et al.
5,304,130 A 4/1994 Button et al.
5,304,163 A 4/1994 Bonnici et al.
5,304,165 A 4/1994 Haber et al.
5,306,242 A 4/1994 Joyce et al.
5,308,287 A 5/1994 Gunsing
5,308,347 A 5/1994 Sunago et al.
5,320,603 A 6/1994 Vetter et al.
5,328,464 A 7/1994 Kriesel et al.
5,330,048 A 7/1994 Haber et al.
5,330,426 A 7/1994 Kriesel et al.
5,330,450 A 7/1994 Lopez
5,330,462 A 7/1994 Nakamura
5,330,464 A 7/1994 Mathias et al.
5,332,399 A 7/1994 Grabenkort et al.
5,334,178 A 8/1994 Haber et al.
5,334,180 A 8/1994 Adolf et al.
5,334,188 A 8/1994 Inoue et al.
5,335,773 A 8/1994 Haber et al.
5,336,180 A 8/1994 Kriesel et al.
5,342,346 A 8/1994 Honda et al.
5,342,347 A 8/1994 Kikuchi et al.
5,344,414 A 9/1994 Lopez et al.
5,348,060 A 9/1994 Futagawa et al.
5,348,600 A 9/1994 Ishii
5,350,372 A 9/1994 Ikeda et al.
5,350,546 A 9/1994 Takeuchi et al.
5,352,191 A 10/1994 Sunago et al.
5,352,196 A 10/1994 Haber et al.
5,352,210 A 10/1994 Marrucchi
5,353,961 A 10/1994 Debush
5,356,380 A 10/1994 Hoekwater et al.
5,358,501 A 10/1994 Meyer
5,360,410 A 11/1994 Wacks
5,364,350 A 11/1994 Dittmann
5,364,369 A 11/1994 Reynolds
5,364,371 A 11/1994 Kamen
5,364,384 A 11/1994 Grabenkort et al.
5,368,586 A 11/1994 Van Der Heiden et al.
5,370,164 A 12/1994 Galloway
5,373,966 A 12/1994 O'Reilly et al.
5,374,264 A 12/1994 Wadsworth, Jr.
5,376,079 A 12/1994 Holm
5,380,281 A 1/1995 Tomellini et al.
5,380,287 A 1/1995 Kikuchi et al.
5,380,315 A 1/1995 Isono et al.
5,385,545 A 1/1995 Kriesel et al.
5,385,546 A 1/1995 Kriesel et al.
5,385,547 A 1/1995 Wong et al.
5,386,372 A 1/1995 Kobayashi et al.
5,393,497 A 2/1995 Haber et al.
5,397,303 A * 3/1995 Sancoff et al. ................ 604/82
5,398,851 A 3/1995 Sancoff et al.
5,401,253 A 3/1995 Reynolds
5,409,141 A 4/1995 Kikuchi et al.
5,423,421 A 6/1995 Inoue et al.
5,423,753 A 6/1995 Fowles et al.
5,423,793 A 6/1995 Isono et al.
5,423,796 A 6/1995 Shikhman et al.
5,425,447 A 6/1995 Farina
5,425,528 A 6/1995 Rains et al.
5,429,256 A 7/1995 Kestenbaum
5,429,603 A 7/1995 Morris
5,429,614 A 7/1995 Fowles et al.
5,435,076 A 7/1995 Hjertman et al.
5,445,631 A 8/1995 Uchida
5,456,678 A 10/1995 Nicoletti
5,458,593 A 10/1995 Macabasco et al.
5,462,526 A 10/1995 Barney et al.
5,464,123 A 11/1995 Scarrow
5,467,337 A 11/1995 Matsumoto
5,470,327 A 11/1995 Helgren et al.
5,472,022 A 12/1995 Michel et al.
5,472,422 A 12/1995 Ljungquist
5,474,540 A 12/1995 Miller et al.
5,474,546 A * 12/1995 Ambrisco et al. ........... 604/411
5,478,337 A 12/1995 Okamoto et al.
5,484,406 A 1/1996 Wong et al.
5,484,410 A 1/1996 Kriesel et al.
5,489,266 A 2/1996 Grimard
5,490,848 A 2/1996 Finley et al.
5,492,147 A 2/1996 Challender et al.
5,492,219 A 2/1996 Stupar
5,493,774 A 2/1996 Grabenkort
5,494,190 A 2/1996 Boettcher
5,501,887 A 3/1996 Tanaka et al.
5,509,898 A 4/1996 Isono et al.
5,510,115 A 4/1996 Breillatt, Jr. et al.
5,514,090 A 5/1996 Kriesel et al.
5,520,972 A 5/1996 Ezaki et al.
5,522,804 A 6/1996 Lynn
5,526,853 A 6/1996 McPhee et al.
5,531,683 A 7/1996 Kriesel et al.
5,533,389 A 7/1996 Kamen et al.
5,533,973 A 7/1996 Piontek et al.
5,533,994 A 7/1996 Meyer
5,535,746 A 7/1996 Hoover et al.
5,536,469 A 7/1996 Jonsson et al.
5,538,506 A 7/1996 Farris et al.
5,540,674 A 7/1996 Karas et al.
5,547,471 A 8/1996 Thompson et al.
5,554,125 A 9/1996 Reynolds
5,554,128 A 9/1996 Hedges
5,560,403 A 10/1996 Balteau et al.
5,566,729 A 10/1996 Grabenkort et al.
5,569,191 A 10/1996 Meyer
5,569,192 A 10/1996 van der Wal
5,569,193 A 10/1996 Hofstetter et al.
5,573,527 A 11/1996 Macabasco et al.
5,575,310 A 11/1996 Kamen et al.
5,577,369 A 11/1996 Becker et al.
5,584,808 A 12/1996 Healy
5,593,028 A 1/1997 Haber et al.
5,595,314 A 1/1997 Weiler
5,596,193 A 1/1997 Chutjian et al.
5,603,695 A 2/1997 Erickson
5,603,696 A 2/1997 Williams et al.
5,605,542 A 2/1997 Tanaka et al.
5,611,792 A 3/1997 Gustafsson
5,620,434 A 4/1997 Brony
5,624,405 A 4/1997 Futagawa et al.
5,641,010 A 6/1997 Maier
5,669,891 A 9/1997 Vaillancourt
5,688,254 A 11/1997 Lopez et al.
5,709,666 A 1/1998 Reynolds
5,743,312 A 4/1998 Pfeifer et al.
5,827,262 A 10/1998 Neftel et al.
5,897,526 A 4/1999 Vaillancourt
5,989,237 A 11/1999 Fowles et al.
6,019,750 A 2/2000 Fowles et al.
6,022,339 A 2/2000 Fowles et al.
6,063,068 A 5/2000 Fowles et al.
6,071,270 A 6/2000 Fowles et al.
6,090,092 A 7/2000 Fowles et al.
6,378,714 B1 4/2002 Jansen et al.
6,610,040 B1 * 8/2003 Fowles et al. ............... 604/413
6,852,103 B2 * 2/2005 Fowles et al. ............... 604/413
7,074,216 B2 * 7/2006 Fowles et al. ............... 604/413
2002/0123736 A1 9/2002 Fowles et al.

| | | | |
|---|---|---|---|
| 2003/0055376 A1 | 3/2003 | Delay | |
| 2003/0091468 A1 | 5/2003 | Buchanan | |

FOREIGN PATENT DOCUMENTS

| | | | |
|---|---|---|---|
| DE | 1913926 | | 3/1969 |
| EP | 0 091 310 | A2 | 4/1983 |
| EP | 0 126 718 | A2 | 11/1984 |
| EP | 0 285 424 | A1 | 3/1988 |
| EP | 0 335 378 | A2 | 4/1989 |
| EP | 0 345 230 | A2 | 12/1989 |
| EP | 0 363 770 | A1 | 4/1990 |
| EP | 0 395 758 | A1 | 7/1990 |
| EP | 0 499 764 | A1 | 8/1991 |
| EP | 0 692 235 | A1 | 7/1994 |
| EP | 0961608 | | 12/1999 |
| GB | 1 419 061 | | 11/1972 |
| GB | 2 211 104 | A | 10/1987 |
| JP | 4156849 | A2 | 10/1990 |
| JP | 7255820 | A2 | 3/1994 |
| JP | 8238300 | A2 | 3/1995 |
| JP | 09-276370 | | 4/1996 |
| JP | 10024089 | A2 | 1/1998 |
| WO | WO 83/03540 | | 10/1983 |
| WO | WO 85/03432 | | 1/1985 |
| WO | WO 90/03536 | | 9/1989 |
| WO | WO 93/02723 | | 6/1992 |
| WO | WO 92/11897 | | 7/1992 |
| WO | WO 93/09825 | | 5/1993 |
| WO | WO 94/00094 | | 1/1994 |
| WO | WO 94/00094 | A1 | 1/1994 |
| WO | WO 97/25015 | | 7/1997 |
| WO | WO 99/27886 | | 6/1999 |

* cited by examiner

FIG. 44
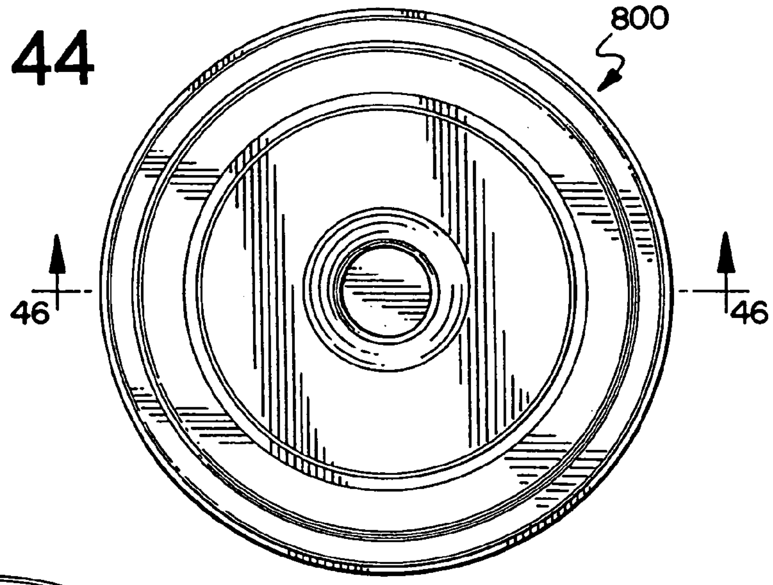
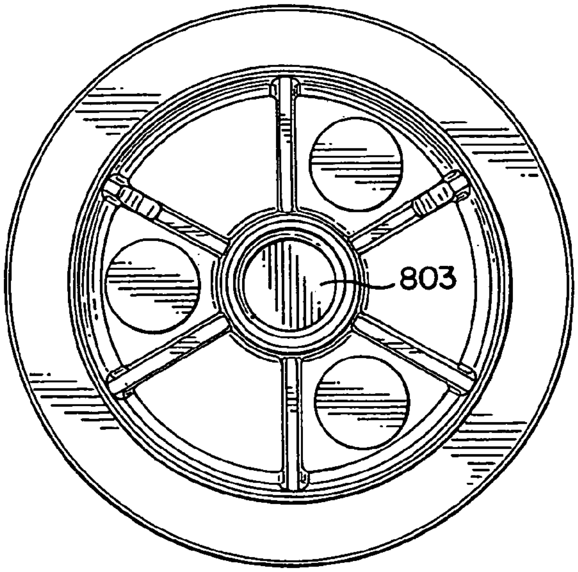
FIG. 45
FIG. 46
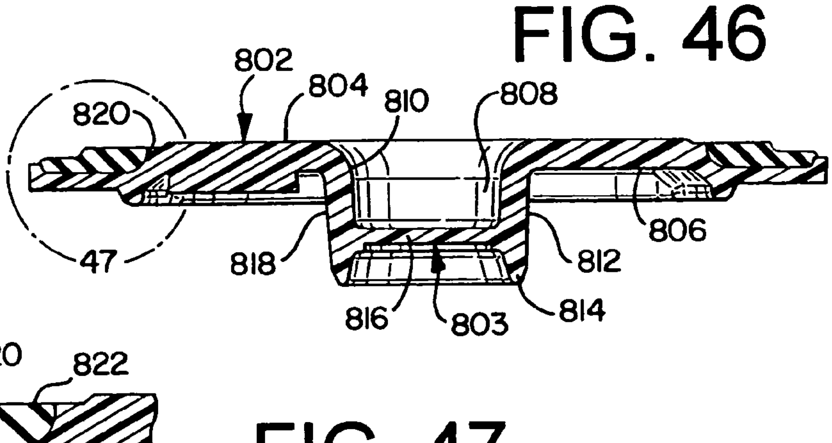
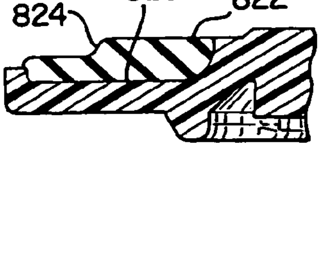
FIG. 47

SLIDING RECONSTITUTION DEVICE FOR A DILUENT CONTAINER

RELATED APPLICATION

This is a continuation-in-part application of U.S. application Ser. No. 10/106,716 filed Mar. 26, 2002, now U.S. Pat. No. 7,074,216, which is a continuation-in-part application of U.S. application Ser. No. 09/561,666, filed May 2, 2000, now U.S. Pat. No. 6,582,415, which is a continuation application of U.S. application Ser. No. 09/153,816, filed Sep. 15, 1998, now U.S. Pat. No. 6,113,583, patented Sep. 5, 2000, which applications are incorporated herein by reference and made a part hereof.

TECHNICAL FIELD

The present invention relates generally to the delivery of a beneficial agent to a patient. More specifically, the present invention relates to an improved device for reconstituting a beneficial agent to be delivered to a patient.

BACKGROUND OF THE INVENTION

Many drugs are unstable even for a short period of time in a dissolved state and therefore are packaged, stored, and shipped in a powdered or lyophilized state to increase their shelf life. In order for powdered drugs to be given intravenously to a patient, the drugs must first be placed in liquid form. To this end, these drugs are mixed or reconstituted with a diluent before being delivered intravenously to a patient. The diluents may be, for example, a dextrose solution, a saline solution, or even water. Typically the drugs are stored in powdered form in glass vials or ampules.

Other drugs, although in a liquid state, must still be diluted before administering to a patient. For example, some chemotherapy drugs are stored in glass vials or ampules, in a liquid state, but must be diluted prior to use. As used herein, reconstitution means to place the powdered drug in a liquid state, as well as, the dilution of a liquid drug.

The reconstitution procedure should be performed under sterile conditions. In some procedures for reconstituting, maintaining sterile conditions is difficult. Moreover, some drugs, such as chemotherapy drugs, are toxic and exposure to the medical personnel during the reconstitution procedure can be dangerous. One way of reconstituting a powdered drug is to inject the liquid diluent directly into the drug vial. This can be performed by use of a combination-syringe and syringe needle having diluent therein. In this regard, drug vials typically include a pierceable rubber stopper. The rubber stopper of the drug vial is pierced by the needle, and liquid in the syringe is then injected into the vial. The vial is shaken to mix the powdered drug with the liquid. After the liquid and drug are mixed, a measured amount of the reconstituted drug is then drawn into the syringe. The syringe is then withdrawn from the vial and the drug can then be injected into the patient. Another method of drug administration is to inject the reconstituted drug, contained in the syringe, into a parenteral solution container. Examples of such containers include a MINI-BAG™ flexible parenteral solution container or VIAFLEX® flexible parenteral solution container sold by Baxter Healthcare Corporation of Deerfield, Ill. These parenteral solution containers may already have therein dextrose or saline solutions. The reconstituted drug is injected into the container, mixed with the solution in the parenteral solution container and delivered through an intravenous solution administration set to a vein access site of the patient.

Another method for reconstituting a powdered drug utilizes a reconstitution device sold by Baxter Healthcare Corporation, product code No. 2B8064. That device includes a double pointed needle and guide tubes mounted around both ends of the needle. This reconstitution device is utilized to place the drug vial in fluid communication with a flexible-walled parenteral solution container. Once the connection is made by piercing a port of the flexible container with one end of the needle and the vial stopper with the other end of the needle, liquid in the solution container may be forced through the needle into the drug vial by squeezing the sidewalls of the solution container. The vial is then shaken to mix the liquid and drug. The liquid in the vial is withdrawn by squeezing air from the solution container into the vial. When compression of the flexible walled solution container is stopped, the pressurized air in the vial acts as a pump to force the liquid in the vial back into the solution container.

An improvement to this product is the subject of commonly assigned U.S. Pat. No. 4,607,671 to Aalto et al. The device of the '671 patent includes a series of bumps on the inside of a sheath to grip a drug vial. These bumps hinder the inadvertent disconnection of the device with the vial.

U.S. Pat. No. 4,759,756 discloses a reconstitution device which, in an embodiment, includes an improved vial adaptor and bag adaptor that permit the permanent coupling of a vial and liquid container. The bag adaptor is rotatable relative to the vial adaptor to either block fluid communication in a first position or effect fluid communication in a second position.

Another form of reconstitution device is seen in commonly assigned U.S. Pat. No. 3,976,073 to Quick et al. Yet another type of reconstitution device is disclosed in U.S. Pat. No. 4,328,802 to Curley et al., entitled "Wet-Dry Syringe Package" which includes a vial adaptor having inwardly directed retaining projections to firmly grip the retaining cap lip of a drug vial to secure the vial to the vial adaptor. The package disclosed by Curley et al. is directed to reconstituting a drug by use of a liquid-filled syringe.

Other methods for reconstituting a drug are shown, for example, in commonly assigned U.S. Pat. Nos. 4,410,321 to Pearson et al., entitled "Close Drug Delivery System"; U.S. Pat. Nos. 4,411,662 and 4,432,755 to Pearson, both entitled "Sterile Coupling"; U.S. Pat. No. 4,458,733 to Lyons entitled "Mixing Apparatus"; and U.S. Pat. No. 4,898,209 to Zdeb entitled "Sliding Reconstitution Device With Seal."

Other related patents include U.S. Pat. No. 4,872,867 to Kilinger entitled "Wet-Dry Additive Assembly"; U.S. Pat. No. 3,841,329 to Kilinger entitled "Compact Syringe"; U.S. Pat. No. 3,826,261 to Kilinger entitled "Vial and Syringe Assembly"; U.S. Pat. No. 3,826,260 to Kilinger entitled "Vial and Syringe Combination"; U.S. Pat. No. 3,378,369 to Kilinger entitled "Apparatus for Transferring Liquid Between a Container and a Flexible Bag"; and German specification DE OS 36 27 231.

Commonly assigned U.S. Pat. No. 4,898,209 to Zdeb (the '209 Patent), discloses a sliding reconstitution device which solved some of the problems discussed above. For example, the connector allowed for preattaching the device to a vial without piercing a closure of the vial. However, no seal was provided on the opposite end of the connector so the vial and device assembly had to be used immediately after connection or stored in a sterile environment, such as under a hood.

The '209 Patent discloses a first sleeve member that is mounted concentrically about a second sleeve member. The sleeve members can be moved axially with respect to each other to cause a needle or cannula to pierce a drug container and a diluent container to place the containers in fluid communication with each other.

The process for using the '209 connector required three distinct steps. The sleeves had to be rotated with respect to one another to move the device into an unlocked position. The sleeves were then moved axially with respect to one another to an activated position to pierce closures of the containers. The sleeves had to be rotated again to lock the sleeves in the activated position.

However, it is possible for the device of the '209 Patent to be easily and inadvertently disassembled when being moved to the activated position. The second sleeve is capable of sliding entirely though the first sleeve member and becoming disassociated into separate parts. This would require the medical personnel to either reassemble the device or dispose of it due to contamination.

Also, the device of the '209 Patent did not provide for a visual indication that the device was in the activated position. It was also possible for the device to be inadvertently moved to the inactivated position, by rotating the first and second sleeve members in a direction opposite of the third step described above.

Additionally, it was possible for the second container, which is frequently a vial, to rotate within the device. This could cause coring of the vial stopper which could lead to leakage of the vial stopper. Additionally it was possible for a vial to be misaligned while being attached to the device causing the attachment process to be difficult for medical personnel. Further, the connector only releasably attached to the vial. Removal of the vial could remove all tamper evident indications that the reconstitution step has occurred and could lead to a second unintended dosage of medicine to be administered. Finally, the seal had a sleeve that covered only a portion of the cannula. The sleeve of the seal was relatively resilient and had the tendency of pushing the connector away from the drug container when docked thereto.

Yet another connector for attaching a drug vial to a parenteral solution container is disclosed in U.S. Pat. No. 4,675,020 ("the '020 patent"). The '020 patent discloses a connector having an end that docks to a drug vial and an opposite end that connects to the solution container. A shoulder and an end surface of the vial are held between first and second jaws of the vial end of the connector. The second jaws 71 terminate in a relatively sharp point that digs into and deforms the outermost end surface 94 of the vial sufficiently to accommodate dimensional variations between the shoulder and the outermost end surface of the vial. The marks that are left in the deformable end surface of the vial are intended to provide a tamper evident feature. However, tamper evident marks will not be left in vials that have a cap that is too short to impinge upon the sharp points.

The connector has a spike 25 that penetrates stoppers on the vial and on the solution container to place these containers in fluid communication. However, because the spike 25 extends outward beyond skirt sections 57, the connector of the '020 patent cannot be preattached to the fluid container or the drug container without piercing the stoppers of each. (The '020 patent states that the connector may be preassembled onto a drug vial, but there is no explanation of the structure of such a device. (Col. 6, lines 40-49)). This is undesirable as it initiates the time period in which the drug must be used, and typically this is a short period relative to the normal shelf-life of the product.

Also, the connector of the '020 patent does not provide a structure for preventing a docked vial from rotating. A closure of the vial can become damaged or cored upon rotation, which in turn, can lead to particles from the closure from entering the fluid that eventually passes to a patient. It can also lead to leakage of the closure of the vial.

Another connector for attaching a drug vial to a flexible container is disclosed in commonly assigned U.S. patent application Ser. No. 08/986,580, now U.S. Pat. No. 6,071, 270. This connector has a piercing member mounted between two sleeves slidably mounted to one another. The bag connecting end is sealed by a peelable seal material. The seal material must be removed before connecting to the flexible container. Removal of the seal material exposes the piercing member to the outside environment thereby breaching the hermetic seal of the piercing member.

Another connector for attaching a drug vial to a flexible solution container is disclosed in U.S. Pat. No. 5,352,191 ("the '191 Patent"). The connector has a communicating portion having a communicating passage disposed at a top portion of the flexible container wherein one end of the communicating portion extends into the flexible container. The drug vial is fitted partially or wholly into an opposite end of the communicating portion. A membrane is disposed in the communicating passage for closing the passage. The connector also includes a puncturing needle unit mounted in the communicating passage for enabling the drug vial and flexible container to communicate with each other. When the puncturing needle unit is pressed externally through the flexible container, the needle breaks the membrane and opening of the drug vial to enable the drug vial and container to communicate with each other.

U.S. Pat. No. 5,380,315 and EP 0843992 disclose another connector for attaching a drug vial to a flexible solution container. Similar to the '191 patent, this patent and patent application have a communication device in the form of spike that is mounted within the flexible container. The communication device is externally pressed towards a drug vial to puncture the drug vial and communicate the drug vial with the flexible container.

U.S. Pat. Nos. 5,478,337 discloses a device for connecting a vial to a flexible container. This patent requires the vial to be shipped pre-assembled to the connector, and, therefore, does not allow for medical personnel to selectively attach a vial to the connector.

Finally, U.S. Pat. No. 5,364,386 discloses a device for connecting a vial to a medical fluid container. The device includes a screw cap 32 that must be removed before inserting the vial. Removing the screw cap, however, potentially exposes the piercing member 48 to contaminants as the piercing member is not hermetically sealed.

While the reconstitution devices of the prior art provide a number of advantageous features, they nevertheless have certain limitations. The present invention is provided to overcome certain of these limitations and other drawbacks and problems of the prior art, and to provide new features not heretofore available.

SUMMARY OF THE INVENTION

The present invention provides a fluid reconstitution device for placing a first container, such as a diluent or liquid container (e.g. flexible container or syringe), in fluid communication with a second container, such as a drug vial. To this end, there is provided a connector device for establishing fluid communication between the liquid container and the drug vial. The connector has a piercing member having a first end and a second end and a central fluid pathway. The piercing member is mounted to the liquid container and has fluid accessing portions hermetically sealed from an outside environment. A vial receiving chamber is associated with the piercing member and is dimensioned to connect to the vial. The vial may be selectively attached to the device without piercing the closure of the vial and without breaching the hermetic seal of the fluid accessing portions of the piercing member. Means are provided for connecting the vial receiving chamber to the liquid container. The device is movable from an inactivated position, where the piercing member is outside the sidewalls and no fluid flows between the liquid container and the drug vial, to an activated position, where fluid flows through the fluid pathway between the liquid container and the drug vial. The device is movable from the inactivated position to the activated position by a force applied to the device outside the liquid container.

According to another aspect of the invention, there is provided a hub mounting the piercing member within the means for connecting the vial receiving chamber to the liquid container and a protuberance attached to the means for connecting the vial receiving chamber to the liquid container and dimensioned for allowing movement of the hub from a first position to a second position wherein the hub moves past the protuberance. When the device is moved from the activated position to a deactivated position, the protuberance prevents the hub from returning to the first position.

According to another aspect of the invention, there is provided a tamper evident strip associated with the device for indicating when the device has been moved from the inactivated position to the activated position.

According to another aspect of the invention, the device has a first attaching member in the form of a port connector having a port snap connected to a port sleeve. The port snap has a flange extending from an outer surface and is connected to a first sleeve member wherein the flange engages a protrusion on the first sleeve member. The port sleeve is adapted to attach to the liquid container. The port sleeve preferably has a membrane at one end.

According to yet another aspect of the invention, the device includes a gripper assembly attached to the second end of the second sleeve. The gripper assembly has a base and an annular wall portion extending from the base and a plurality of fingers circumjacent the wall portion. The fingers are circumferentially spaced defining a vial receiving chamber adapted to receive the vial, wherein one finger has a tab adapted to engage an underside of the neck and one finger has a standing rib adapted to engage a side portion of the vial closure. A first annular rim extends from the base and a second annular rim extends collectively from the fingers and in spaced relation to the first annular rim.

According to a further aspect of the invention, the gripper assembly has a disk-shaped panel extending to bottom portions of the fingers. The panel has a center opening therethrough and supports an annular rim extending from the panel. The annular rim is adapted to form a fluid tight seal against a target site of a closure of a container.

According to another aspect of the invention, there is provided a sealing member preferably in the form of a septum having a disk having opposing first and second surfaces. The disk has a center hub having a generally thickened cross-section. The first surface has a first annular groove receiving the first annular rim. The second surface has a second annular groove receiving the second annular rim. The second surface further has an annular ridge having a sidewall tapering axially-outwardly, so that the annular ridge is capable of forming a fluid tight seal with the vial when the vial is received by the fingers of the gripper assembly.

According to another aspect of the invention, the thickened center hub substantially blocks the central fluid passageway of the piercing member as the center hub is penetrated by the piercing member but before the piercing member completely penetrates the piercing center hub.

According to a further aspect of the invention, a septum is provided that includes a cap positioned within the annular ridge. The cap is adapted to provide a fluid tight seal against a target site of a closure of a container.

According to yet another aspect of the invention, the septum could include structure to provide a dual seal against the closure of the container.

According to yet another aspect of the invention, the septum can take various forms and have rigid or flexible portions.

According to a further aspect of the invention, a connector is provided for establishing fluid communication between a first container and a second container. A first sleeve is adapted to be connected to the first container. A second sleeve is adapted to be connected to the second container. The second sleeve is associated with the first sleeve and is movable axially with respect thereto from an inactivated position to an activated position. Means are provided for preventing premature activation of the connector.

According to another aspect of the invention, a locking device is provided for use in connection with a medical connector for establishing fluid communication between a first container and a second container. The medical connecter includes a first sleeve, a second sleeve and a piercing member for placing the first and second containers in fluid communication. The locking device includes a means for preventing premature activation of the medical connector.

According to another aspect of the invention, a locking device is provided for use in connection with a medical connector for establishing fluid communication between a first container and a second container. The medical connector includes a first sleeve, a second sleeve and a piercing member for placing the first and second containers in fluid communication. The device includes a member removably positioned on the first sleeve and abutting the second sleeve and a structure associated with the first sleeve or first container.

According to another aspect of the invention, a connector device for establishing fluid communication between a first container and a second container includes a first sleeve member having a first end and a second end. It further includes a second sleeve member having a first end and a second end. The second sleeve is associated with the first sleeve member and is movable axially with respect thereto from an inactivated position to an activated position. A piercing member is positioned in a sleeve for providing a fluid flow pathway between the first container and second container when the device is in the activated position. A locking member is associated with the first sleeve for preventing premature activation of the device.

According to yet another aspect of the invention, a connector device for establishing fluid communication between a first container and a second container includes a first sleeve member having a first end and a second end. A port connector has a port snap connected to a port sleeve, and the port snap has a flange extending from an outer surface. The port connector is connected to the first sleeve at the first end of the sleeve and to the first container. A second sleeve member has a first end and a second end. The second sleeve member is associated with the first sleeve member and is movable axially with respect thereto from an inactivated position to an activated position. An attaching member on the second end of the second sleeve is adapted to attach the second sleeve member to the second container. A piercing member is positioned in a sleeve for piercing a closure of a container and providing a fluid flow pathway between the first container and second container when the device is in the activated position. A clip is removably secured to the first sleeve and abuts the flange, or other structure associated with the first sleeve, and the second sleeve for preventing premature activation of the device.

According to a further aspect of the invention, a connector device for establishing fluid communication between a first container and a second container includes a first sleeve member having a first end, a second end and at least one raised protuberance proximate to the second end. A second sleeve member has a first end, a second end and an annular rim with at least one opening, the second sleeve member is associated with the first sleeve member and is movable rotationally and axially with respect thereto from an inactivated position to an activated position. The raised protuberance and the opening of the rib may be misaligned by rotational movement of the sleeves when in the inactivated position. The sleeve members may be moved axially to the activated position when the raised protuberance and the opening of the rib are aligned. A piercing member is positioned in the sleeve members and projects from one of the first and second sleeve members for providing a fluid flow path between the first container and the second container.

According to another aspect of the invention, a connector device for establishing fluid communication between a first container and a second container includes a first sleeve member having a first end and a second end. A second sleeve member has a first end and a second end. The second sleeve member is associated with the first sleeve member and is movable rotationally and axially with respect thereto from an inactivated position to an activated position. The device includes integral means for preventing premature activation of the device. A piercing member is positioned in the sleeve members and projects from one of the first and second sleeve members for providing a fluid flow path between the first container and the second container.

According to a further aspect of the invention, a connector device for establishing fluid communication between a first container and a second container includes a first sleeve member having a first end and a second end. A second sleeve member has a first end and a second end. The second sleeve member is associated with the first sleeve member and is movable axially with respect thereto from an inactivated position to an activated position. A locking member is arranged on the first and second sleeve member which cooperatively engages to provide resistance when the first and second sleeve members are axially moved from the inactivated position to the activated position. A piercing member is positioned in the chamber and projects from one of the first and second sleeve members for providing a fluid flow path between the first container and the second container.

According to yet another aspect of the invention, a septum is provided for a connector wherein the connector has an end to attach to a closure of a container. The closure of the container has a target site, the connector further has a piercing member therein for piercing the target site of the closure. The septum includes a disk having opposing first and second surfaces. The disk further has a center portion. A rigid annular ring is supported by the center portion of the disk and extends from the second surface of the disk, the annular ring being capable of forming a fluid tight seal with the target site of the closure. An annular flexible collar is secured to the first surface of the disk.

According to yet another aspect of the invention, a method of activating a connector device includes the steps of providing a connector device having first and second sleeve members wherein the first sleeve member is attached to a first container and the second sleeve member is attached to a second container wherein the first container contains a fluid and the second container contains a drug. The second container is positioned on a hard surface. A force is applied to the connector device in the direction of the second container such that the first sleeve member of the connector device moves in the direction of the second container and places the connector device into an activated position.

According to another aspect of the invention, when the connector is activated, the piercing member first pierces the closure of the vial and then pierces the closure of the flexible container.

According to another aspect of the invention, one of the first sleeve and the second sleeve may contain a lubricant additive that assists in providing a more uniform activation force. In one preferred embodiment, the first sleeve has a sleeve ridge and the second sleeve has a sleeve rib. One of the sleeve ridge and the sleeve rib has the lubricant additive. The second sleeve may have a discontinuous annulus to further assist in providing a more uniform activation force.

According to a further aspect of the invention, the connector utilizes a finger assembly dimensioned to conform to a vial to be attached to the connector. In one embodiment, the connector can be structured to utilize a first finger assembly adapted to connect to a vial of a first size, or to utilize a second finger assembly adapted to connect to a vial of a size different from the first size.

According to yet another embodiment of the invention, the connector provides a sealed fluid pathway when the connector is in the activated position.

Other features and advantages of the invention will become apparent from the following description taken in conjunction with the following drawings.

BRIEF DESCRIPTION OF THE DRAWINGS

FIG. 44 is a top view of another embodiment of the sealing member used in the connector device of the present invention;

FIG. 45 is a bottom view of the sealing member of FIG. 44;

FIG. 46 is a cross-sectional view of the sealing member taken along lines 46-46 of FIG. 44;

FIG. 47 is a partial cross-sectional view of the sealing member of FIG. 46, in area 47.

DETAILED DESCRIPTION OF THE PREFERRED EMBODIMENTS

Figure 1:
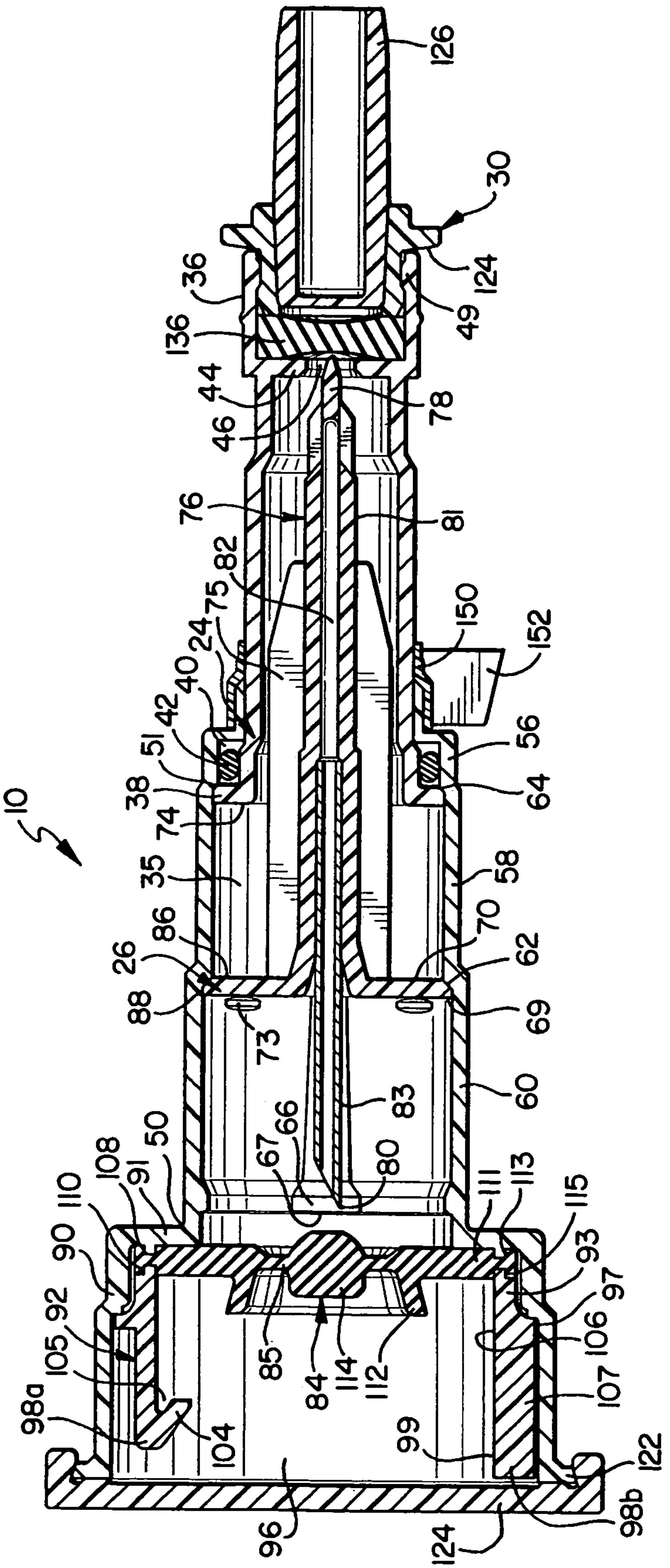
FIG. 1 is a cross-sectional elevation view of a connector device of the present invention.

While the invention is susceptible of embodiment in many different forms, there is shown in the drawings and will herein be described in detail preferred embodiments of the invention. It is to be understood that the present disclosure is to be considered as an exemplification of the principles of the invention. This disclosure is not intended to limit the broad aspect of the invention to the illustrated embodiments.

The present invention provides a connector device that is used to mix two substances within separate containers. More particularly, the invention provides a device to reconstitute a drug with a diluent. To accomplish the reconstitution of the drug, the invention provides an improved connecting device for attaching to a first container, commonly a flexible bag or a syringe, containing a diluent, to a second container, commonly a vial containing a drug to be reconstituted. The connector provides fluid communication between the two containers through a hermetically sealed piercing member so that the drug may be reconstituted, and delivered to a patient. What is meant by hermetically sealed is that the portions of the piercing member that contact the fluid and that pierce the closures of the two containers are sealed from the outside environment.

While the diluent will be a liquid, the beneficial agent may be either a powder or a lyophilized drug to be dissolved or a liquid drug to be reduced in concentration. The devices of the present invention provide the benefit of allowing medical personnel to selectively attach a vial of their choice to the connector. Thus, hospitals and pharmacies do not have to stock pre-packaged drug vial and connector assemblies. Further, the connectors of the present invention allow for docking a vial to the connector without breaching the hermetic seal of a piercing member associated with the connector and without piercing the closure of the vial. Thus, a vial may be pre-docked to the device of the present invention for essentially the full period the drug is active. Further, the device of the present invention can be activated by applying a force directly to the connector without necessarily contacting sidewalls of the first and second containers.

Figure 2:
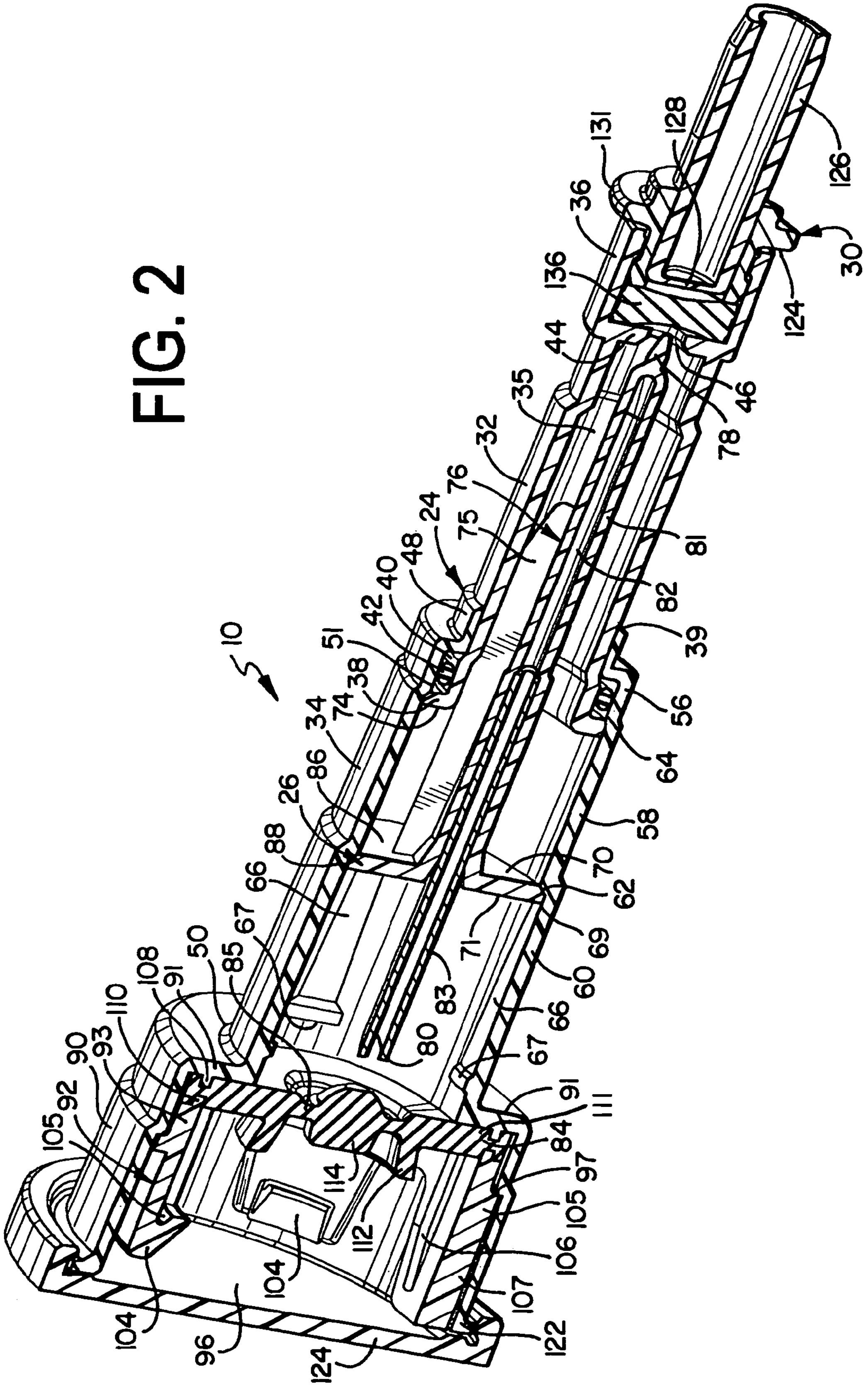
FIG. 2 is a cross-sectional perspective view of the connector device of the present invention.
Figure 4:
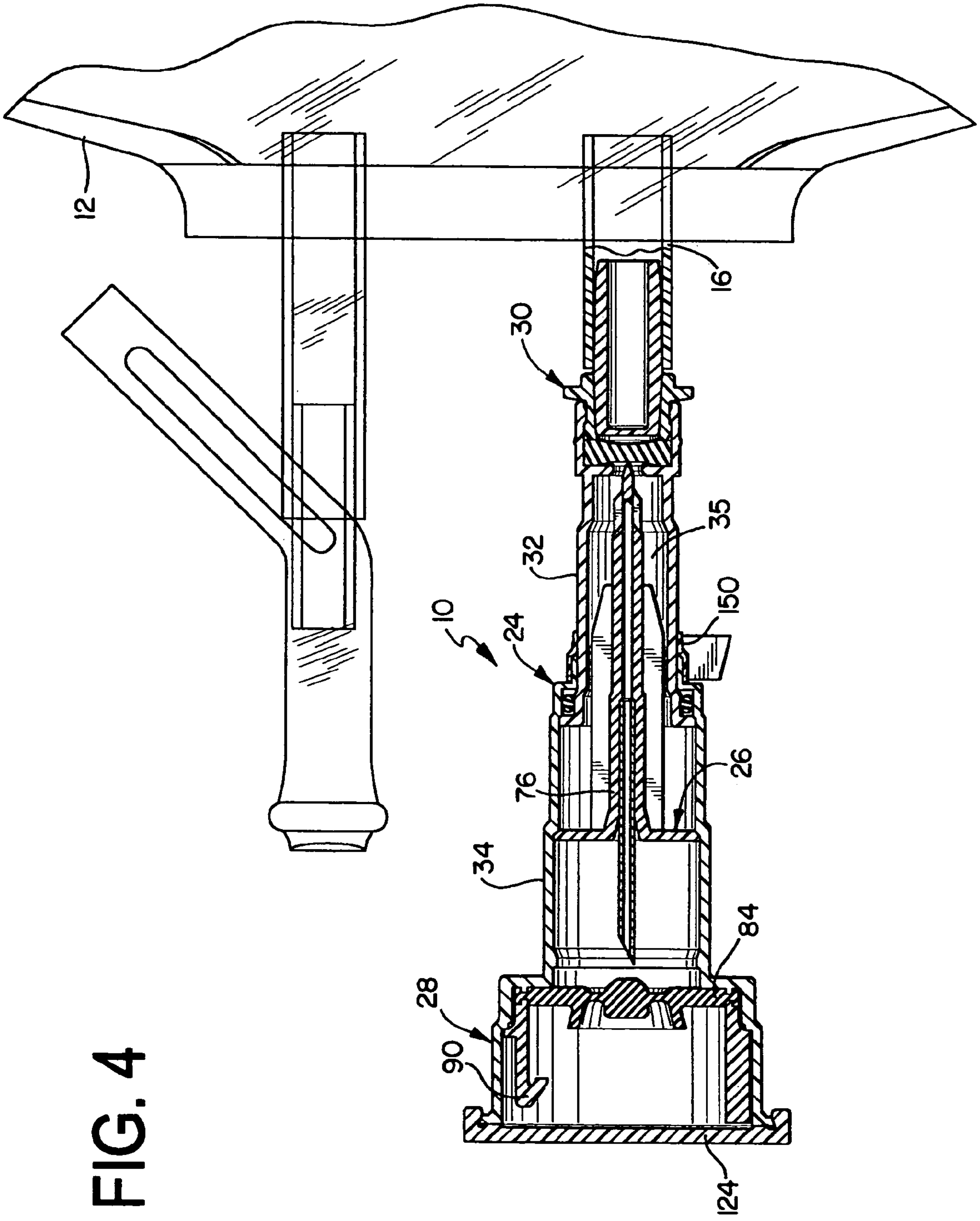
FIG. 4 is a partial cross-sectional view of the connector device of the present invention attached to a flexible container.

Referring to FIGS. 1, 2 and 4, a connector device is disclosed and generally referred to with the reference numeral 10. The device 10 is adapted to place a first container 12, containing a liquid to be used as a diluent, in fluid communication with a second container 14, containing a drug to be diluted or reconstituted.

The first container 12 is typically a flexible bag and is used to contain solutions for a patient to be received intravenously. Flexible containers are typically constructed from two sheets of a polymeric material forming sidewalls that are attached at their outer periphery to define a fluid tight chamber therebetween. In a preferred form of the invention, the fluid container is a coextruded layered structure having a skin layer of a polypropylene and a radio frequency susceptible layer of a polymer blend of 40% by weight polypropylene, 40% by weight of an ultra-low density polyethylene, 10% by weight of a dimer fatty acid polyamide and 10% by weight of a styrene-ethylene-butene-styrene block copolymer. These layered structures are more thoroughly set forth in commonly assigned U.S. Pat. No. 5,686,527 which is incorporated herein by reference and made a part hereof. At one point on the periphery of the container 12 a tubular port 16 is inserted between the sidewalls to provide access to the fluid chamber. A second port 18 is shown for allowing access by a fluid administration set to deliver the reconstituted drug to a patient. However, the first container 12 can be any type of container, including, for example, a syringe barrel, suitable for containing a liquid to be used to reconstitute a drug.

The second container 14 (FIG. 5), which contains a drug to be reconstituted, is a vial. The vial 14 is typically a glass container with a closure member. The closure member may include a rubber stopper 20 and may also have a crimp ring 22. The rubber stopper 20 is inserted in an opening of the vial 14. The rubber stopper 20 is held in place by the crimp ring 22 (FIG. 3), typically made of soft metal such as aluminum, that is crimped around the stopper 20 and the neck of the vial 14 to fixedly attach the stopper 20 to the vial 14. The crimp ring 22 has an aperture to define a target site on the rubber stopper 20. The device 10 can be adapted to accept vials of any size, particularly 20 mm and 13 mm vials. Additionally, the second container 14 can be any container that is adapted to accommodate drugs that require reconstitution.

Figure 7:
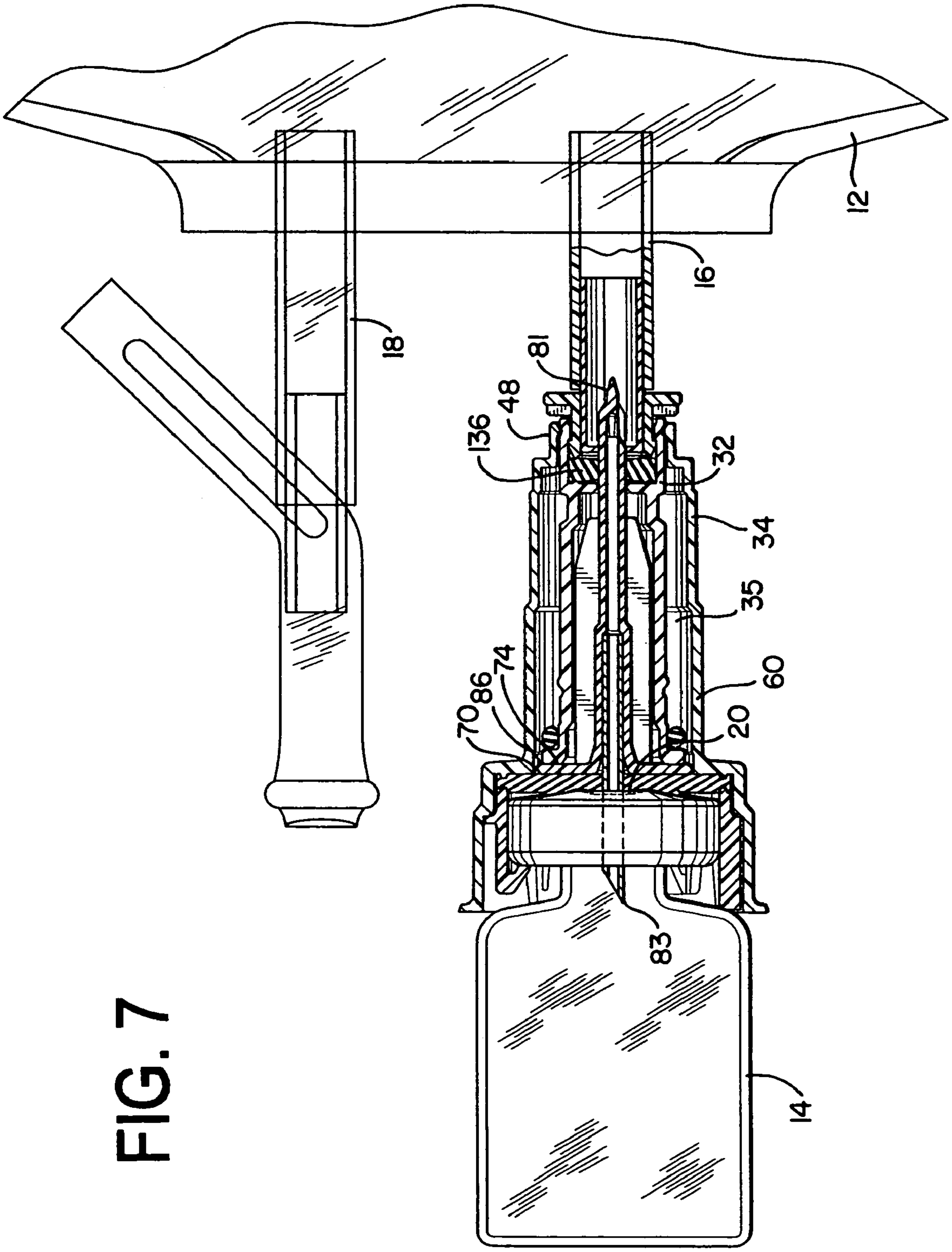
FIG. 7 is a partial cross-sectional view of the connector device in an activated position.
Figure 8:
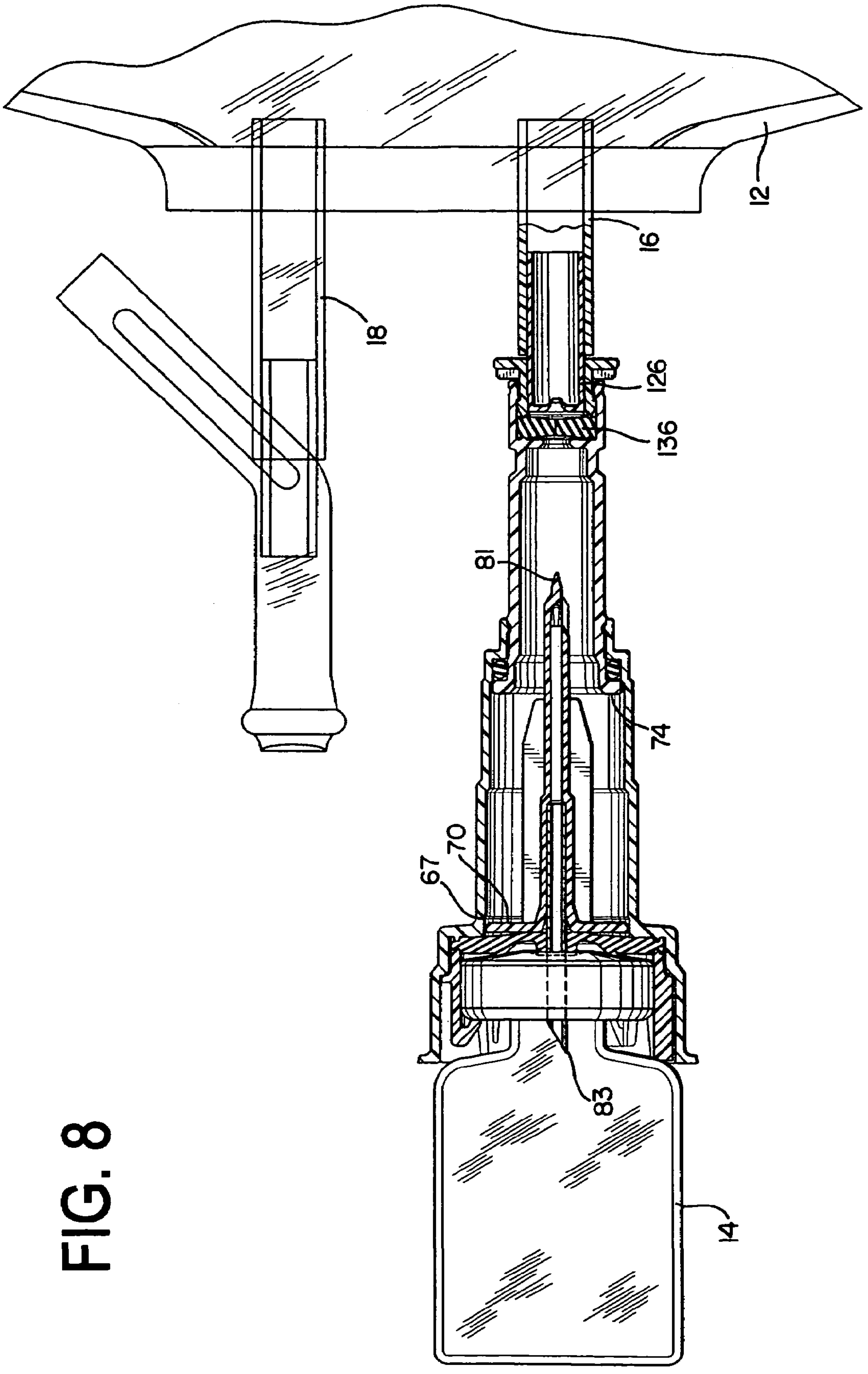
FIG. 8 is a partial cross-sectional view of the connector device in a deactivated position.

The connector 10, as stated above, is adapted to connect to both the flexible bag 12 and the vial 14 and place the contents of the flexible bag 12 and the vial 14 into fluid communication with one another. As shown in FIGS. 1, 2 and 4, the connector 10 generally comprises a sleeve assembly 24, a piercing assembly 26, a gripper assembly 28 and a port connector assembly 30. As described in greater detail below, the gripper assembly 28 and one portion of the sleeve assembly 24 are collectively adapted for axial movement with respect to another portion of the sleeve assembly 24 from an inactivated position (e.g., FIG. 5) to an activated position (FIG. 7). What is meant by the inactivated position is that the containers 12, 14 are not in fluid communication with each other wherein the connector 10 has not been activated. What is meant by the activated position is that the containers 12,14 are placed in fluid communication with each other. What is meant by the deactivated position, or post reconstitution position, is the first container 12 and the second container 14 are not in fluid communication and have been moved from the activated position to the deactivated position (FIG. 8).

As is further shown in FIGS. 1 and 2, the sleeve assembly 24 generally comprises a first sleeve 32 and a second sleeve 34. The first sleeve 32 and second sleeve 34 are mounted for translational motion with respect to one another from the inactivated position to the activated position. In a preferred form of the invention, the first sleeve 32 is slidably mounted within the second sleeve 34. Each sleeve 32,34 has generally cylindrical walls and, collectively, the sleeves 32,34 define a central passageway 35 through the connector 10. The first sleeve 32 may also be referred to as a port adapter sleeve. The second sleeve 34 may also be referred to as a gripper housing sleeve.

Figure 3:
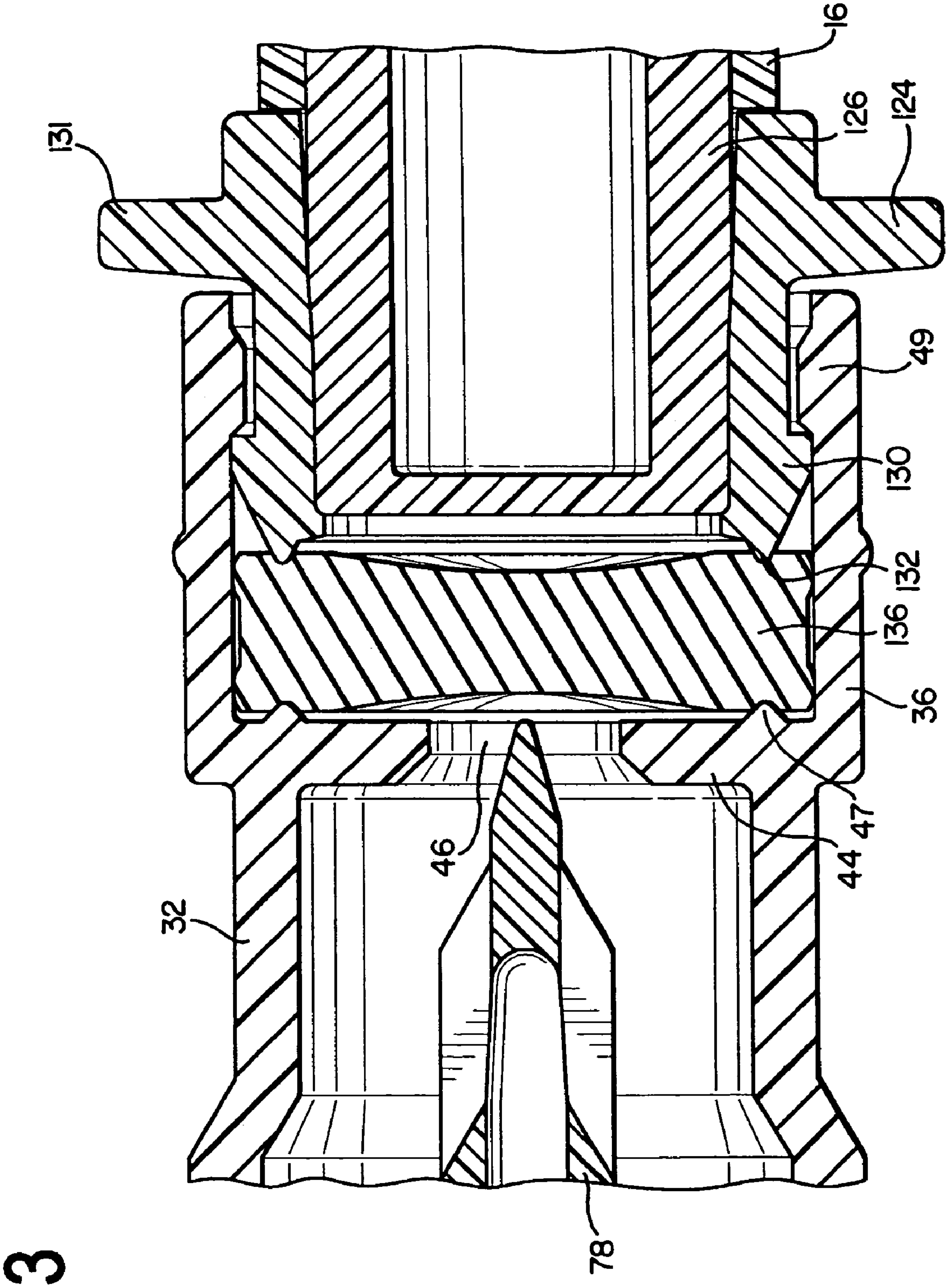
FIG. 3 is an enlarged partial cross-sectional view of a port connector assembly of the connector device of FIG. 1.

The first sleeve 32 has a first end 36 and a second end 38. The first end 36 is adapted to receive and be connected to the port connector 30 as described in greater detail below. The second end 38 of the first sleeve 32 has a partial annular groove 40. The annular groove 40 receives a sealing member 42, preferably in the form of an o-ring. The sealing member 42 provides a seal between the first sleeve 32 and the second sleeve 34 and in a preferred form of the invention is disposed between the first sleeve 32 and the second sleeve 34. Of course, other sealing members such as gaskets, washers and similar devices could be used to achieve a seal between the sleeves 32,34 as is well known in the art and without departing from the present invention. Optionally, the second sleeve 34 could incorporate the annular groove 40 for retaining the sealing member 42. The first sleeve 32 further has a guide 44 at an inner surface of the sleeve 32, intermediate of the first end 36 and the second end 38. The guide 44 has an opening 46 adapted to receive a portion of the piercing assembly 26 during activation. As shown in FIG. 3, a projection 47 extends from the guide 44. An inner surface of the first sleeve 32 has a ramped protrusion 49 extending preferably around a full periphery of the inner surface. The protrusion 49 will cooperate with the port connector assembly 30 as described below.

Additionally, as shown in FIGS. 1 and 2, the first sleeve 32 has a stop surface 51 that cooperates with a stop surface in the form of the second ledge 64 on the second sleeve 34 to prevent the first sleeve 32 from sliding out of the second sleeve 34. The first sleeve 32 also has a stop surface 74 that interfaces with the piercing assembly 26, as will be described in greater detail below. Finally, as shown in FIG. 2, the first sleeve has a detent 39 on its outer surface. The detent 39 cooperates with an end of the second sleeve 34 which maintains the device in the inactivated position. It is understood that the second ledge 64 could be removed if desired and that portion of the second sleeve 34 could be tapered. As can be seen in FIGS. 1 and 2, additional structure in the form of an additional ledge on the second sleeve 34 will still prevent the first sleeve 32 from sliding out of the second sleeve 34.

As shown in FIGS. 1 and 2, the second sleeve 34 also has a first end 48 and a second end 50. The second end 50 of the second sleeve 34 is connected to the gripper assembly 28. In a preferred embodiment, the gripper assembly 28 is an integral portion of the second sleeve 34 although it could be separately attached. It is further understood that the gripper assembly 28, and portions thereof, can be considered as a component of the second sleeve 34. The second sleeve 34 accommodates the piercing assembly 26 within the central passageway 35. The piercing assembly 26 is slidable within the central passageway 35 along an inner surface of the second sleeve 34. Also, as shown in FIG. 2, the second sleeve 34 has a first section 56, a second section 58, and a third section 60. The third section 60 has a larger diameter than the second section 58, and the second section 58 has a larger diameter than the first section 56. At the interface between the second section 58 and the third section 60, a first ledge 62 is formed, and at the interface between the second section 58 and the first section 56, the second ledge 64 is formed. Additionally, the second sleeve 34 has a ramped protuberance 66 on an inner surface of the second sleeve 34. As shown in FIG. 2, the ramped protuberance 66 may begin proximate the ledge 62 and advance towards the second end 50 of the second sleeve 34 wherein it forms a flange 67. The ramped protuberance 66 may also have a shorter construction as shown in FIG. 1. In a preferred embodiment, a plurality of ramped protuberances 66 are utilized and in a most preferred embodiment, four ramped protuberances 66 are spaced around the inner surface of the second sleeve 34. When a semi-resilient disk, in the form of a hub on the piercing assembly 26, as explained below, moves past the ramped protuberance 66, the semi-resilient disk cannot return past the flanges 67. The third section 60 of the second sleeve 34 further has a hub stop surface 69 that maintains the piercing assembly 26 at an initial first position before the device 10 is placed in the activated position. As further shown in FIG. 1, the second sleeve 34 has a plurality of projections 73. The projections 73 are tapered and designed to abut against the hub of the piercing assembly 26 when the device 10 is in the inactivated position. This prevents the piercing assembly from rattling during shipment and maintains the piercing assembly 26 and sealing member 84 in spaced relation in the inactivated position. As explained in greater detail below, the piercing assembly 26 will move past the projections 73 when the device is moved from the inactivated position to the activated position.

As further shown in FIGS. 1 and 2, the piercing assembly 26 generally comprises the hub 70 which supports a piercing member 76. The piercing assembly 26 is generally positioned within the sleeves 32,34 and can be considered as projecting from the sleeves 32,34. The piercing member 76 has a first end 78 that is positioned to pass through the opening 46 of the guide 44 of the first sleeve 32 upon activation. A second end 80 of the piercing member 76 is positioned adjacent the gripper assembly 28 when in the inactivated position. The piercing member 76, such as a cannula or needle, is a rigid, elongate, spiked member at each end 78,80 having a central fluid passage 82 for establishing a fluid flow passage between the first container 12 and the second container 14. The piercing member is positioned outside the sidewalls of the first container 12. Each end 78,80 of the piercing member 76 terminates in a sharp point or an oblique angle or bevel adapted to pierce through closures as will be described below. Alternatively, the piercing member 76 can have other end configurations known in the art. In a preferred embodiment, the piercing member 76 comprises a plastic spike 81 at the end 78 and a metal cannula 83 at the end 80. The spike 81 can be integrally molded with the hub 70. The metal cannula 83 preferably fits within the spike 81 and may be formed from stainless steel. The metal cannula 83 may be adhesively bonded to the hub 70 and plastic spike 81. The plastic spike 81 is positioned to pierce into the port 16 of the flexible container 12. The metal cannula 83 is positioned to pierce the vial 14. The piercing assembly 26 further has a plurality of wings 75 that extend along the piercing member 76. The wings 75 act as guides to assure the plastic spike 81 is properly aligned to pass through the opening 46 of the guide 44 on the first sleeve 32. In a preferred embodiment, four wings 75 are spaced around the piercing member 76. The hub 70 further has a top surface 71.

As further shown in FIGS. 1 and 2, the hub 70, connected to the piercing member 76, is slideable within the central passageway 35 along an inner surface of the second sleeve 34. In a preferred form of the invention, the hub 70 is generally round or disk-shaped. Preferably, the hub 70 has a greater diameter than the diameter of the second section 58 of the central passageway 35 but a slightly smaller diameter than the third section 60. When activating, the piercing member 76 is allowed to move and pierce the stopper 20 of the drug vial 14 and a sealing member 84 (described below) adjacent the second container 14 when the connector 10 moves from the inactivated position to the activated position. The hub 70 has a stop surface 86 that cooperates with the stop surface 74 of the first sleeve 32. When the device 10 is in the inactivated position, the stop surface 86 cooperates with the ledge 62 (FIGS. 2 and 4) on the second sleeve 34, and the top surface 71 of the hub 70 cooperates with the hub stop surface 69, which keeps the piercing assembly 26 in a first position. The hub 70 further has an annular outer surface 88 that slides along the inner surface of the second sleeve 34 and specifically along the ramped protrusions 66. The metal cannula 83 and plastic spike 81 may have a lubricant applied thereto to help facilitate insertion into the respective containers 12, 14.

FIGS. 1 and 2 further show the gripper assembly 28 attached to the second sleeve 34. As discussed, in the preferred embodiment, the gripper assembly 28, or portions thereof, is integrally attached to the second end 50 of the second sleeve 34. The gripper assembly 28 could also be considered as part of the second sleeve 34. The gripper assembly 28 serves as a second attaching member to connect the vial 14 to the device 10. The gripper assembly 28 generally includes a wall portion 90, a base 91, a finger assembly 92, and a sealing member 84. The finger assembly 92 may also be referred to as a gripper ring. The gripper assembly 28 serves as an attaching member that is adapted to attach the device 10 to the second container or drug vial 14. The gripper assembly 28 has a central opening 96. The wall portion 90 is preferably annular and forms a cup-like shape in cooperation with the base 91. The wall portion 90 is preferably continuous and solid. It is understood that the gripper assembly 28 could simply include a finger structure, integral with or separately attached to the second sleeve 34, that is dimensioned to attach to a second container 14. It is further understood that the gripper assembly 28 can take various forms that serve to attach to the second container 14.

Referring again to FIGS. 1 and 2, the wall portion 90 supports means for fixedly attaching the second container or drug vial 14 to the gripper assembly 28. The means shown are a plurality of segmented fingers that cooperatively form the finger assembly 92. The finger assembly 92 comprises a plurality of alternating segmented fingers 98*a*, 98*b* that are connected at their bottom portions. The wall portion 90 has a ledge 97. The bottom portions of the fingers 98 have corresponding structure to the ledge 97. The finger assembly 92 is bonded to the wall portion 90 proximal this area.

The fingers 98*a* are spaced inwardly from the wall portion 90 to allow the fingers 98*a* to flex when a drug vial 14 is inserted into the gripper assembly 28. The fingers 98*b* have a rear portion contacting the wall portion 90 and generally do not flex as will be described in greater detail below. The fingers 98*a*, 98*b* are generally trapezoidal in shape and are separated by gaps to define a vial receiving chamber that corresponds to the central opening 96 of the gripper assembly 28 for receiving a top of the vial 14. Though the present device utilizes six fingers 98*a*, 98*b*, it can be appreciated by one of ordinary skill in the art that more or fewer fingers could be utilized without departing from the scope of the present invention. For example, eight fingers could be used.

What is meant by "fixedly attached" is that in order to remove the vial 14 from the connector 10, one would have to exert a force considerably in excess of that normally used to operate the device 10. Such a force likely would break, detach or noticeably deform one or more of the segmented fingers 98 or other portions of the connector 10 in the process.

As further shown in FIG. 1, three of the fingers 98*a* include radially inwardly tapering resilient tabs 104, from a distal end to a proximal end, past which the medical professional must urge a neck of the drug vial 14 in order to connect it to the gripper assembly 28. The tabs 104 are configured such that a space 105 is maintained between the tab 104 and the finger 98*a*. It is appreciated that the tabs 104 are capable of flexing to accommodate varying diameter vial closures. Preferably, the distal end of the fingers 98 have a radiused end that is smooth to avoid cutting the medical personnel handling the connector 10. The tabs 104 could also be formed, however, as solid bumps without departing from the invention.

As also shown in FIG. 1, the remaining fingers 98*b* (one shown) have axially extending, standing ribs 106 extending along an inner surface of the fingers 98*b*. The standing ribs 106 extend proximate a bottom portion of the finger but do not contact the base 91 of the gripper assembly 28. The ribs 106 are spaced from the base by the sealing member 84. In a preferred form, the standing ribs 106 assist in aligning the vial 14 with the vial receiving chamber during insertion. The standing ribs 106 are capable of indenting one or more sidewall portions of the metal crimp ring 22 of the vial 14 in order to inhibit the vial 14 from rotating. While one standing rib 106 is shown on each finger 98*b*, a pair of standing ribs 106 on each finger 98*b* could also be utilized to enhance the prevention of rotation of the vial 14. The fingers 98*b* have a post 107 on a rear portion that contacts the wall portion 90. Thus, when the vial 14 is inserted into the gripper assembly 28, the fingers 98*b* flex very little, if any, while the fingers 98*a* do flex as the fingers 98*a* are spaced inward from the wall portion 90. It is desirable for the fingers 98*b* not to flex in order to maximize the ability of the standing ribs 106 to indent the side of the crimp ring 22 and prevent rotation of the vial 14.

As further shown in FIG. 1, the fingers 98*b* having the standing ribs 106 are slightly taller than the fingers 98*a* with the tabs 104. The fingers 98*b* have a flat lead-in section 99. The flat lead-in section 99 helps to properly align the vial 14 as it is inserted into the gripper assembly 28. Because the fingers 98*b* are taller than the fingers 98*a*, the vial 14 is aligned by the lead-in sections 99 and then contacts the tabs 104 as the vial 14 is further inserted into the gripper assembly 28.

While three fingers 98*a* with resilient tabs 104 and three fingers 98*b* with standing ribs 106 is preferred, providing more or fewer fingers with resilient tabs 104 or standing ribs 106 would not depart from the scope of the invention. It is also preferable that the fingers 98*a* with the tabs 104 and the fingers 98*b* with the standing ribs 106 are disposed in alternating order. It may also be desirable to place a flexible restraining member, such as shrink wrap or the like, around the fingers 98*a*, 98*b* to assist in gripping the vial 14.

The wall portion 90 further has a first annular rim 108 extending from the base 91. The finger assembly 92 has a bottom portion 93, or base portion, having a second annular rim 110 extending therefrom and towards the first annular rim 108. The second annular rim 110 is coradial with the first annular rim 103 and is longitudinally displaced therefrom. The rims 108, 110 cooperate with the sealing member 84 to be described in greater detail below. In other embodiments disclosed herein, the base portion 93 of the finger assembly 92 could be substantially planar to cooperate with a substantially planar surface of a respective sealing member 84. The finger assembly 92 is ultrasonically welded to the inner surface of the wall portion 90. In this manner, the sealing member 84 is positioned between the base 91 of the wall portion 90 and the bottom portion 93 of the finger assembly 92 wherein the sealing member 84 hermetically seals the central passageway 35 and the piercing member 26 disposed therein.

Figure 5:
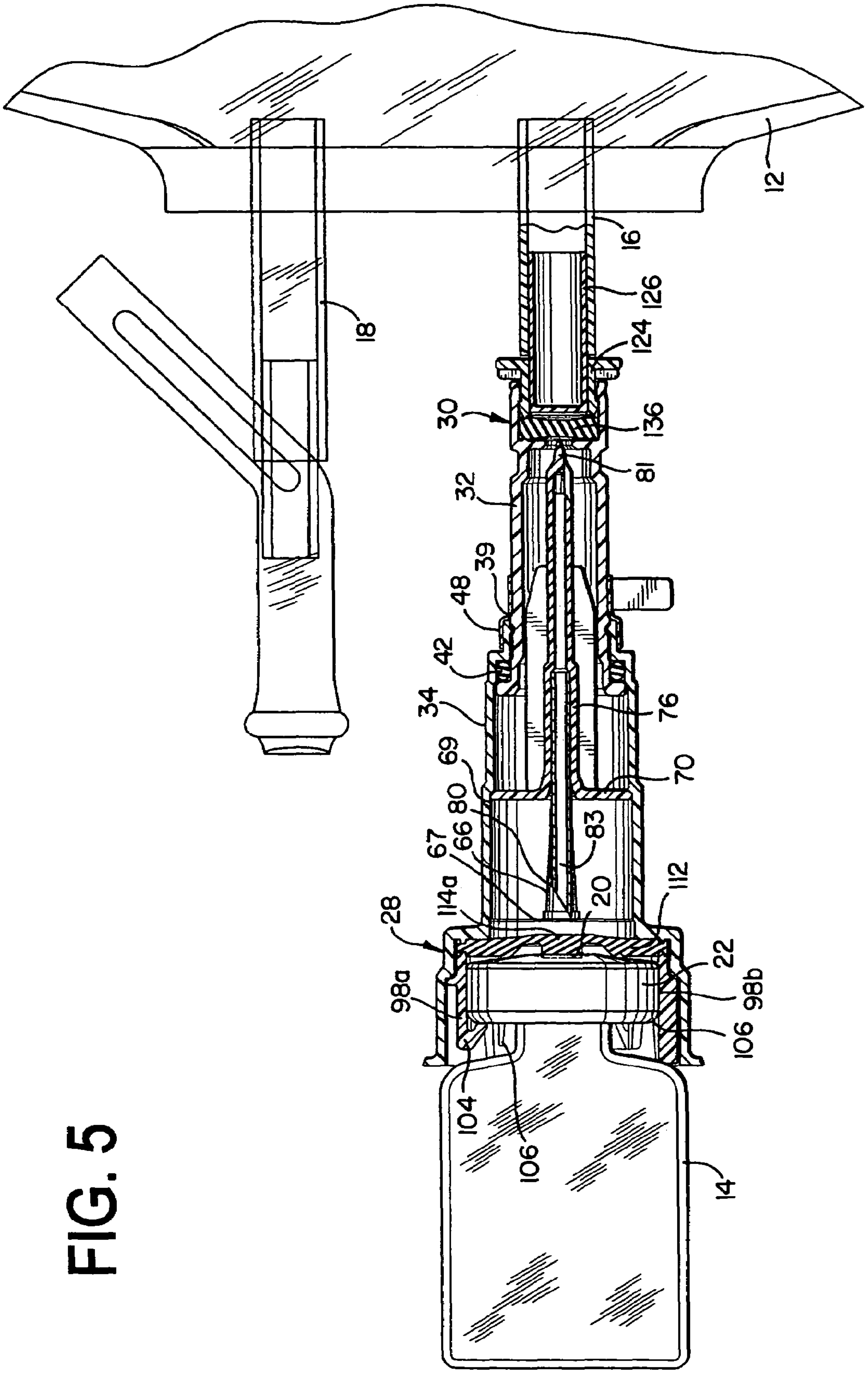
FIG. 5 is a partial cross-sectional view of the connector device of the present invention having a drug vial fixedly secured to the connector device, the connector device being in an inactivated position.

As further shown in FIGS. 1 and 2, the sealing member 84, sometimes referred to as a septum 84, or vial septum 84, is positioned within the gripper assembly 28. In a preferred embodiment, the sealing member 84 has a base 111 and an annular ridge 112. The base has first and second surfaces. The base is preferably disk-shaped. The annular ridge 112 extends axially from the disk and towards the top of the vial 14. The annular ridge 112 is dimensioned to tightly and sealingly fit over the rubber stopper 20 of the vial 14 to prevent leakage from the vial 14. In a preferred embodiment, the annular ridge 112 tapers axially-outwardly. In addition, the annular ridge 112 of the sealing member 84 is capable of deforming to accommodate dimensional variations in a height of a closure of the second container. The sealing member 84 can be pre-slit at a central location corresponding to the end 80 of the piercing member 76. In one preferred embodiment, the sealing member 84 has a center hub 114 having a thickened cross-section as shown in FIG. 1. The center hub 114 is positioned to be pierced by the piercing member 76 during activation of the device 10. In one preferred embodiment, the piercing member 76 is buried into the thickened center hub 114, without passing through the hub 114, as the plastic spike 83 pierces into the container 12. FIG. 5 shows the sealing member 84 having a thickened center hub 114*a* that is slightly thinner than the center hub 114 shown in FIG. 1. The disk-shaped sealing member 84 has a web 85 of thinner cross-section than the center hub 114. The web 85 assists the hub 114 in flexing to accommodate dimensional variations in the vial 14. The annular ridge 112 is positioned circumjacent the center hub 114 and the web 85. A first annular groove 113 is positioned at an outer periphery of the sealing member 84 on a first side of the sealing member 84. A second annular groove 115 is positioned on a second side of the sealing member 84 generally opposite annular groove 115. When the device is assembled, the first annular groove 113 receives the first annular rim 108 and the second annular groove 115 receives the second annular rim 110 wherein the sealing member 84 is sandwiched between the base 91 and the bottom portion 93 of the finger assembly 92. In this configuration, the sealing member 84 hermetically seals the passageway 35 and sealing member 76 at the second end 50 of the second sleeve 34. In one form, the sealing member 84 can be sized slightly larger such that when the annular grooves 113, 115 receive the annular rims 108, 110, the sealing member 84 is subjected to a radial compressive force. This assists the sealing member 84 is accounting for dimensional variations of vials 14 that are inserted into the gripper assembly 28. Also, the sealing member 84 can be lubricated, which lubricates the piercing member 76 allowing it to enter the drug vial 14 more easily. The sealing member 84 is preferably made from silicone rubber.

In an alternative embodiment, the sealing member 84 could have a central opening. The central opening receives the piercing member 76 when the connector 10 is moved from its inactivated position to the activated position. The central opening would also allow for steam sterilization past the sealing member 84.

As also shown in FIG. 1 and 2, the wall portion 90 has a lip 122 at its outer periphery. An end cap, or flip cap 124 is dimensioned to snap over the lip 122 to seal the gripper assembly 28 before a vial 14 is inserted into the gripper assembly 28. No orientation of the end cap 124 is required. The lip 122 is preferably integrally molded with the wall portion 90. The end cap 124 is preferably made from plastic or other suitable material. The end cap 124 provides a hermetic seal between the exterior of the device 10 and the central opening 96. A tape strip (not shown) could be stretched across the end cap 124 and attached to outer surfaces of the wall portion 90 as a tamper evident feature.

Alternatively, a seal material can be releasably secured to the wall portion 90 such as by heat sealing wherein the material can be peeled away by pulling a tab formed on the seal material. The wall portion 90 provides for a solid surface to mount the seal material therefore hermetically sealing the connector 10. The seal material can be made of aluminum foil, or of polymeric based material such as TYVEK®, and more preferably TYVEK® grade 1073B, or spun paper or other material that is capable of being peelably attached to the wall portion 90 and capable of providing a barrier to the ingress of contaminants. It is also contemplated that sealing can be accomplished through induction welding or other sealing techniques.

FIGS. 1-3 show the port connector assembly 30 of the device 10. The port connector assembly 30 serves as a first attaching member to connect the first container 12 to the device 10. It is understood that the port connector assembly 30 could be considered as part of, or associated with, the first sleeve 32. The first sleeve 32 could also be configured to be directly attached to the first container 12. The port connector assembly 30 generally includes a first attaching element 124, generally in the form of a port snap 124, and a second attaching element 126, generally in the form of a container sleeve 126 or membrane tube 126, and also a port septum 136. The container sleeve 126 is generally cylindrical and has one end closed by a membrane 128. The port snap 124 is also generally cylindrical and dimensioned to receive the container sleeve 126. The port snap 124 has a flange 130 extending around its outer surface. A distal end of the port snap 124 has a generally circular, tapered finger 132 extending therefrom. The port snap 124 further has a circular ledge 131 extending radially outwardly from the port snap 124. The ledge 131 is sized to be engaged by fingers of a user during the activation process as described in greater detail below.

The container sleeve 126 is inserted into the port snap 124 and connected thereto preferably by solvent bonding an outer surface of the sleeve 126 to an inner surface of the port snap 124, thus forming a port connector sub-assembly. The membrane 128 of the sleeve 126 is positioned at the flange end of the port snap 124. As shown in FIGS. 1-3, before connecting the port connector assembly 30 to the second end 36 of the first sleeve 32, the port septum 136, a second sealing member, preferably in the form of a rubber septum, is inserted into the second end 36 of the first sleeve 32. The second sealing member 136 is positioned adjacent the guide 44 wherein the projection 47 indents the second sealing member 136. If desired, the port septum 136 could be pre-slit. The second sealing member 136 prevents "drip-back" after the deactivation procedure as will be described in greater detail below. The port snap 124 is then inserted and urged into the first sleeve 32 wherein the flange 130 passes by the protrusion 49 of the first sleeve 32. The resiliency of the materials allow the flange 130 to snap back after passing by the protrusion 49 wherein a tight interference fit is formed between the port connector 30 and the first sleeve 32. Once inserted, the tapered finger 132 indents the second sealing member 136, thus sandwiching the second sealing member 136 between the guide 44 and the port snap 124.

As shown in FIG. 4, the port connector assembly 30 is also connected to the first container 12 wherein the outer surface of the container sleeve 126 is connected to an inside surface of the container port 16, preferably by solvent boding.

In one preferred embodiment, the overall connection between the first container 12 and first sleeve 31 via the port connector assembly 30 is performed using an electron-beam process as disclosed in commonly-assigned U.S. patent application. Ser. No. 09/294,964 entitled "Method and Apparatus For Manipulating Pre-Sterilized Components In An Active Sterile Field," which is expressly incorporated herein by reference. Other methods of connection are also possible such as solvent bonding.

It is understood that in a preferred embodiment, the protrusion 49 and flange 130 are formed around a full periphery of the first sleeve 32 and port snap 124 respectively. These structures can also be in the form of an interrupted annular ridge, a plurality of bumps or even a single bump.

Typically, the connector 10 is connected to the flexible bag 12 prior to shipping. It will be appreciated by one of ordinary skill in the art, however, that the connector 10 could be connected to the first container 12 at different times.

In another embodiment, it is understood that the flexible bag 12 can be pre-attached to a portion of the port connector assembly 30 wherein further connection to the connector 10 is performed in a separate manufacturing process. This separate manufacturing process may be performed at a separate time. For example, in a first process, the port snap 126 is solvent bonded to the membrane tube 126. The flexible bag 12 is filled with the appropriate diluent. The membrane tube 126, with attached port snap 124, is then solvent bonded to the container port 16 of the flexible bag 12. It is understood that the flexible container 12 is then sealed because the membrane 128 of the membrane tube 126. This flexible bag subassembly can then be attached to the first sleeve 32, after the port septum 136 is inserted into the first sleeve 32, in a separate manufacturing process. This attachment may preferably be performed using the electron-beam process as described above.

Referring to FIG. 1, the device 10 can optionally include a member such as tamper-evident strip 150, which is preferably made from adhesive material. The tamper-evident strip 150 can be attached at a juncture between the first sleeve 32 and the second sleeve 34 and over the detent 39. The attachment of the tamper-evident strip 150 alone could be configured to prevent premature movement or activation of the sleeves 32,34. Medical personnel must remove the strip 150 in order for the first sleeve 32 and the second sleeve 34 to be capable of relative axial movement. Optionally, the tamper evident strip 150 could be capable of indicating the first and second sleeves 32,34 have been moved axially with respect to one another, rather than preventing such movement, by becoming damaged upon such movement. The tamper-evident strip 150 can also include a flap 152 for removing the tamper evident strip 150. In this manner, the tamper evident strip 150 can indicate to a medical professional that someone has used or tampered with the device 10 by the fact that the tamper evident strip 150 is missing or damaged. The tamper evident strip 150 can take alternative forms as shown in FIG. 21.

FIGS. 1, 2 and 4 show the connector 10 in its inactivated position where the connector 10 is in its most elongated state. In this inactivated position, the stop surface 51 of the first sleeve 32 abuts the stop surface 64 of the second sleeve 34. The hub 70 is maintained between the hub stop surface 69 and the ledge 62. FIGS. 4-7 disclose the activation process for the connector 10. FIG. 4 shows the device 10 connected to the flexible container 12. As shown in FIG. 5, the end cap 124 is first flipped off the gripper assembly 28. The vial 14 is then inserted into the gripper assembly 28 wherein the fingers 98*a* flex towards the wall portion 90 until the vial 14 passes by the tabs 104 wherein the neck of the vial 14 is positioned between the tabs 104 and the sealing member 84. The standing ribs 106 on the fingers 98*b* indent a side portion of the crimp ring 22 on the vial 14. Thus, the vial 14 is fixedly attached to the connector 10. As further shown in FIG. 5, the annular ridge 112 of the sealing member 84 forms a fluid tight seal over the top of the vial 14. Thus, a vial 14 can be selectively docked to the connector 10 without piercing the stopper 20 of the vial 14. As further shown in FIG. 5, the second end 80 of the piercing member 76 is positioned close to the center hub 114 of the sealing member 84. This reduces the stroke length or distance the piercing member 76 must travel to pierce the sealing member 84 and the stopper 20 of the drug vial 14.

Figure 6:
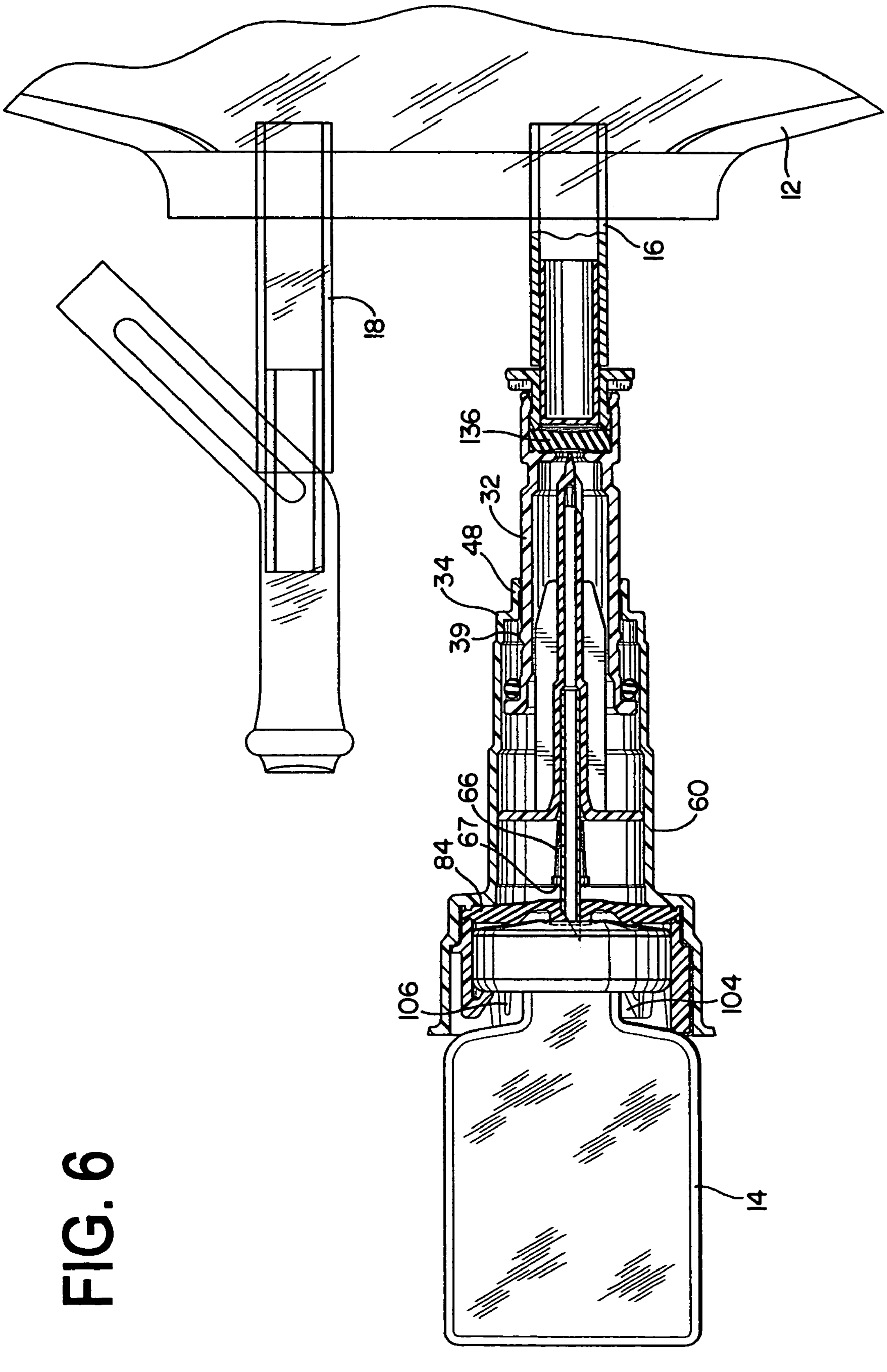
FIG. 6 is a partial cross-sectional view of the connector device shown in FIG. 5 wherein the connector device is in the initial stages of an activation process.

FIG. 6 shows the connector device 10 as the activation process commences. To activate, the tamper-evident strip 150 is first peeled away from the sleeves 32,34. The vial 14 in the gripper assembly 28, along with the second sleeve 34, are moved axially towards the flexible container 12. Adequate force must be applied so that the first end 48 of the second sleeve 34 moves past the detent 39 on the first sleeve 32. As the second sleeve 34 moves along the first sleeve 32, the plastic spike 81 will engage the second sealing member 136. Because of the materials used, the plastic spike 81 will not yet pierce through the second sealing member 136. The friction associated with this engagement will cause the hub 70 to move along the second sleeve 34 wherein the metal cannula 83 will pierce the sealing member 84 and closure of the vial 14. As shown in FIG. 7, as the second sleeve 34 further moves along the first sleeve 32, the stop surface 74 on the first sleeve 32 moves towards and engages the stop surface 86 of the hub 70 on the piercing assembly 76. The hub 70 thus moves along the third section 60 of the second sleeve 34 wherein the hub 70 rides along the ramped protuberances 66 and eventually passes over the flanges 67. This movement forces the metal cannula 83 at the second end 80 of the piercing assembly 76 to pierce completely through the center hub 114 and stopper 22 and thus into the vial 14. The second end 80 of the piercing member 76 now experiences greater friction as it penetrates the stopper 22 of the vial 14. This friction causes the plastic spike 81 at the first end 78 of the piercing member 76 to advance towards the flexible container 12. The plastic spike 81 pierces through the second sealing member 136 and the membrane 128.

As also shown in FIG. 7, the sleeves 32,34 translate axially wherein the hub 70 advances to against the sealing member 84; also, the first end 48 of the second sleeve 34 proceeds to the first end 36 of the first sleeve 32. This position (FIG. 7) represents the activated position. In the activated position, the metal cannula 83 at the second end 80 of the piercing member 76 is pierced through the stopper 20 of the vial 14, and the plastic spike 81 at the first end 78 of the piercing member 76 is pierced through the second sealing member 136. Thus, fluid communication is established between the flexible bag 12 and the vial 14 through the central fluid passageway 82 of the piercing member 76.

It is understood that when the connector 10 is in the inactivated position, the central passageway 35 is sealed in a substantially air-tight fashion at one end by the sealing member 84, at an opposite end by the second sealing member 136 and at the interface between the sleeves 32,34 by the sealing member 42. As the vial 14 and second sleeve 34 advance towards the flexible container 12 during the activation process, the volume of the central passageway 35 necessarily decreases thus pressurizing the air located in the central passageway 35. This pressurized air must be relieved before the connector 10 reaches the final activated position. Accordingly, when the o-ring 42 moves past the first section 56 of the second sleeve 34 to the larger diameter of the second section 58 of the second sleeve 34, the sealing member 42 no longer contacts the inner surface of the second sleeve 34 (FIG. 6) thus allowing the pressurized air to be relieved through the junction of the sleeves 32,34.

In the activated position shown in FIG. 7, the diluent contained in the flexible container 12 can pass through the piercing member 76 to reconstitute the drug contained in the vial 14. Once the drug is reconstituted and the resulting mixture passes completely through the piercing member 76 and into the flexible container 12, the drug vial 14 and second sleeve 34 can be pulled back away from the flexible container 12. As shown in FIG. 8, when the second sleeve 34 is pulled back, the piercing assembly 26 is retained in position by the flange 67 of the ramped protuberance 66. The stop surface 74 of the first sleeve 32, however, does not contact the ramped protuberance 66 and can be retracted. The metal cannula 83 of the piercing member 76 remains in the closure of the vial 14 and the plastic spike 81 of the piercing member 76 is pulled past the membrane 128 and the second sealing member 136 (FIG. 8). This position is referred to as the deactivated position, or post reconstitution position. The second sealing member 136 is resilient and forms a seal once the plastic spike 81 passes by, thus preventing any of the resulting mixture from dripping back into the drug vial 14 or passing into the passageway 35 of the sleeve assembly 24.

The resulting mixture can then be delivered to a patient through appropriate tubing sets (not shown) attached to the second port 18 on the flexible container 12.

Figure 9:
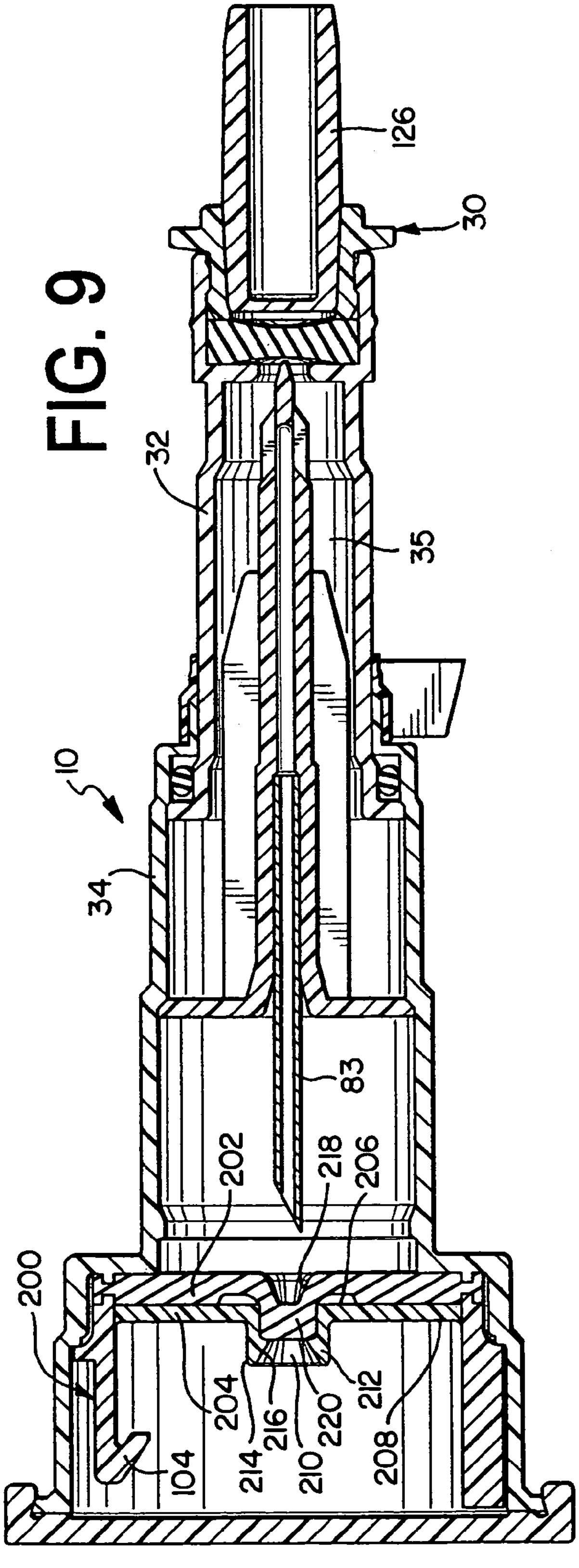
FIG. 9 is a cross-sectional elevation view of the connector device of the present invention having an alternative vial connecting device and sealing member.
Figure 10:
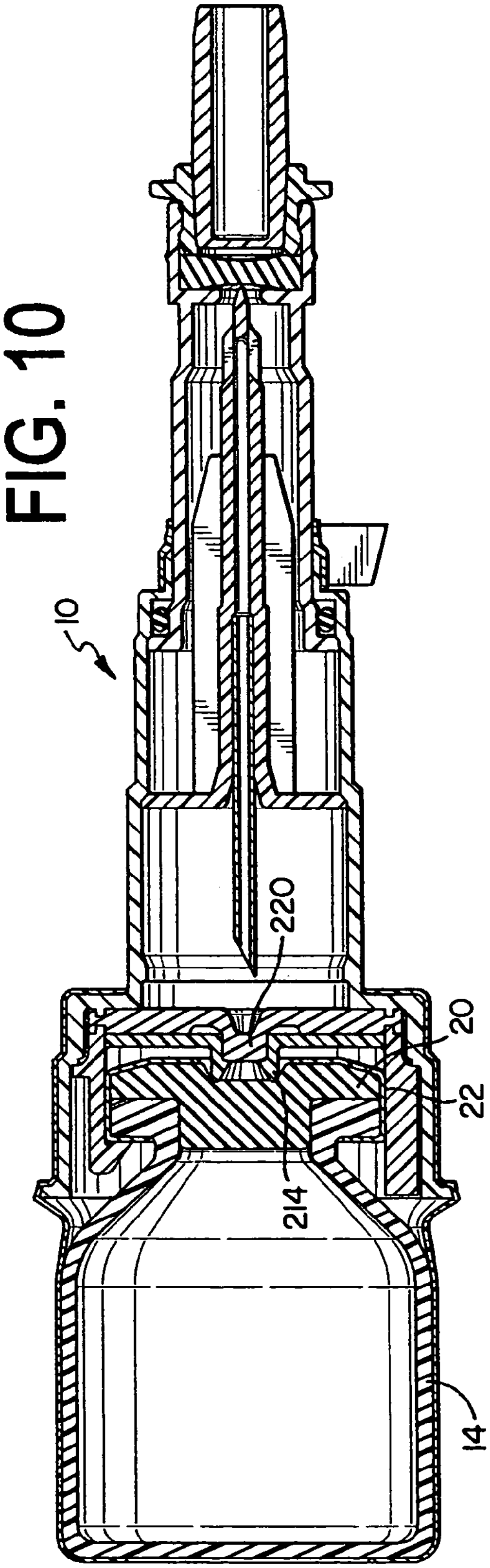
FIG. 10 is a cross-sectional view of the connector device shown in FIG. 9 having a drug vial fixedly secured to the connector device, the connector device being in an inactivated position.

FIGS. 9 and 10 disclose another embodiment of the connector device 10 having an alternative vial connecting structure. Similar elements will be designated with the same reference numerals. As shown in FIG. 9, the connector device 10 utilizes an alternative finger assembly 92, generally designated with the reference numeral 200, as well as an alternative sealing member 84, or septum, generally designated with the reference numeral 202. The finger assembly 200 has a disk-shaped base or panel 204 at a bottom portion of the fingers 98. The panel 204 has a first side 206 and a second side 208. The panel 204 further has a center opening 210 extending through the panel 204 from the first side 206 to the second side 208. The panel 204 also has an annular ring 212 extending from the second side 208 of the disk. The annular ring 212 has a rounded end surface 214 that is generally blunt. The annular ring 212 further has an inner lip 216. The panel 204 and annular ring 212 are preferably integrally molded with the finger assembly 92 of a rigid material. In a most preferred embodiment, the annular ring 212 is made from PVC material. The septum 202 is similar to the septum 84 but has a conical-shaped central portion 218 that supports a center plug 220. The septum 202 is supported in the connector device 10 similar the previously-described septum 84. The septum 202 is positioned between the base 91 and a bottom portion of the finger assembly 92 wherein the panel 204 extends over the septum 202. The center plug 220 fits into the center opening 210 and abuts against the inner lip 216.

FIG. 10 shows the connector device 10 having the vial 14 fixedly secured to the gripper assembly 28. As previously discussed, the vial 14 has a crimp ring 22 that has an aperture or circular opening on the rubber stopper 20 that plugs the opening of the vial 14. The opening defines a target site of the rubber stopper 20. As shown in FIG. 10, the annular ring 212 is sized such that it fits within the opening of the crimp ring 22. The annular ring 212 does not contact the crimp ring 22. As discussed, the annular ring 212 is rigid and has a hardness greater than the rubber stopper 20. The annular ring 212 deforms the rubber stopper 20 but does not cut or pierce into the stopper 20. The annular ring 212 sealingly engages the rubber stopper 20 to form a fluid tight seal against the closure member or stopper 20. Once sealed, the metal cannula 83 pierces through the center plug 220 passing through the annular ring 212 and stopper 20 and into the vial 14. In a preferred embodiment, the annular ring 212 is integrally connected to the panel 204 and finger assembly 92. Alternatively, the septum 202 could be modified to support the rigid annular ring 212.

Figure 11:
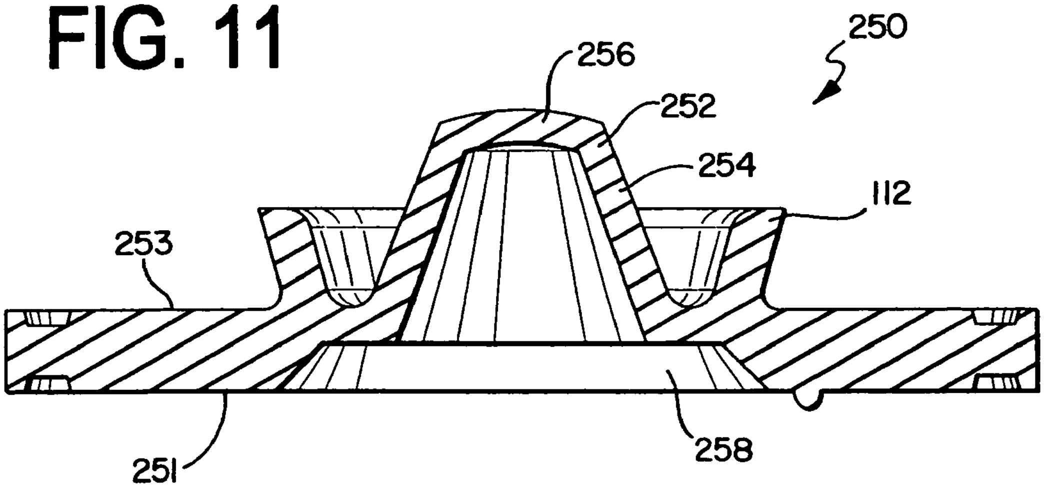
FIG. 11 is a cross-sectional view of an alternative embodiment of the sealing member used in the connector device.
Figure 12:
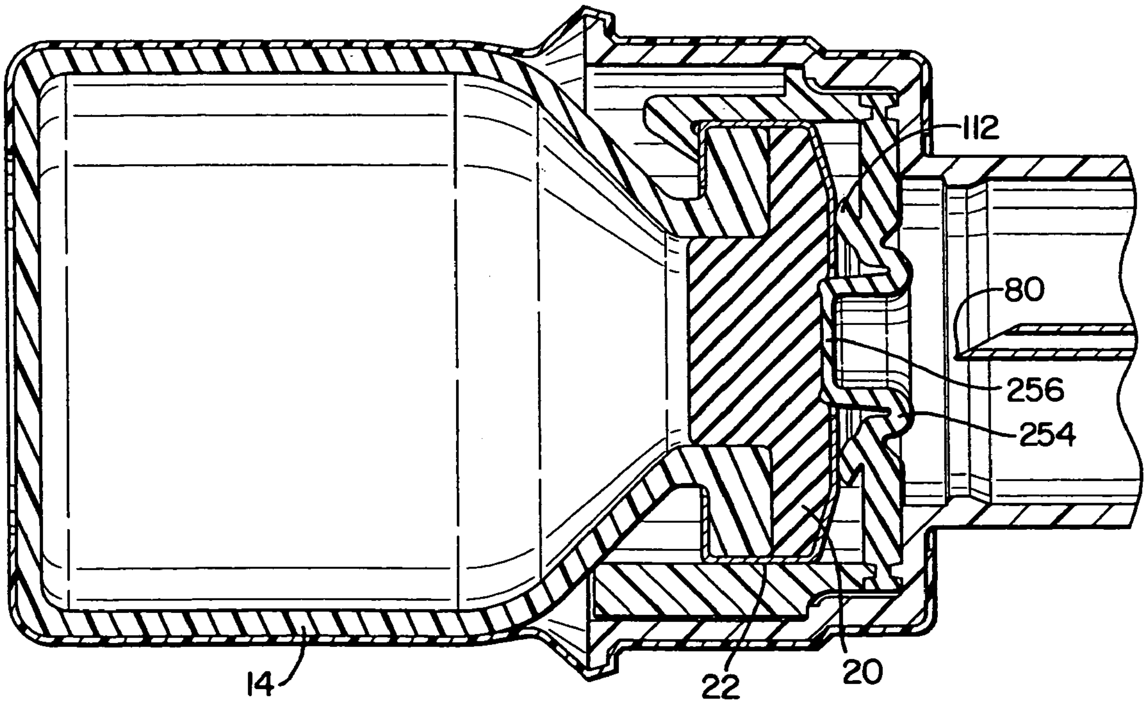
FIG. 12 is a partial cross-sectional view of the connector device of the present invention utilizing the sealing member of FIG. 11 and having a drug vial fixedly secured to the connector device, the connector device being in an inactivated position.

FIGS. 11 and 12 disclose another embodiment of the sealing member 84, used with the connector device 10, generally designated by the reference numeral 250. Similar elements will be referred to with identical reference numerals. Similar to the sealing member 84 discussed above, the sealing member 250 has a disk-shaped base having a first surface 251 and a second surface 253. The annular ridge 112 extends axially from the second surface 253 of the disk and towards the top of the vial 14. The sealing member 250 further has a cap 252 concentrically disposed within the annular ridge 112 and that also extends from the second surface 253 of the disk. The cap 252 is generally in the form of a conical frustum. The cap 252 has a frustoconical sidewall 254 connected to a top wall 256. In a preferred embodiment, the top wall 256 has a slight concave shape. The frustoconical sidewall 254 extends from the disk towards the vial 14 further than the annular ridge 112. The sealing member 250 has a recessed portion 258 on an underside surface adjacent to a bottom portion of the sidewall 254.

FIG. 12 discloses the sealing member 250 connected in the connector device 10 similar to the sealing member 84 as well as a vial 14 connected to the gripper assembly 28. As shown, the top wall 256 of the cap 252 deflects into a generally planar position to tightly and sealingly fit against the rubber stopper 20 of the vial 14. If desired, the rubber stopper 20 could be molded with a depression to accommodate the top wall 256. The frustoconical sidewall 254 bows outwardly. Thus, the cap 252 does not deform the rubber stopper 20. The annular ridge 112 tightly and sealingly fits over the crimp ring 22 of the vial 14. The recessed portion 258 accommodates the deflection of the cap 252 against the vial 14. Thus, the sealing member 250 provides a dual fluid tight seal against the closure member of the vial 14. The cap 252 sealingly fits against the target site of the rubber stopper 20 and the annular ridge 112 sealingly fits against an outer portion of the rubber stopper 20. The sealing member 250 provides even greater sealing capabilities by providing a dual-seal structure. Like the sealing member 84, the sealing member 250 can also be preferably made from Silicone PL-S146.

In both the sealing structures disclosed in FIGS. 9-12, a seal is provided directly against the rubber stopper 20. The annular ring 212 and cap 252 provide a seal against the target site of the rubber stopper 20. In the unlikely event that the rubber stopper became contaminated in an area underneath the crimp ring 22, sterility would not be comprised since the annular ring 212 and cap 252 directly seal against the rubber stopper 20.

FIGS. 13-18 disclose another embodiment of the sealing member 84, used with the connector device 10, generally designated by the reference numeral 300. As shown, the sealing member 300 generally includes a base 302, a diaphragm 304, and an annular ridge 306.

Figure 13:
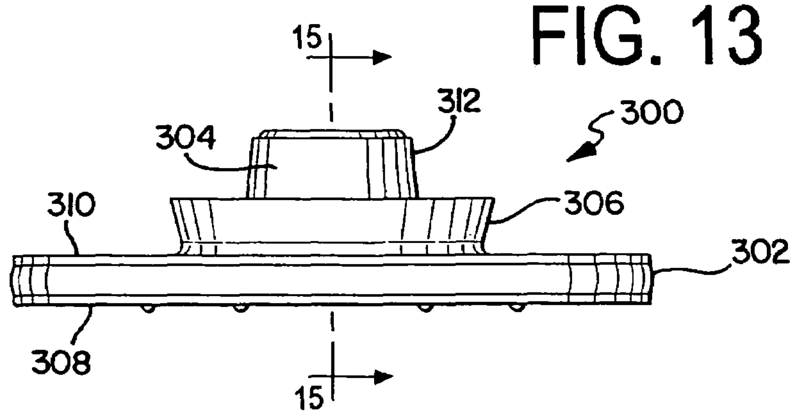
FIG. 13 is a front elevation view of another embodiment of the sealing member used in the connector device of the present invention.
Figure 14:
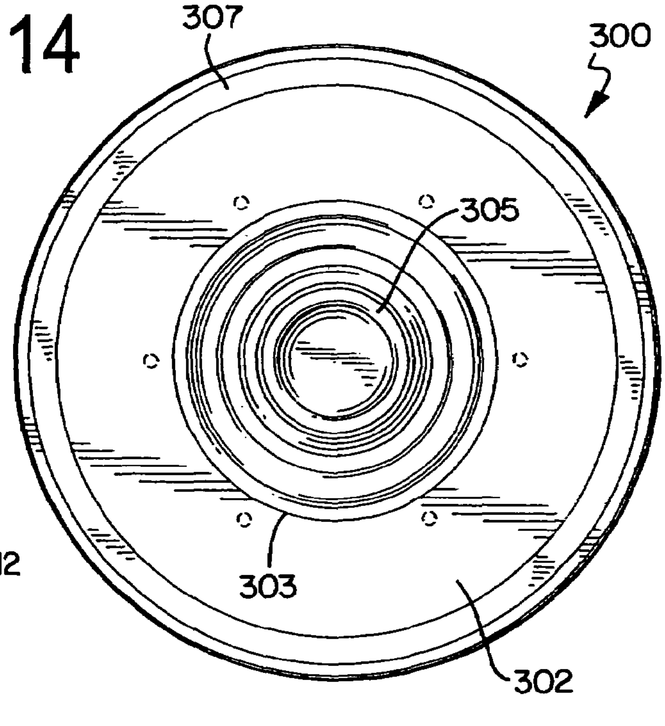
FIG. 14 is a top view of the sealing member of FIG. 13.
Figure 15:
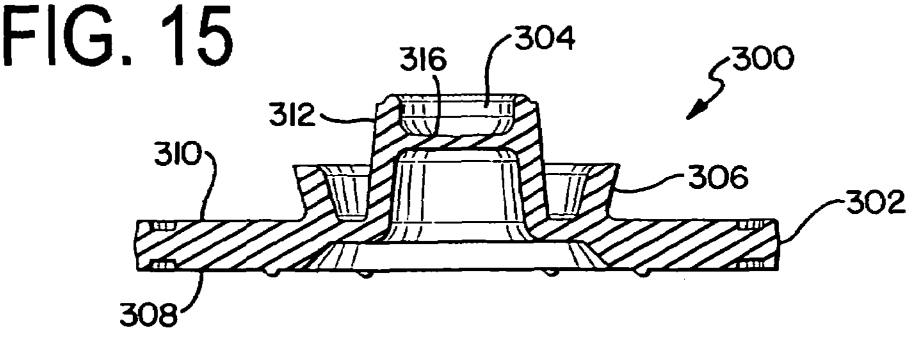
FIG. 15 is a cross-sectional view of the sealing member taken along lines 15-15 in FIG. 13.

As generally shown in FIGS. 13-15, the base 302 is generally disk-shaped. The disk or base 302 has a first surface 308 and a second surface 310. The first surface 308 faces into the connector 10 and the second surface 310 faces the container to be attached to the connector 10. The base 302 has the identical grooved structure at its periphery to attach the sealing member 300 to the connector 10 as described above.

Figure 16:
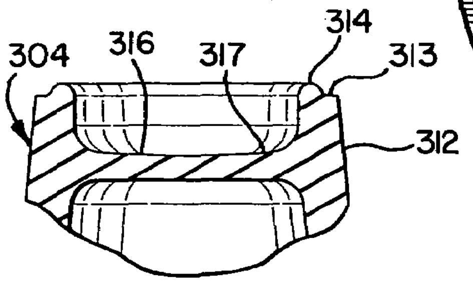
FIG. 16 is a partial cross sectional view of the sealing member shown in FIG. 15.

The diaphragm member 304 is generally a flexible member that extends from the second surface 310 of the base 302. The diaphragm member 304 extends from a generally central portion of the base 302. The diaphragm member 304 may be considered to be frustoconical in shape. The diaphragm member 304 has a frustoconical or annular sidewall 312 and a membrane 316 extending across and connected to the annular sidewall 312. The membrane 316 of the diaphragm member 304 is adapted to confront the closure member of the vial 14. As shown in FIG. 16, the membrane 316 has an outer surface 317 that is preferably slightly convex. The annular wall 312 has a lip 313 extending therefrom. The lip 313 is also annular. At a distal end, the lip 313 has a rounded protrusion 314. As explained in greater detail below, the diaphragm member 304 is capable of forming a first fluid tight seal with the closure of the container.

The annular ridge 306 extends from the second surface 310 of the disk 302. The annular ridge 306 is circumjacent the diaphragm 304 and is positioned outwardly of the diaphragm member 304. The annular ridge 306 tapers axially-outwardly from a proximal end to a distal end. As explained in greater detail below, the annular ridge 306 is capable of forming a second fluid tight seal with the closure of the container. As shown in FIGS. 13 and 15, the diaphragm member 304 extends from the second surface 310 at a first length. The annular ridge 306 extends from the second surface 310 at a second length. The second length is less than the first length, thus, the diaphragm member 304 extends from the second surface 310 a greater distance than the annular ridge 306.

Figure 17:
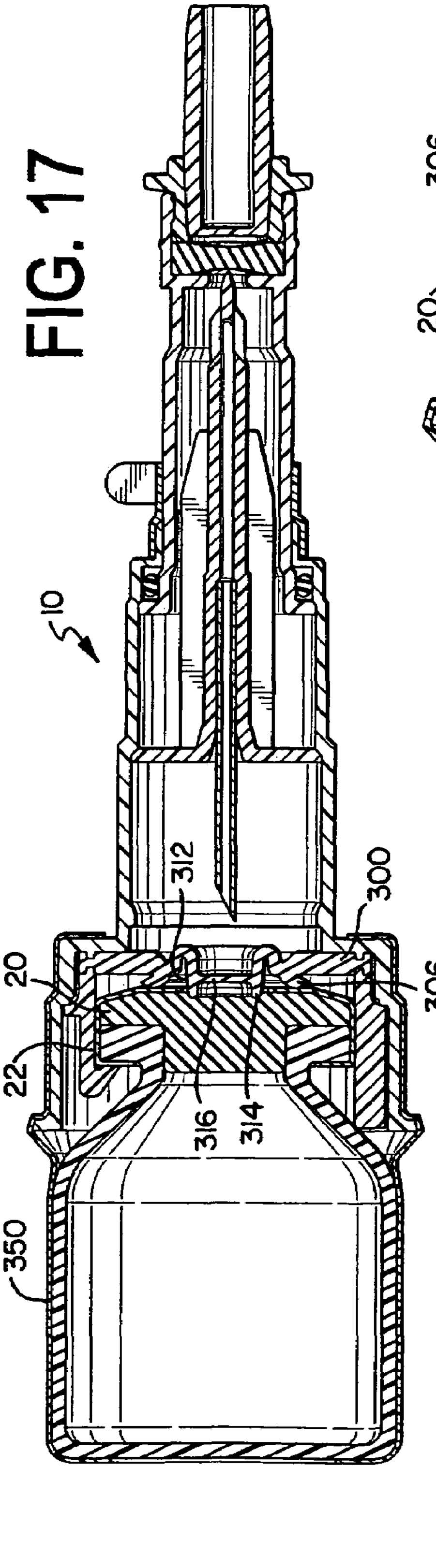
FIG. 17 is a cross-sectional view of the connector device of the present invention utilizing the sealing member of FIG. 13.
Figure 18:
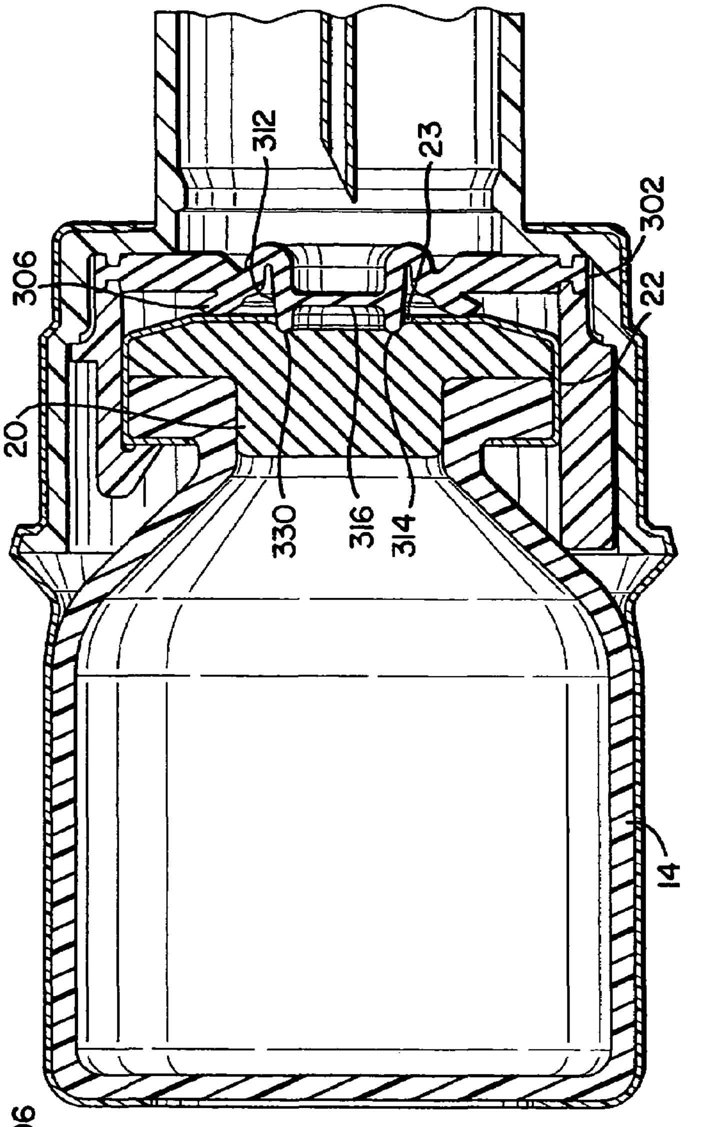
FIG. 18 is an enlarged partial cross-sectional view showing the sealing member of FIG. 13 sealing a drug vial.

FIGS. 17-18 show the sealing member 300 connected to the connector 10. The sealing member 300 is connected similarly as described above. FIGS. 17-18 also show the vial 14 connected to the connector 10. As discussed above, the vial 14 has a closure member that includes a rubber stopper 20 and a crimp ring 22. The crimp ring 22 has a central opening defining a target sight 23 (FIG. 18) on the rubber stopper 20. It is further noted that the vial 14 may be connected to the connector 10 and then have a shrink wrap member 350 applied over the vial 14 and connected to the gripper assembly 28. The vial 14, connector 10 (inactivated) and container 12 may be shipped in this fashion if desired.

When the vial 14 is connected to the connector 10, the sealing member 300 provides a dual seal on the vial 14. In particular, the diaphragm member 304 abuts the closure to provide a first fluid tight seal with the closure of the vial 14, and the annular ridge 306 abuts the closure to provide a second fluid tight seal with the closure of the vial 14. Specifically, the rounded protrusion 314 of the diaphragm member 304 indents the rubber stopper 20 at the target site 23 to form the first seal. A space 330 is maintained between the crimp ring 22 and the annular wall 312 and membrane 316 of the diaphragm member 304. The membrane 316 confronts the rubber stopper 20. The annular ridge 306 deflects outwardly against the crimp ring 22 to form the second seal. It is understood that other variations are possible to form a dual-seal such as with an o-ring.

As further shown in FIGS. 17 and 18, when the vial 14 is connected to the connector 10, the diaphragm member 304 initially contacts the rubber stopper 20 of the vial 14. As the vial 14 further advances into the gripper assembly 28, the diaphragm member 304 initially is displaced towards the piercing member 76. Upon further advancement, the annular wall 316 folds upon itself while the lip 312 forms a fluid tight seal on the rubber stopper 20. This action also moves the membrane 316 into a second position wherein the surface 317 moves from the slightly convex surface to a generally planar surface. The respective heights and flexibility of the diaphragm member 304 and annular ridge 306 allow these components to account for dimensional differences in heights of different closures.

Figure 19:
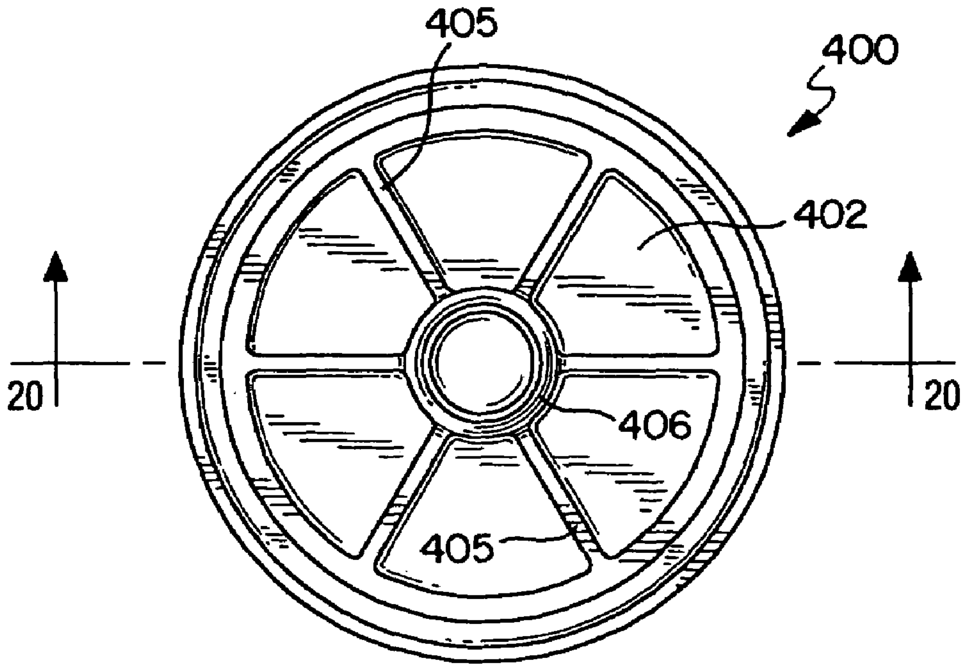
FIG. 19 is a plan view of another embodiment of the sealing member used in the connector device of the present invention.
Figure 20:
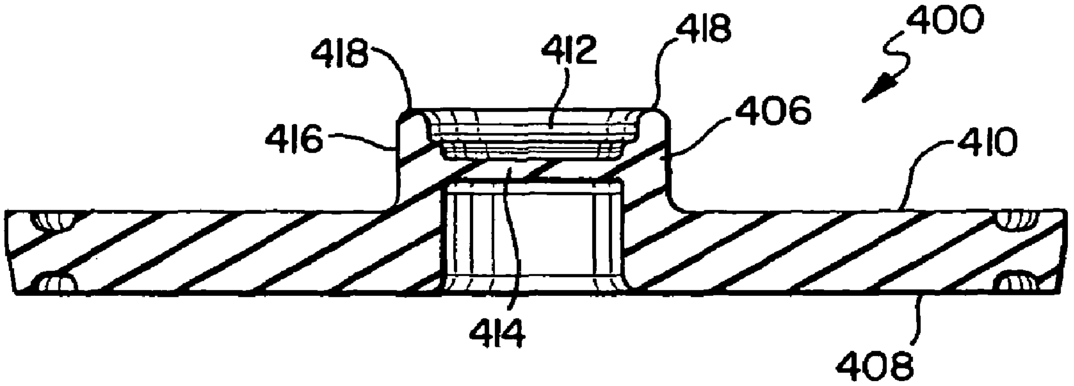
FIG. 20 is a cross-sectional view of the sealing member taken along lines 20-20 in FIG. 19.
Figure 21A:
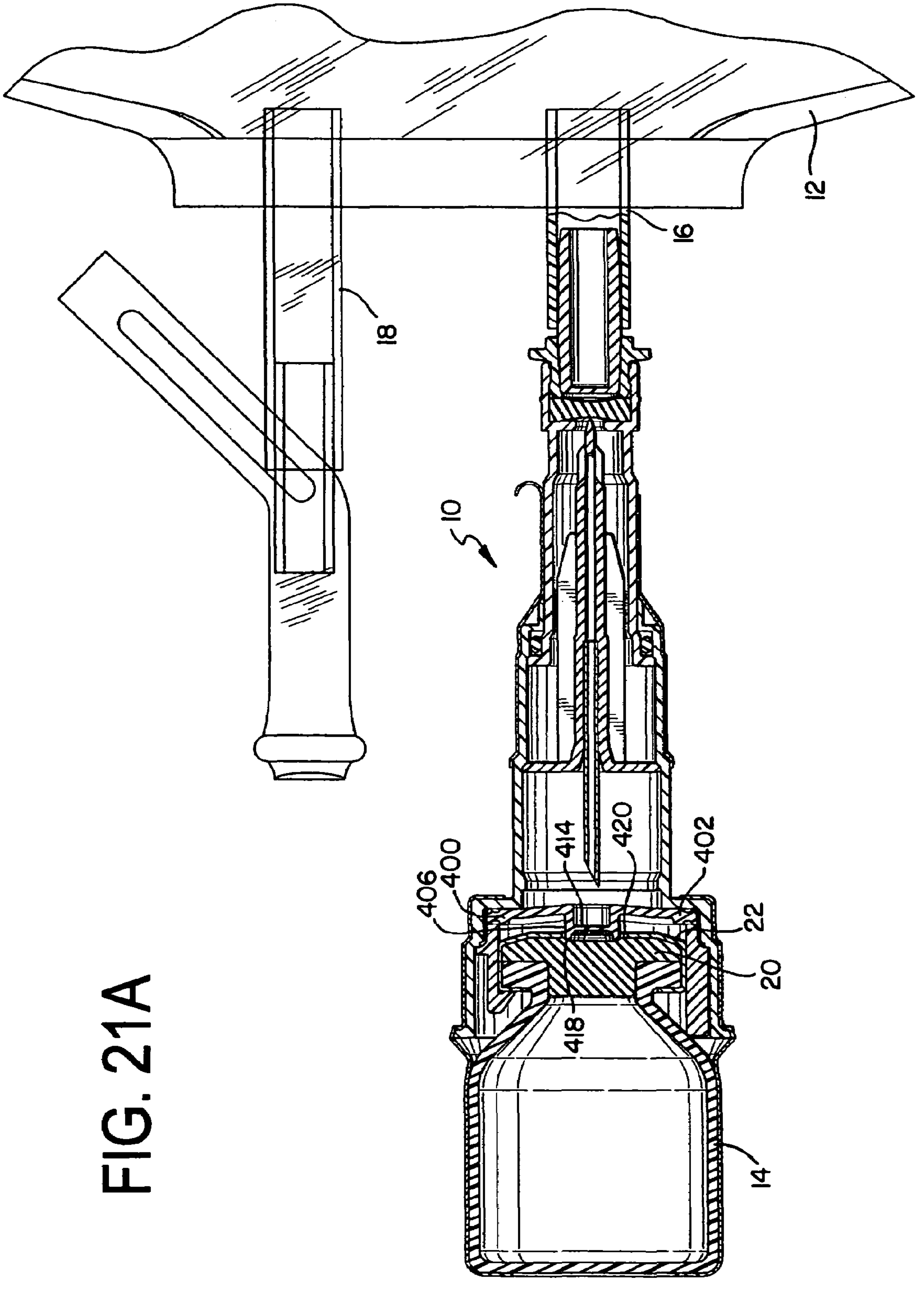
FIG. 21 A is a partial cross-sectional view of the connector device of the present invention utilizing the sealing member of FIG. 19, and having a drug vial fixedly secured to the connector device, the connector device attached to a flexible container and being in an inactivated position.
FIG. 21B is a partial cross-sectional view of the connector device shown in FIG. 21A wherein the connector device is in the initial stages of an activation process.
FIG. 21C is a partial cross-sectional view of the connector device of FIG. 21A in an activated position.
FIG. 21D is a partial cross-sectional view of the connector device of FIG. 21A in a deactivated position.
Figure 21B:
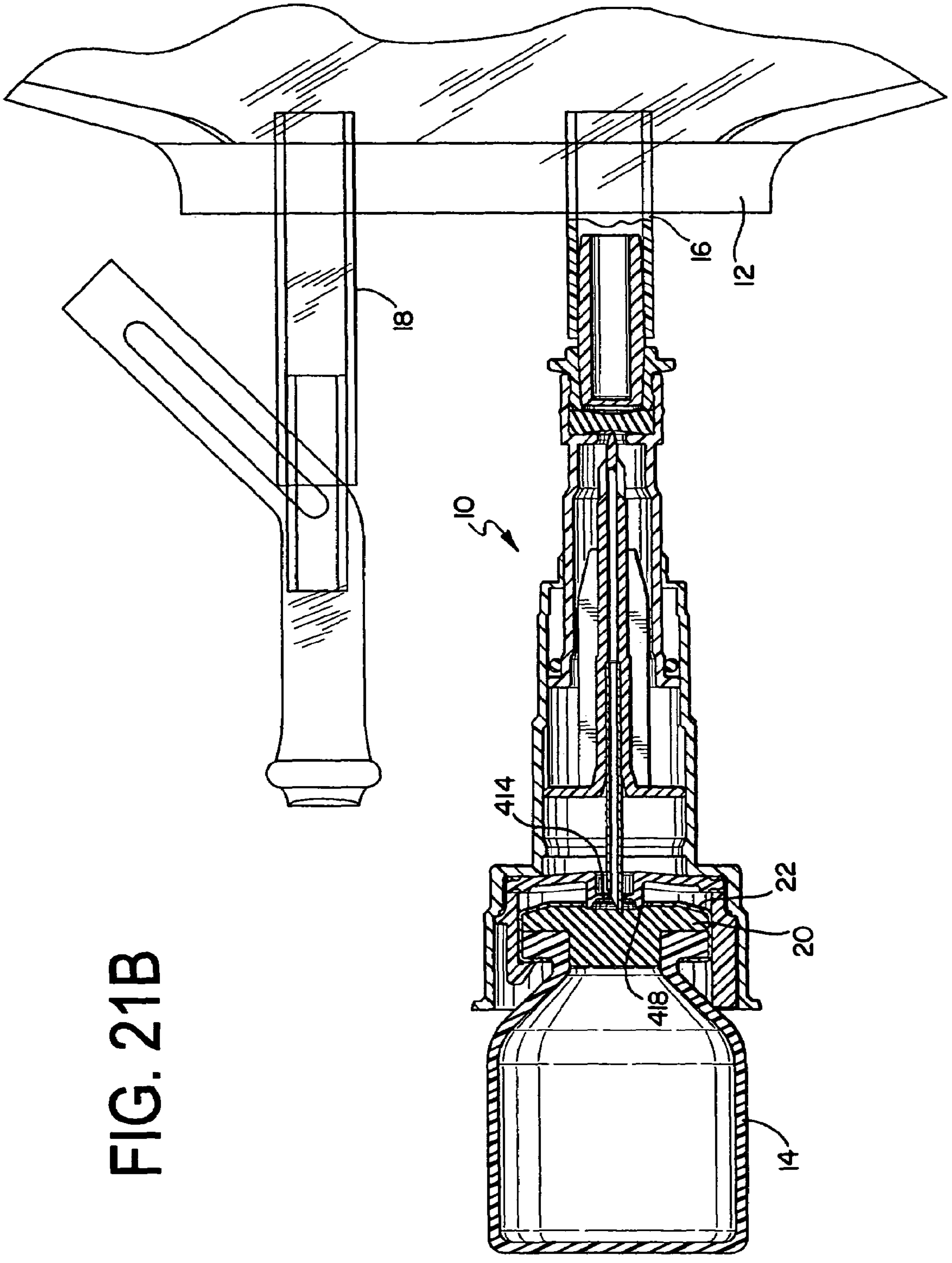
Figure 21C:
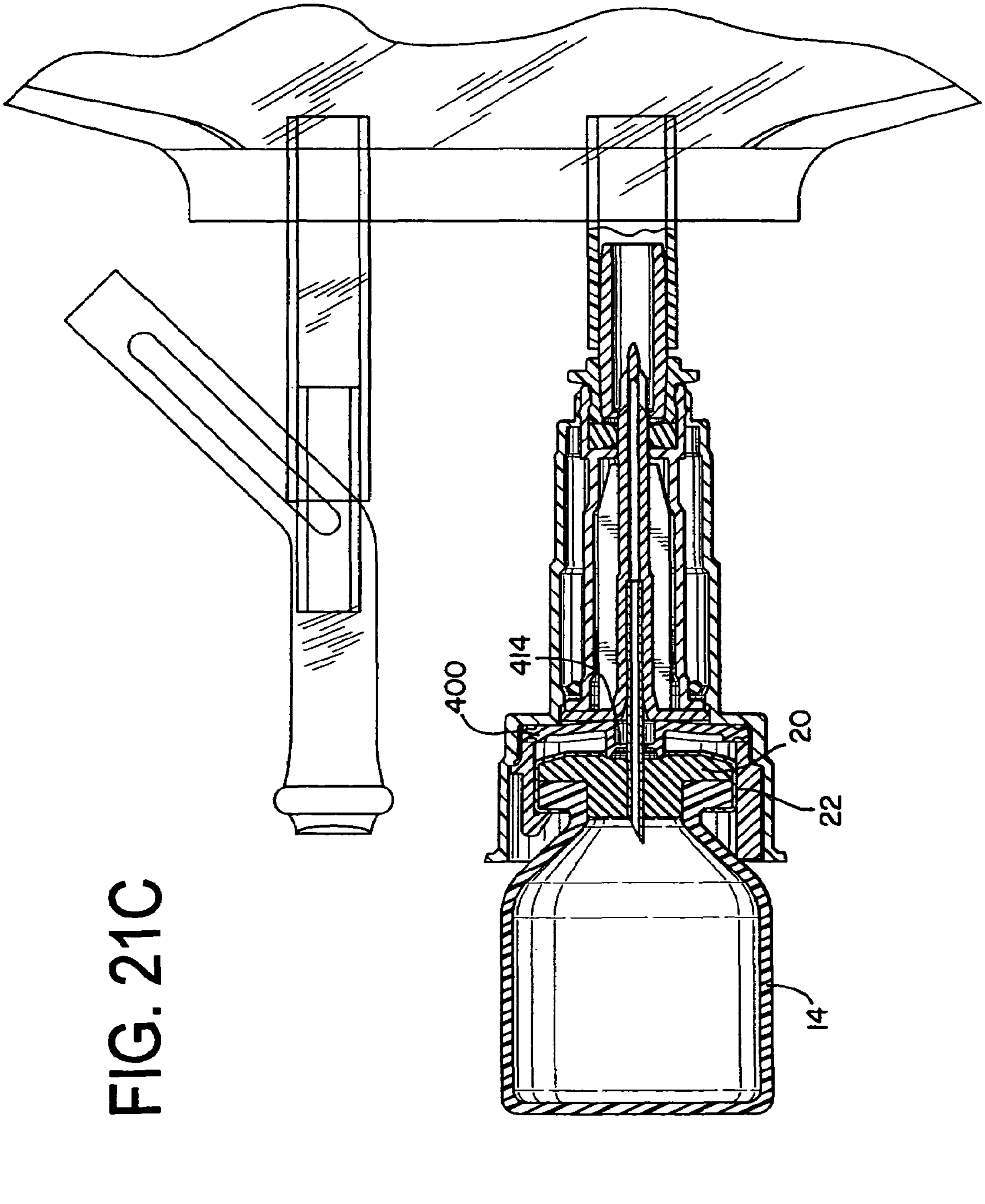
Figure 21D:
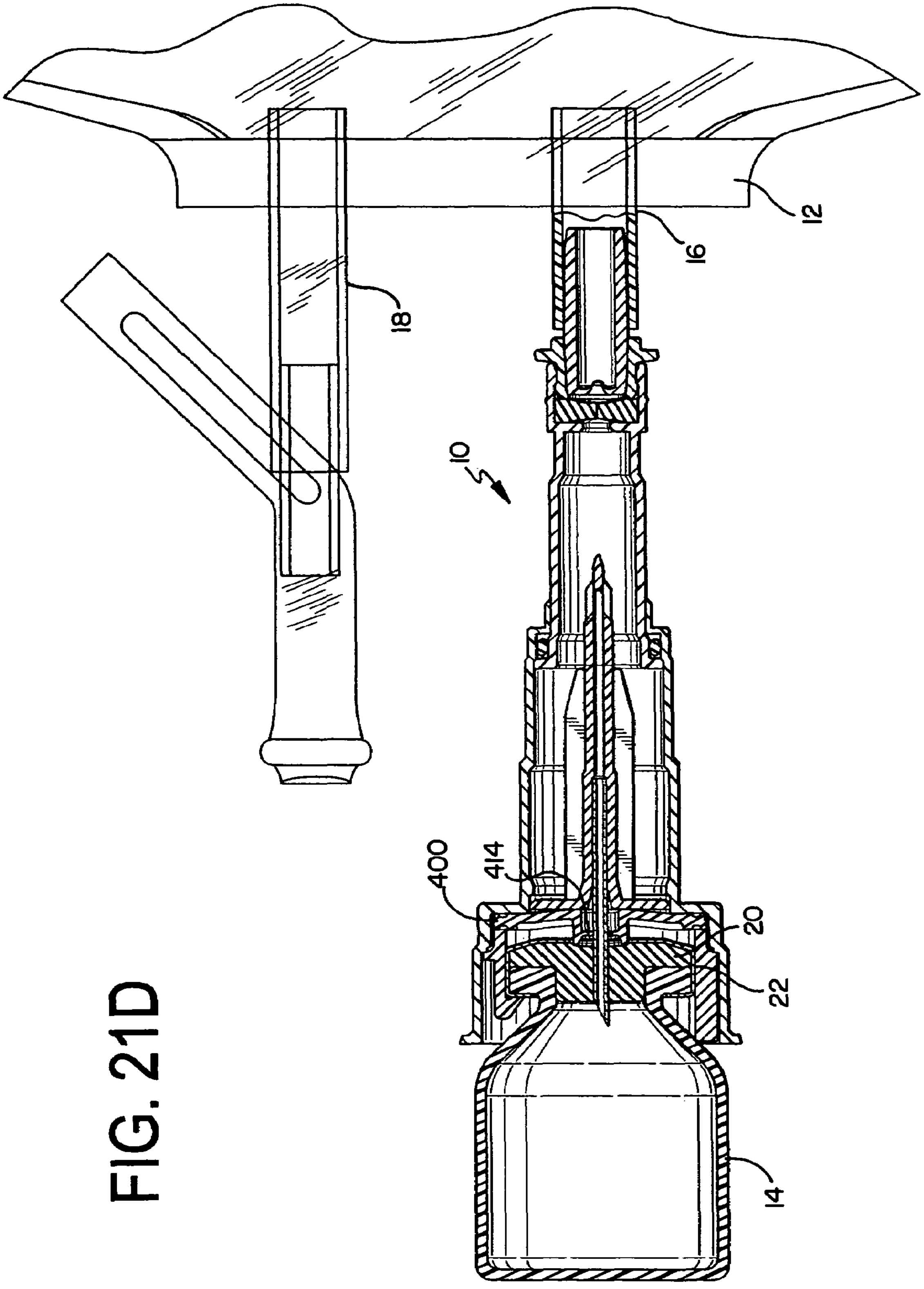

FIGS. 19-21 disclose another embodiment of the sealing member 84, used with the connector device 10, generally designated by the reference numeral 400. The sealing member 400, or septum 400, generally has a base 402 and an annular ring 406. The septum 400 is a single integral component made from a generally rigid material. As such, the septum 400 is preferably injection-molded in a single process. In one preferred embodiment, the septum 400 is made from polyethylene. PVC material may also be used.

As generally shown in FIGS. 19 and 20, the base 402 is generally disk-shaped. The disk or base 402 has a first surface 408 and a second surface 410. The first surface 408 faces into the connector 10 and the second surface 410 faces the container to be attached to the connector 10. The base 402 has the identical grooved structure at its periphery to attach the sealing member 400 to the connector 10 as described above. The base 402 also has a plurality of spokes 405 extending from the annular ring 406 along the base 402.

As the annular ring 406 is preferably integrally molded with the base 402, the annular ring 406 is a rigid member. The annular ring 406 extends from the second surface 410 of the base 402. The annular ring 406 is positioned at generally a central portion of the base 402. The ring 406 defines an opening 412, preferably a center opening 412, in the base 402. A membrane 414 is positioned in the center opening 412. In one embodiment, the membrane 414 may be considered a portion of the base 402 and integrally molded with the base 402. In a preferred embodiment, the membrane 414 is axially spaced from the base 402. This placement provides for enhanced sterilization and helps prevent the piercing member from coring a hole in the membrane 414 wherein the cored portion would block the piercing member 76. The membrane 414 is also designed to be spaced from the closure 20 of the vial 14 when the vial 14 is connected to the connector 10.

The rigid annular ring 406 has a protrusion 416 at a distal end. The protrusion 416 is tapered to a rounded end 418. The rigid annular ring 406 is capable of forming a fluid tight seal with the closure 20 of the vial 14.

FIG. 21 A shows the septum 400 connected to the connector 10. The septum 400 is cooperates similarly with the gripper assembly 28 to be mounted in the connector 10 as described above. FIG. 21A also shows the vial 14 connected to the connector 10. The vial 14 has the rubber stopper 20 positioned in the opening of the vial 14 and the crimp ring 22 positioned over the stopper 20. The crimp ring has an aperture that defines the target site 23 on the rubber stopper 20. When the vial 14 is connected to the connector 10, the septum 400 provides a fluid tight seal on the vial 14. In particular, the annular ring 406 abuts the rubber stopper 20 to provide the seal. In particular, the rounded protrusion 418 indents the rubber stopper 20 sufficiently to provide the fluid tight seal. The height of the annular ring 406 is set such that a sufficient interference fit is achieved between the annular ring 406 and the rubber stopper 20. The rounded end of the annular ring 406 assures that the rubber stopper 20 is indented but not cut by the ring 406. As further shown in FIG. 21A, the annular ring 406 indents the rubber stopper 20 at the target site 23. The annular ring 406 is spaced inwardly from the crimp ring 22 wherein a space 420 is maintained between the annular ring 406 and the crimp ring 22. As discussed, the membrane 414 is spaced from the rubber stopper 20. After the vial 14 is connected, the connector 10 can be activated as shown in FIGS. 21B and 21C wherein the piercing member 76 pierces through the membrane 414 and rubber stopper 20 and into the vial 14. The connector 10 can also be positioned in the deactivated position shown in FIG. 21D.

With some vials 14, the rubber stoppers 20 used may have imperfections across a top surface of the stoppers 20 The stoppers 20 may have bumps at locations that would correspond to the target site on the stopper. The stoppers 20 may also have identification markings. These imperfections or markings can vary the height of the stopper 20. The rigidity of the septum 400 sufficiently deforms the stopper 20 without piercing the stopper 20 and helps provide a sufficient fluid tight seal regardless of such imperfections or markings across the rubber stopper 20.

Figure 23:
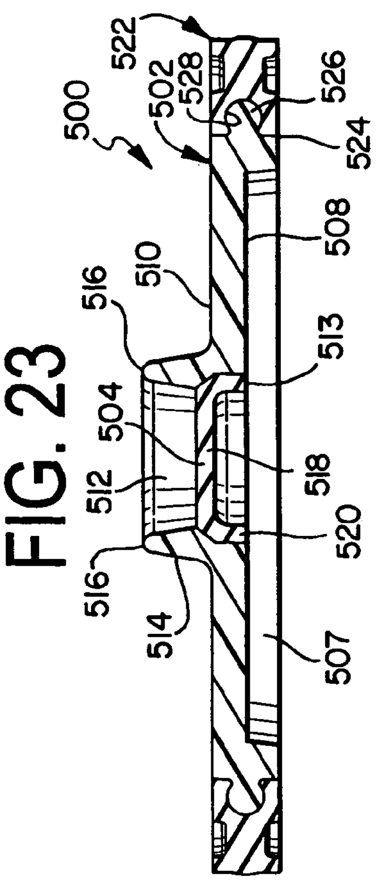
FIG. 23 is a cross-sectional view of the sealing member taken along lines 23-23 in FIG. 22.
Figure 24:
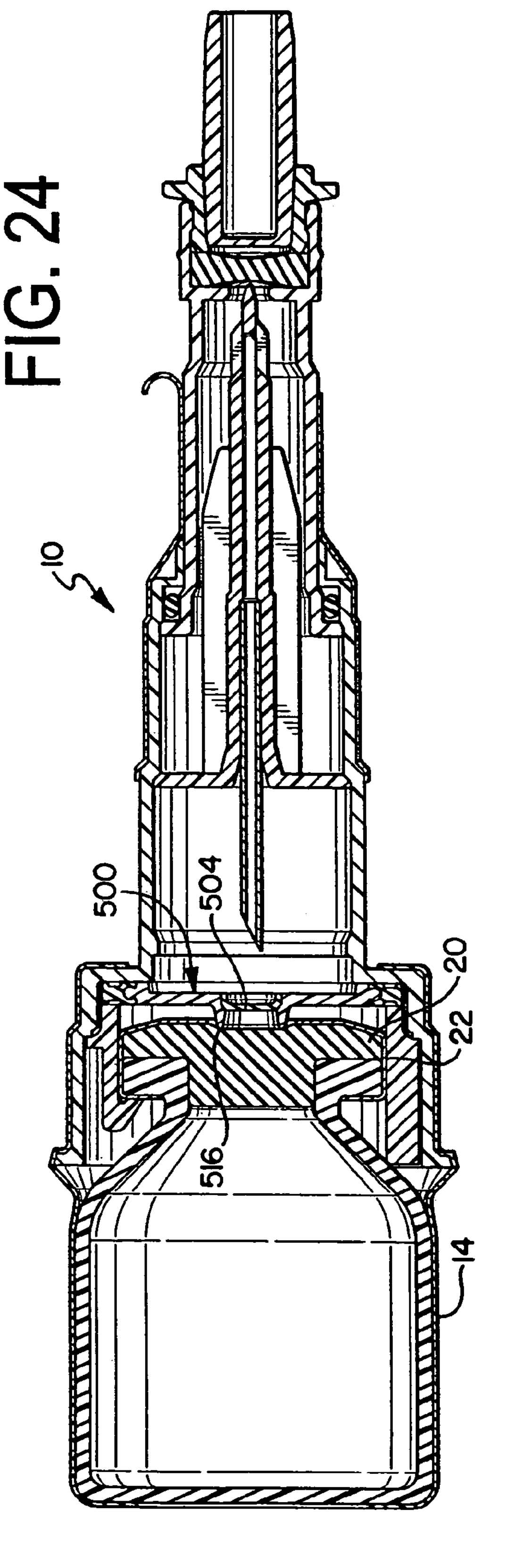
FIG. 24 is cross-sectional view of the connector device of the present invention utilizing the sealing member of FIG. 20.
Figure 22:
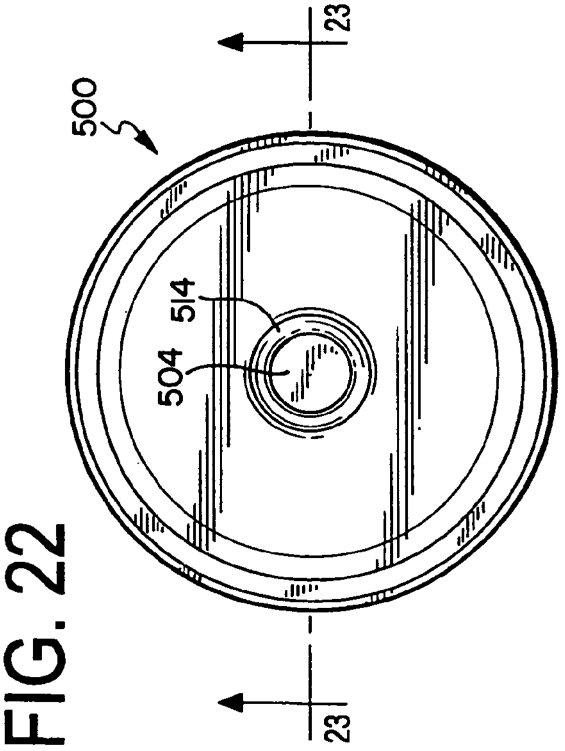
FIG. 22 is a plan view of another embodiment of the sealing member used in the connector device of the present invention.

FIGS. 22-24 disclose yet another embodiment of the sealing member 84, used with the connector device 10, generally designated by the reference numeral 500. Generally, the sealing member 500, or septum 500, has one portion made of rigid material and a pierceable portion made of a rubber material. In one preferred embodiment, the portions of the septum 500 are formed simultaneously together in a two-shot injection molded process. It is understood, however, that other processes can be used to connect the separate portions including an insert molding process. Adhesives or an interference fit could also be used.

As shown in FIGS. 22 and 23, the septum 500 generally has a base 502 and a membrane 504.

As generally shown in FIGS. 22 and 23, the base 502 is generally disk-shaped. The disk or base 502 has a first surface 508 and a second surface 510. The first surface 508 faces into the connector 10 and the second surface 510 faces the container to be attached to the connector 10. The base 502 has an opening 512 therethrough, preferably in a center of the base 502. The opening 512 defines an inner surface 513 on the base 502. The base further has an annular ring 514 extending from the second surface of the base 502 and around the center opening 512. The annular ring 514 is tapered wherein a distal end has rounded protrusion 516. The annular ring 512 is capable of forming a fluid tight seal with the closure 20 of the vial 14 as described below. The first side 508 has a recessed portion 507.

The membrane 504 is positioned in the center opening 512 and closes the opening 512. The membrane has a generally planar section 518 with a depending leg 520. The leg 520 is connected to the inner surface 513 of the base 502.

As further shown in FIGS. 22 and 23, the base 502 has the similar grooved structure as described above for connecting the septum 500 to the gripper assembly 28. In a preferred embodiment, the base 502 may have a collar 522. To that end, the base 502 has an outer peripheral edge 524. The collar 522 is connected to the outer peripheral edge. Specifically, the base 502 has a tongue 526 and the collar has an inner peripheral groove 528. The tongue 526 is received by the groove 528. The collar 522 has the grooved structure as described above. In addition, the collar 522 is formed of the rubber material like the membrane 504.

As discussed, the septum 500 is formed in one preferred embodiment by a two-shot injection molded process. The base 502 of the septum 500 is a rigid plastic material. The membrane 504 and collar 522 of the septum 500 are a softer rubber material. The components are molded together simultaneously in a two-shot injection molded process as is known in the art. The septum 500 possesses the rigidity from the plastic material that provides a fluid tight seal with the closure while also possessing a soft material in the membrane for the piercing member to easily pierce through.

FIG. 24 shows the septum 500 connected to the connector 10. The septum 500 is cooperates similarly with the gripper assembly 28 to be mounted in the connector 10 as described above. FIG. 24 also shows the vial 14 connected to the connector 10. The vial 14 has the rubber stopper 20 positioned in the opening of the vial 14 and the crimp ring 22 positioned over the stopper 20. The crimp ring has an aperture that defines the target site 23 on the rubber stopper 20. When the vial 14 is connected to the connector 10, the septum 500 provides a fluid tight seal on the vial 14. In particular, the annular ring 514 abuts the rubber stopper 20 to provide the seal. In particular, the rounded protrusion 516 indents the rubber stopper 20 sufficiently to provide the fluid tight seal. The height of the annular ring 514 is set such that a sufficient interference fit is achieved between the annular ring 514 and the rubber stopper 20. The rounded end of the annular ring 516 assures that the rubber stopper 20 is indented but not cut by the ring 406. As further shown in FIG. 24, the annular ring 514 indents the rubber stopper 20 at the target site 23. The annular ring 514 is spaced inwardly from the crimp ring 22 wherein a space 530 is maintained between the annular ring 514 and the crimp ring 22. After the vial 14 is connected, the connector 10 can be activated wherein the piercing member pierces through the membrane 414 and rubber stopper 20 and into the vial 14.

Figure 28:
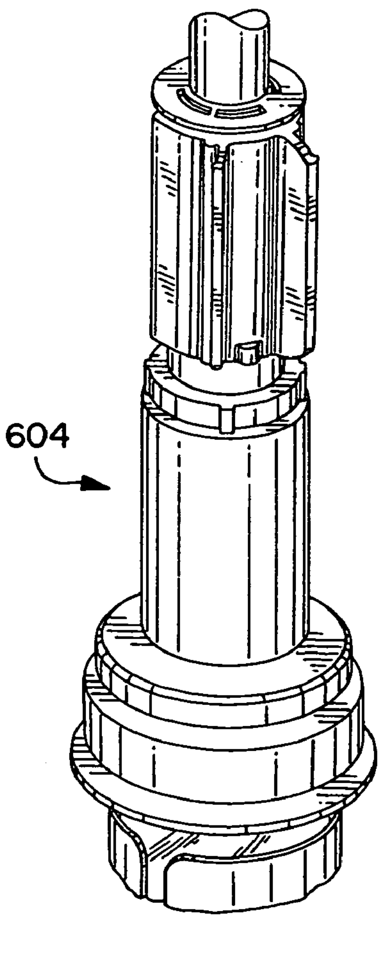
FIG. 28 is a perspective view of the locking device of FIG. 25 positioned on a connector device of the present invention.
Figure 29:
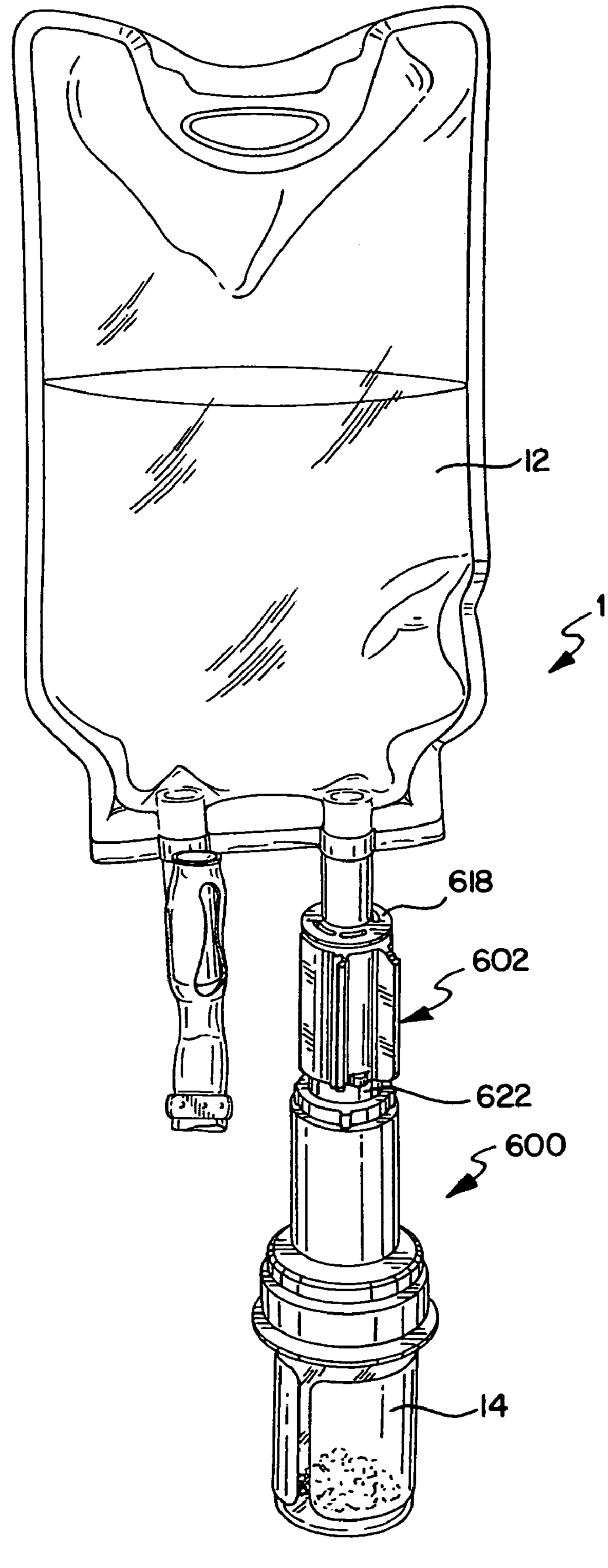
FIG. 29 is a perspective view of the locking device of FIG. 25 positioned on the connector device of FIG. 28, the connector device shown attached to a first container and a second container to collectively define a reconstitution assembly.

FIGS. 25-30 show a member in the form of a locking device for use in conjunction with another embodiment of the connector device 10 of the present invention. FIG. 29 depicts a connector, referred to with the reference numeral 600, connected to the first container 12 and the second container 14. It is understood that the connector 600 in FIG. 29 is substantially similar to the connector 10 of the previous embodiments, and can readily be utilized with those embodiments. As further shown in FIG. 29, the locking device, generally designated with the reference numeral 602, is releasably connected to the connector 600. As before, the first container 12 is preferably a diluent container such as a flexible bag. Similarly, the second container 14 is preferably a vial containing a drug. It is understood that the general structure of the connector 600 is similar to the embodiments previously described. The locking device 602 is generally a clip which affixes to the connector 600. The locking device 602 generally functions as a means for preventing the premature activation of the connector device 600 wherein relative sleeve movement is selectively prevented. The locking device 602 generally includes a securing portion 603 and a gripping portion 605.

Figure 25:
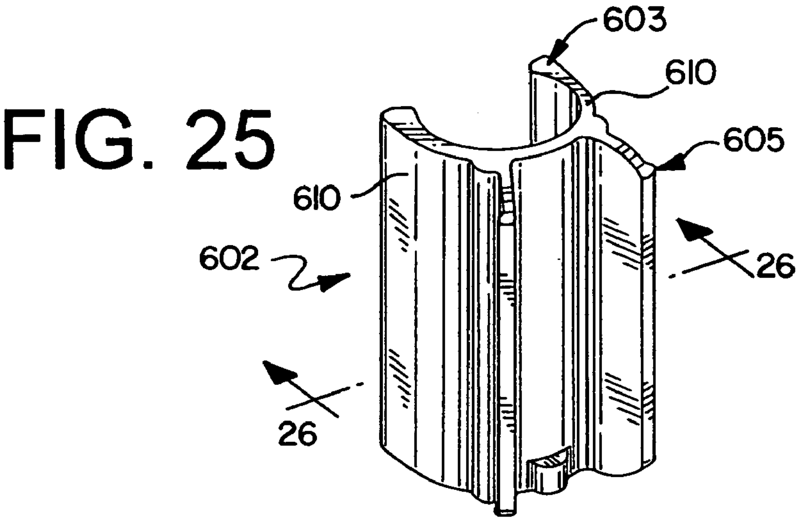
FIG. 25 is a perspective view of a locking device utilized according to another embodiment of the present invention.
Figure 26:
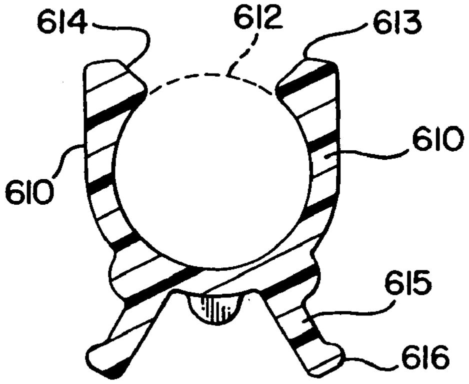
FIG. 26 is a cross-sectional view of the locking device taken along lines 26-26 of FIG. 25, a sleeve of the connector device shown in phantom.

FIG. 25 depicts the locking device 602 separated from the connector device 600. The securing portion 603 of the locking device 602 preferably includes two extensions 610. The securing portion is that portion of the locking device 602 which attaches to the connector device 600. The extensions 610 are a securing means for attaching the locking device 602 to a first sleeve 612 of the connector device 600. The extensions 610 preferably extend about a portion of the first sleeve 612 when the device is secured to the connector device 600. The two extensions 610 preferably form a penannular cylinder having a radius generally equal to the radius of the exterior of the first sleeve 612. The penannular cylinder has an opening sized to allow the first sleeve 612 to be snapped into and out of the penannular cylinder. As shown in FIG. 26, the two extensions 610 generally include lead-in sections 613. The lead-in sections 613 generally include sloped walls 614 which tend to channel the cylindrically shaped first sleeve 612 into the penannular cylinder formed by the extensions 610 when the sleeve 612 is inserted into the locking device 602.

The locking device 602 preferably includes the gripping portion 605 for facilitating the securing and removal of the locking device onto, or off of, the sleeve 612. The gripping portion 605 generally includes a handle, which as shown in FIG. 26, preferably includes two fins 615 that may be easily grasped simultaneously by a person using the thumb and forefinger of a single hand. The fins 615 preferably extend at an angle away from one another from where they are joined to a base portion of the securing portion 603 of the locking device 602. Ridges 616 are preferably located proximate to the terminal ends of the fins 614, which are opposite to the securing portion of the locking device 602. The ridges 616 allow the fins 614 to be more easily grasped.

Figure 30:
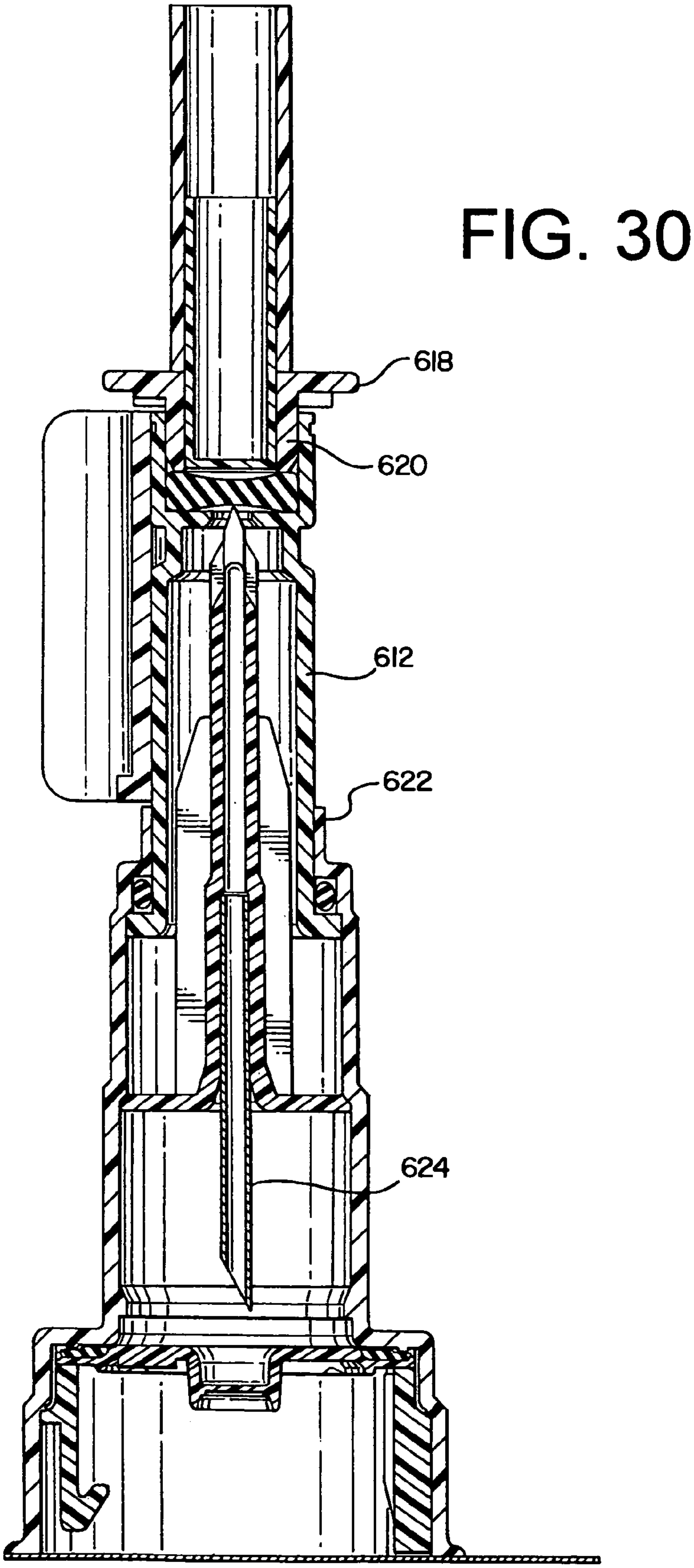
FIG. 30 is a cross-sectional view of the locking device of FIG. 25 positioned on a connector device of the present invention.

The locking device 602 is shown secured to the connector device 600 in FIGS. 28-30. The locking device 602 is secured about the first sleeve 612. The locking device 602 generally has structure operative to maintain the sleeves in an essentially fixed relative position. The locking device 602 has a portion that abuts the second sleeve 622 and another portion that abuts a structure associated with the first sleeve or the first container. The device 602 could abut other structures as desired to maintain the sleeves in an essentially fixed relative position. More specifically, the locking device 602 abuts a structure such as a flange 618, ledge or extension member 618 extending from a port connector 620, which is preferably used to secure the connector device 602 to the first container 606. The port connector 620 is substantially similar to the port connector 30 previously described. It is understood that the flange 618 of the port connector assembly 30 can be considered as being associated with the first sleeve 612. The other end of the locking device 602 abuts an end, or end flange of a second sleeve 622 when the locking device 602 is secured to the connector device 604. In this manner, the extensions 610 serve the dual purpose of securing the locking device 602 to the connector device 604 and of locking the connector 600 so that the first container 12 and second sleeve 622 cannot be moved towards one another to place the device 600 in the activated position. Thus, the locking device 602 cooperates with the structures of the device 600 to prevent the first sleeve 612 and the second sleeve 622 of the device 600 from axially moving. Accordingly, the locking device 602 must be physically removed from the first sleeve 612 before the connector 600 can be activated. As it is understood that the sleeves cooperate with the piercing member to establish fluid communication, the locking device 602 can be considered to selectively prevent movement of the piercing member as well.

Figure 27:
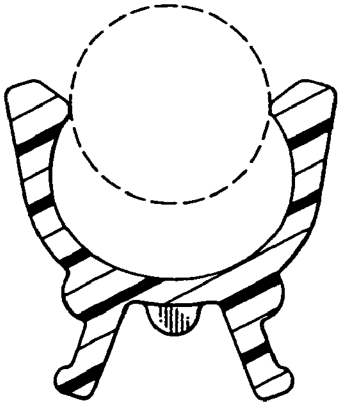
FIG. 27 is a cross-sectional view of the locking device of FIG. 26 in a flexed position about the sleeve shown in phantom.

The locking device 602 is preferably constructed of a semi-rigid polymeric material. The material preferably has rigidity sufficient so that when the locking device 602 is attached to the connector device 600 it prevents premature activation by not allowing axial movement of the first sleeve 612 and second sleeve 622 relative to one another. However, the material preferably is flexible enough such that the extensions 610 flex outward when the cylindrical first sleeve 612 is inserted or withdrawn in a latitudinal direction from the locking device 602 as shown in FIGS. 26 and 27. In the preferred embodiment, the locking device 602 is molded from a single material, but other embodiments may utilize different materials for different portions of the device 602.

In use, the locking device 602 is preferably applied to the first sleeve 612, where it remains until a user is prepared to activate the connector 600. The locking device 602 may be used in conjunction both with connectors 600 having first and second containers preattached, or in conjunction with connectors 600 which have means for attaching to the first and second containers. Preferably, at least the first container 12 is preattached. When it is desired to activate the connector 600, the user ensures the first and second containers 12, 14 are attached, or attaches them as necessary. At that point the connector device 600 is ready to operate, as shown in FIG. 29. The user then grasps the handle of the locking device 602, presses the fins 615, and pulls the locking device 602 away from the first sleeve 612. Once the locking device 602 is removed, the user positions the second container 14 on a hard surface. The user then grasps a top surface of the flange 618 of the port connector 620, preferably using the tips of the thumb, index finger and middle finger. The user then applies force (a generally vertical force in one preferred embodiment) to the flange 618 in the direction of the second container 14, moving the first container 12 towards the second container 14. In doing so, fluid communication is established between the first and second containers 12, 14 by the piercing member 624 of the connector device 600. The connector device 600 is then in the activated position wherein fluid can flow between the containers 12, 14.

The use of the locking device 602 of the present embodiment in conjunction with the connector device 600 attached to the first container 12 and second container 14 has numerous benefits. The locking device 602 prevents premature or inadvertent activation of the connector 600. The locking device 602 maintains the connector 600 in an inactivated position even when a force, a force which would otherwise commence the activation process or result in activation of the connector device, is applied. A typical user would be unable to activate the connector device without first removing the locking device 602 because they would be unable to generate sufficient force to break the locking device 602. In addition, the locking device 602 according to the present embodiment is a highly visible indicator that the connector device is not in the activated position. In one preferred embodiment, the sleeves of the connector 600 could have a first color or colors. The locking device 602 could have a color perceptively different from the sleeves or other portions of the connector 600 so that one would readily see that the locking device 602 is installed on the connector 600 and has yet to be removed. The locking device 602 is furthermore inexpensive to manufacture and simple to use.

FIGS. 31-36 disclose another embodiment of the present invention for preventing premature activation of the connector device of the present invention. In this particular embodiment, the means are integral with the connector. This means for preventing premature activation preferably includes the use of a first sleeve having a raised protuberance and a second sleeve having an annular rim. It is understood that these structures could be switched on the sleeves. It is further understood that the raised protuberance and rim may be considered a locking member that allows movement of the sleeves only when in a predetermined position. It is understood that the sleeves in this embodiment are similar to the sleeves of the previous embodiments. Other components of the device are also similar.

Figure 33:
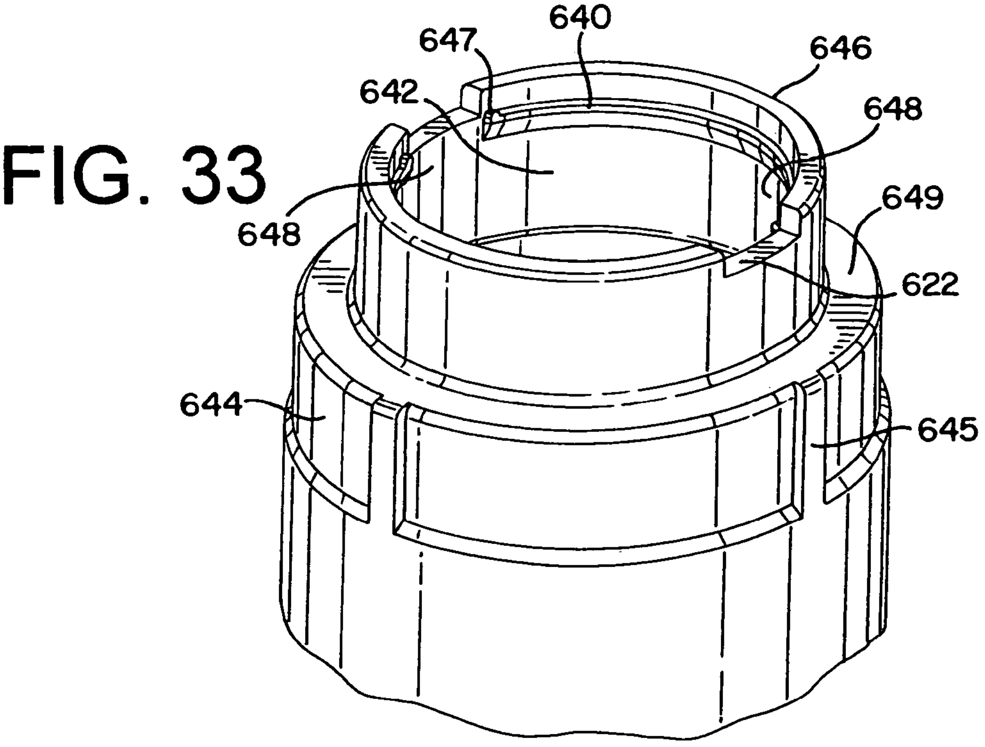
FIG. 33 is a partial perspective view of the second sleeve of the connector device of FIG. 31.

In this embodiment and as shown in FIG. 33, the connector 10,600 generally has similar sleeve structure as described above. An annular rim 640 is preferably located on an interior surface 642 of a second sleeve 644 and extends radially inward. The second sleeve 644 is substantially similar in structure to the second sleeve 34 discussed above. The rim 640 preferably extends about the interior surface 642 proximate to a first end 646 of the second sleeve 644. The rim 640 preferably includes at least one opening 648, more preferably two or more openings. When two openings are used, as shown in FIG. 33, the openings 648 are preferably arranged on generally opposite sides of the interior surface 642. The second sleeve 644 further includes a shelve 649, the interior surface of which contacts a first sleeve 650 when the connector device is assembled and in an inactivated position.

As further shown in FIG. 33, the second sleeve 644 preferably further includes anti-nesting ribs 645 positioned on an exterior surface of the sleeve 644. The anti-nesting ribs 645 are generally located towards one end of the sleeve 644 and towards an end flange of the sleeve 644. The anti-nesting ribs 645 allow for the sleeves to become easily separated when multiple sleeves are loaded in a bin when assembling the connector 10 in an automated process. It is understood that a single anti-nesting rib could be used while in one preferred embodiment, four anti-nesting ribs 645 are used. It is further understood that the anti-nesting rib 645 could vary in size and include a rib that extends around the full periphery of the sleeve 644.

Figure 36:
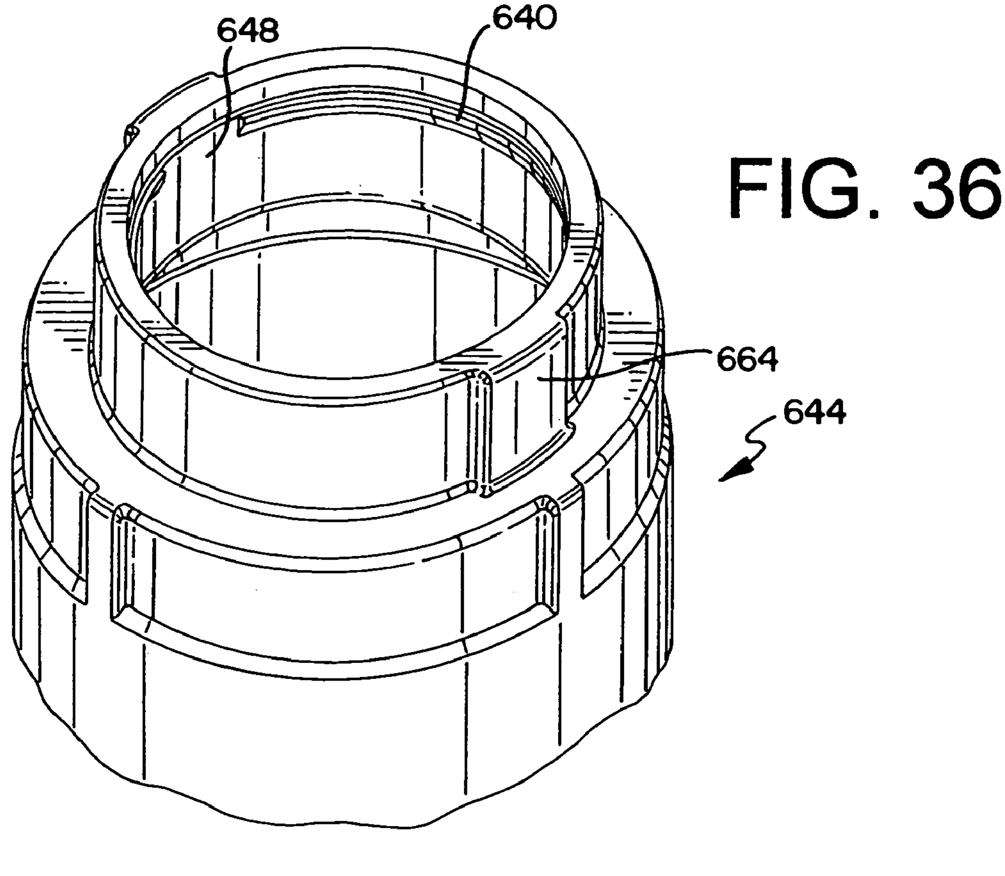
FIG. 36 is a partial perspective view of the second sleeve of the connector device of FIG. 35.

The second sleeve 644 preferably includes visual means for indicating the position of the openings 648 when the first sleeve 650 is mounted within the second sleeve 644, and would otherwise obscure a user from seeing where the openings 648 are located. One visual means for indicating the location of the openings 648, and hence, the proper relative rotational positions of the sleeves is shown in FIG. 33. The visual means includes cut-out portions 662 from the first end 646 of the second sleeve 644. The cut-out portions 662 are preferably the same width as the openings 648 and are aligned with the openings 648. Other visual means for indicating the location of the openings 648 may be used with the same beneficial results. One other example of visual means is shown in FIG. 36. There the openings 648 in the rim 640 are aligned with a raised segment 664 on the exterior surface of the second sleeve 644. Numerous other visual means for indicating the location of the opening 648 immediately come to mind without significant departure from the means indicated herein, including color.

In the embodiment depicted in FIG. 33, tactile means for indicating the position and alignment of the openings 648 is provided. Detents 647 are preferably located proximate to the openings 648 on an upper surface of the rim 640. When used in conjunction with the first sleeve member 650 as described in greater detail below, the detents 647 provide a tactile means which can be felt by the user through resistance to the rotation of the first sleeve, thereby indicating the position of the openings 648.

Figure 31:
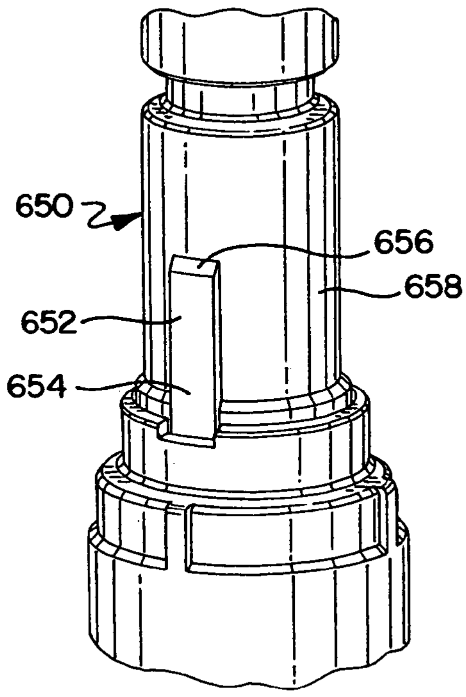
FIG. 31 is a partial perspective view of associated first and second sleeves of a connector device according to another embodiment of the present invention.
Figure 32:
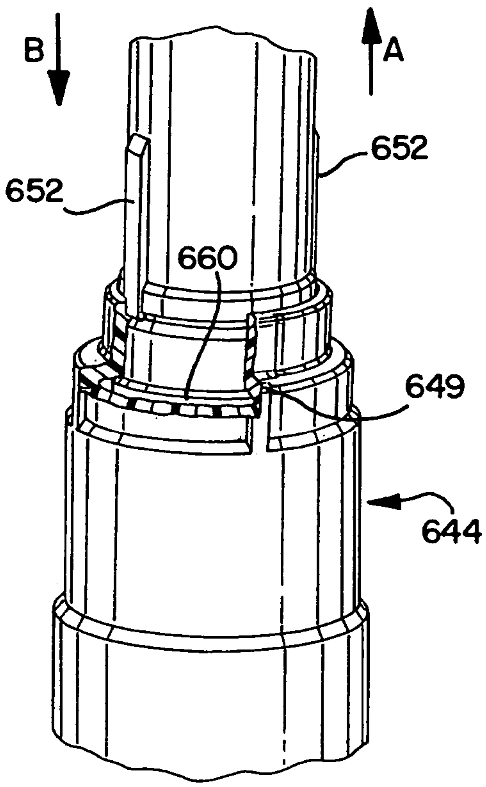
FIG. 32 is a partial cut-away perspective view of the sleeves of the connector device of FIG. 31.

The second sleeve 644 is preferably associated with the first sleeve 650 as shown in FIGS. 31 and 32. The first sleeve 650 is substantially similar in structure to the first sleeve 32 described previously. The first sleeve 650 preferably includes a flange 660 proximate to its second end which engages the second sleeve 644 when they are in an inactivated position. The first sleeve 650 preferably also includes at least one raised protuberance 652. In this embodiment, two raised protuberances 652 are used. The raised protuberances 652 are preferably raised steps and have a substantially flat top portion 654, or planar portion 654 which terminates in a ramp 656. The step preferably has a length which is greater than the distance required to move the device from an inactivated position to an activated position, but the step does not extend the full length of the first sleeve. Rather, it has a terminal end at the ramp 656 beyond which the first sleeve 650 extends in a continuing cylinder.

It is preferable that the cylindrical portion of the first sleeve 650 continue beyond the terminal end of the step to provide a constant annular surface 658 having a constant diameter which a machine can grasp consistently regardless of the rotational orientation of the first sleeve 650. This is useful in some machine manufacturing and sterilization processes because the machine can more easily grasp a cylinder having a constant diameter than an irregularly shaped cylinder having protuberances.

When the first sleeve member 650 and second sleeve member 644 are in an inactivated position as shown in FIG. 32, the flange 660 of the first sleeve member 650 engages the shelve 649 of the second sleeve member 644 preventing the first sleeve member 650 from moving in the direction of arrow A, and from becoming separated from the second sleeve member by movement in the direction of arrow A. The first and second sleeves 644, 650 are associated and connected to one another in this manner. The sleeves 644, 650 may move rotationally with respect to one another, and when the sleeves 644, 650 are properly aligned, as described in greater detail below, the first sleeve 644 may move relative to the second sleeve 650 in the direction of arrow B.

The rim 640 of the second sleeve member 644 and the raised protuberance 652 of the first sleeve member 650 operate cooperatively to maintain the sleeve members 650, 644 in the inactivated position and to prevent premature activation of the connector device 10,600. The protuberance 652 and rim 640 can also be considered radial extensive elements. In one preferred embodiment, the radially extensive elements are integral with the sleeves 650, 644. In the inactivated position the relative axial movement of the first sleeve 650 in the direction of arrow A is restricted by the engagement of the flange 660 of the first sleeve 650 and the shelve 649 of the second sleeve 644. The relative axial movement of the first sleeve 650 in the direction of arrow B is also restricted unless the raised protuberance 652 of the first sleeve 650 is aligned with the opening 648 of the rim 640 on the second sleeve 644. When they are not aligned, the raised protuberance 652 contacts the rim 640 and prevents axial movement of the sleeves 644, 650. Even though the axial movement is restricted when the sleeves are misaligned, rotational movement is still possible. When the sleeves 644, 650 have been rotated such that they are properly aligned, a user need only apply that force which is required to pierce the closures of the containers 12, 14 to which the sleeves 644, 650 are attached in order to move the sleeves 644, 650 to the activated position.

Figure 35:
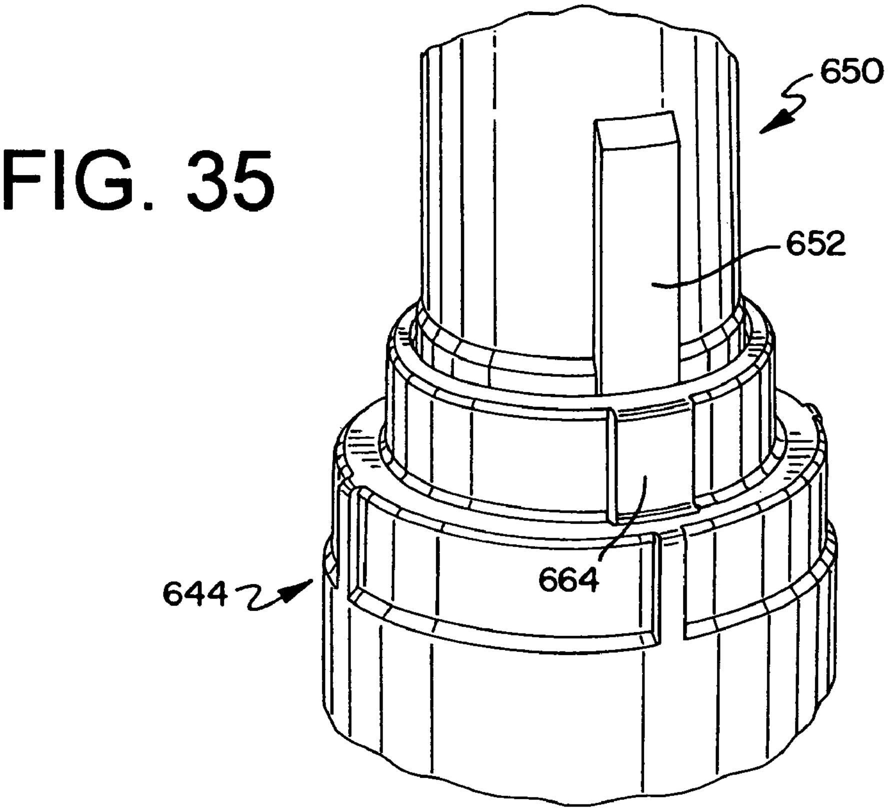
FIG. 35 is a partial perspective view of associated first and second sleeves of a connector device according to another embodiment of the invention.

The proper alignment of the sleeves 644, 650 includes aligning the raised protuberances 652, or steps, with the openings 648 of the rim 640 as shown for one embodiment in FIGS. 31-33. A user may employ the visual means of alignment by visually aligning the step of first sleeve 650 with the cut-out 662 of the second sleeve 644. Another embodiment shown in FIG. 35 depicts the alignment of the step 652 of the first sleeve 650 with the raised segment 664 of the second sleeve 666. The tactile means of indicating alignment may be used in conjunction with or separate from the visual means. The detents 647 on the ribs 640 proximate to the openings 648 contact the protuberance 652 of the first sleeve 650 when it is rotated, indicating the presence of the opening 648.

Figure 34:
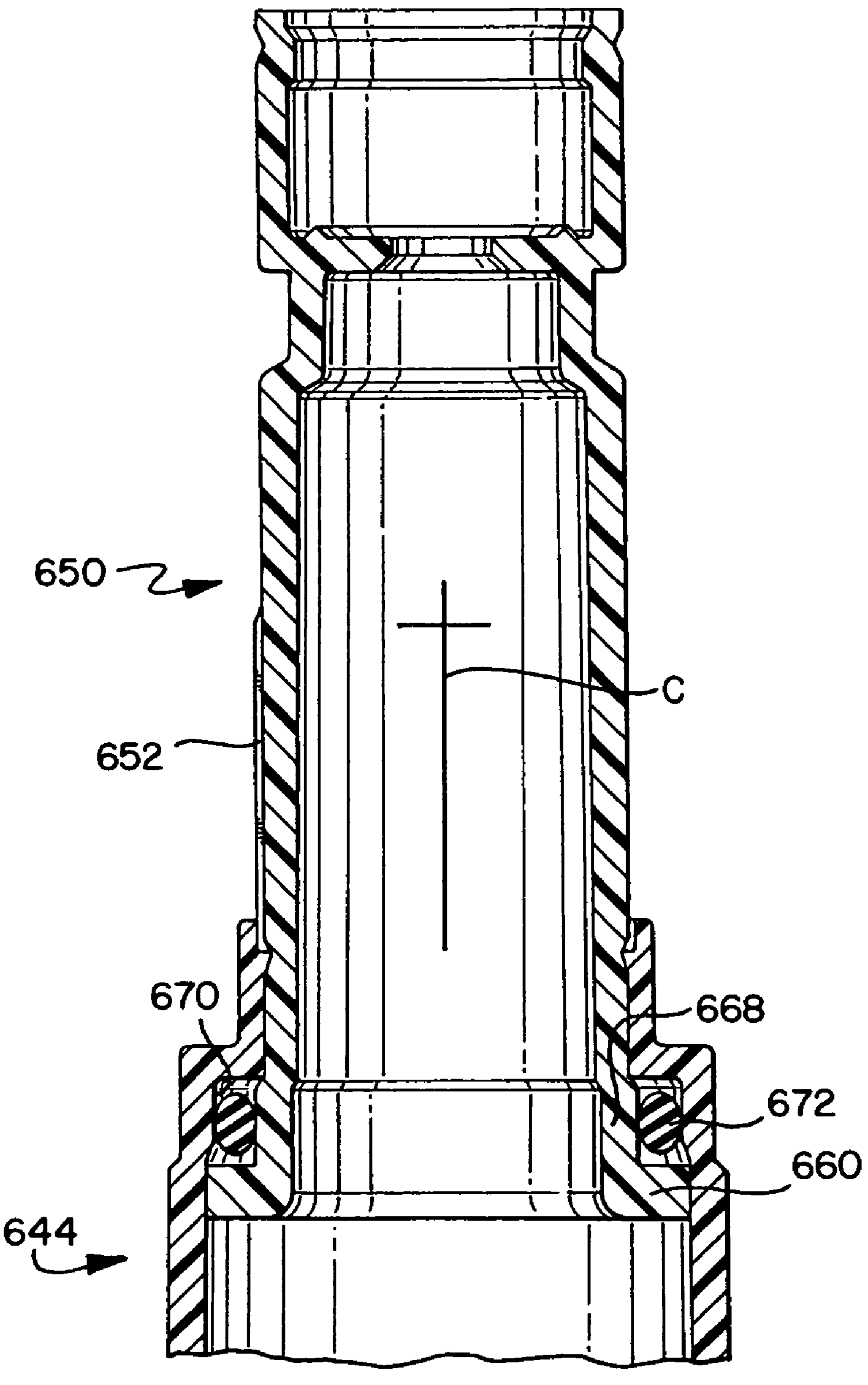
FIG. 34 is a partial cross-sectional view of the sleeves of the connector device of FIG. 31.

FIG. 34 is a partial cross-sectional view of the engaged first and second sleeve members 644, 650. The first sleeve 650 includes the raised protuberance 652, or step. It further includes the flange 660 and a sealing surface 668 which preferably forms a hermetic seal with an interior wall 670 of the second sleeve 644 through the use of an o-ring 672. It is preferable for ease of molding that the raised protuberance 652, or step, have a diameter or height from a center line C through the cylindrical first sleeve 650 which is less than the diameter or height of the sealing surface 668 of the first sleeve 650. By maintaining the raised protuberance 652 at a height less than the height of the sealing surface 668, the first sleeve 650 may be easily withdrawn from a mold (not shown) during manufacture in the direction of the flange 660. This makes de-molding simpler, quicker, and-results in a time and cost savings in molding the part.

The visual means of indicating alignment of the sleeves 644, 650 may also be used during manufacturing of the connector device to ensure misalignment of the sleeves. During manufacture and shipping of the connector device it is preferable to have the sleeves 644, 650 misaligned to prevent premature activation. Therefore, when the first and second sleeve members 644, 650 are joined during manufacture they are intentionally misaligned. This may be accomplished in a number of different ways. One method of insuring misalignment is to assemble the first and second sleeve members 644, 650 without respect to the alignment or misalignment of the sleeves. The alignment is then checked, preferably using a visual indicator. The visual indicator may include the cut outs 662 or raised segments 664 which are described above and are commonly referenced by a user to check for alignment. The checking of the alignment is preferably automated in the manufacturing process, and may be performed by a programmed camera system. When the camera system detects sleeves which are misaligned, they are allowed to pass through. When the camera system detects aligned sleeves, they are purposefully misaligned, and preferably rechecked, before being allowed to pass through.

Another acceptable method of ensuring misalignment during manufacture is to initially position the sleeves 644, 650 such that they are purposefully misaligned. The misalignment may then be checked using a camera or other automated means if desired.

Figure 37:
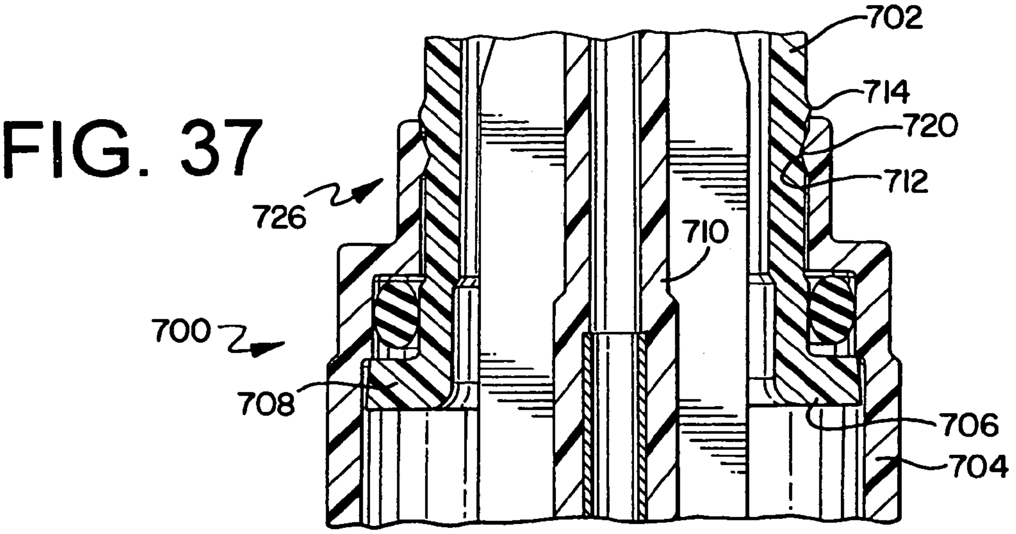
FIG. 37 is a partial cross-sectional view of first and second sleeves of a connector device according to another embodiment of the present invention, the connector device being in an inactivated position.
Figure 38:
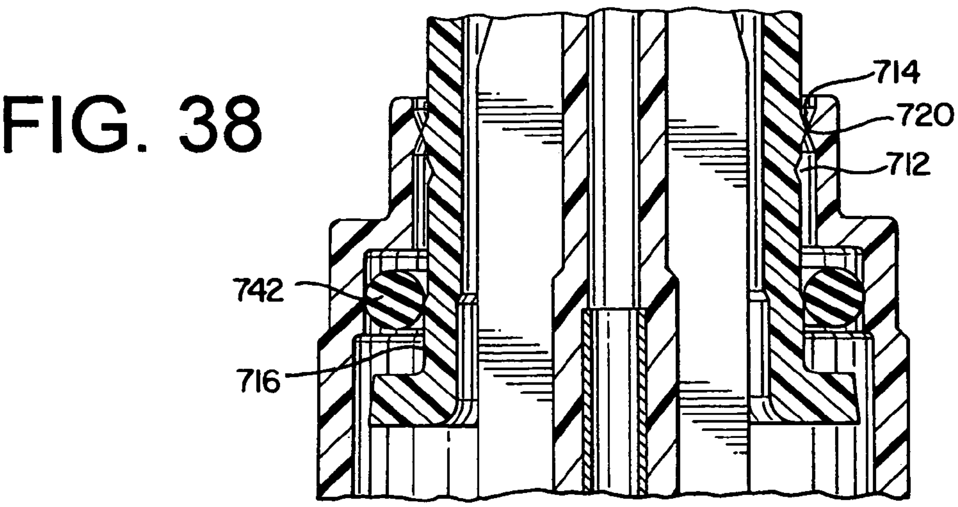
FIG. 38 is a partial cross-sectional view of the connector device of FIG. 37 in transition from the inactivated position to an activated position.
Figure 39:
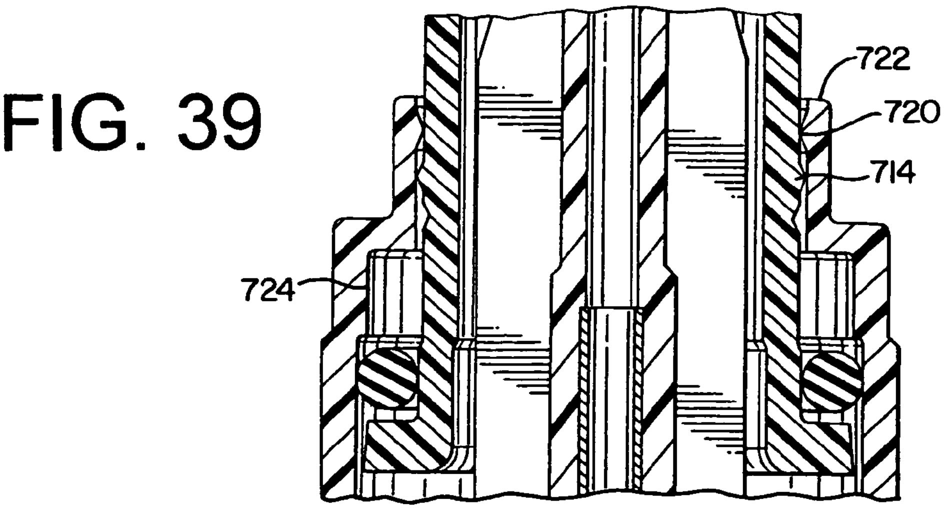
FIG. 39 is a partial cross-sectional view of the connector device of FIG. 37 and proceeding to the activated position.

FIGS. 37-39 disclose another embodiment of a means for preventing premature activation of a connector device of the present invention. The connector device, depicted generally as reference numeral 700, preferably includes a first sleeve 702 and a second sleeve 704 with an integral locking member. It is understood that the first sleeve 702 is similar to the first sleeve 32 of the previous embodiments, and the second sleeve 704 is similar to the second sleeve 34 of the previous embodiments. The general structure of the connector 700 is similar to the connectors 10,600 as previously described.

As discussed with respect to prior embodiments, a first sleeve member 702 has a first end preferably attached to a first container and a second end 706 preferably associated with and operably connected to the second sleeve member 704. Here, the second end 706 includes a flange 708, or stop. A piercing member 710 is positioned within the first and second sleeves 702, 704. The first sleeve member 702 preferably includes an sleeve groove 712 and a sleeve ridge 714 which generally extend about an exterior surface of the first sleeve 702. The sleeve ridge 714 may be considered a radial extension or radially extensive member. The sleeve groove 712 is spaced from the sleeve ridge 714 along the axial length of the first sleeve 702. The first sleeve 702 preferably also includes an elevated sealing surface 716 which is generally in contact with a sealing member 742, preferably an o-ring, similar to the structure described in previous embodiments.

The second sleeve 704 is associated with the first sleeve 702 and is arranged so the sleeves 702, 704 may move axially with respect to one another from an inactivated position to an activated position. The second sleeve 704 preferably includes a sleeve rib 720 proximate to a first end 722. The sleeve rib 720 may also be considered a radial extension or a radially extensive member. The second sleeve 704 also preferably includes a sealing surface 724 which contacts the o-ring and provides a hermetic seal between the first sleeve 702 and the second sleeve 704 when the connector device 700 is in the inactivated position as shown in FIG. 37. The sealing surface 724 is sized such that a seal is maintained by the o-ring between the sleeves 702, 704 until after the ridge 714 and rib 720 pass one another as described below.

The sleeve ridge 714 on the first sleeve 702 in conjunction with the sleeve rib 720 of the second sleeve 704 together form a locking member 726. The locking member 726 prevents the premature activation of the connector device 700 by providing mechanical resistance to the axial movement of the first sleeve member 702 and second sleeve member 704. The sleeve ridge 714 and sleeve rib 720, forming the locking member 726, are coactive to provide a resistance force that prevents relative movement of the sleeves 702, 704. The structure of the members 714, 720 will provide a predetermined resistance force. This resistance force can be altered based on the structure of the members 714, 720. The locking members 714, 720 are disassociated when a force greater than the resistance force is provided to the sleeves 702, 704 wherein the sleeves 702, 704 are movable to the activated position. The first sleeve 702, therefore, has a localized portion that generates a force in cooperation with a member on the second sleeve 704 when the sleeves 702, 704 are moved from the inactivated position. The localized portion and member, upon engagement, provide a localized and distinct force at the engagement point at the sleeves 702, 704 to prevent premature activation of the device. The second sleeve 704 could also be considered to have a localized portion that cooperates with a member on the first sleeve 702.

Figure 43:
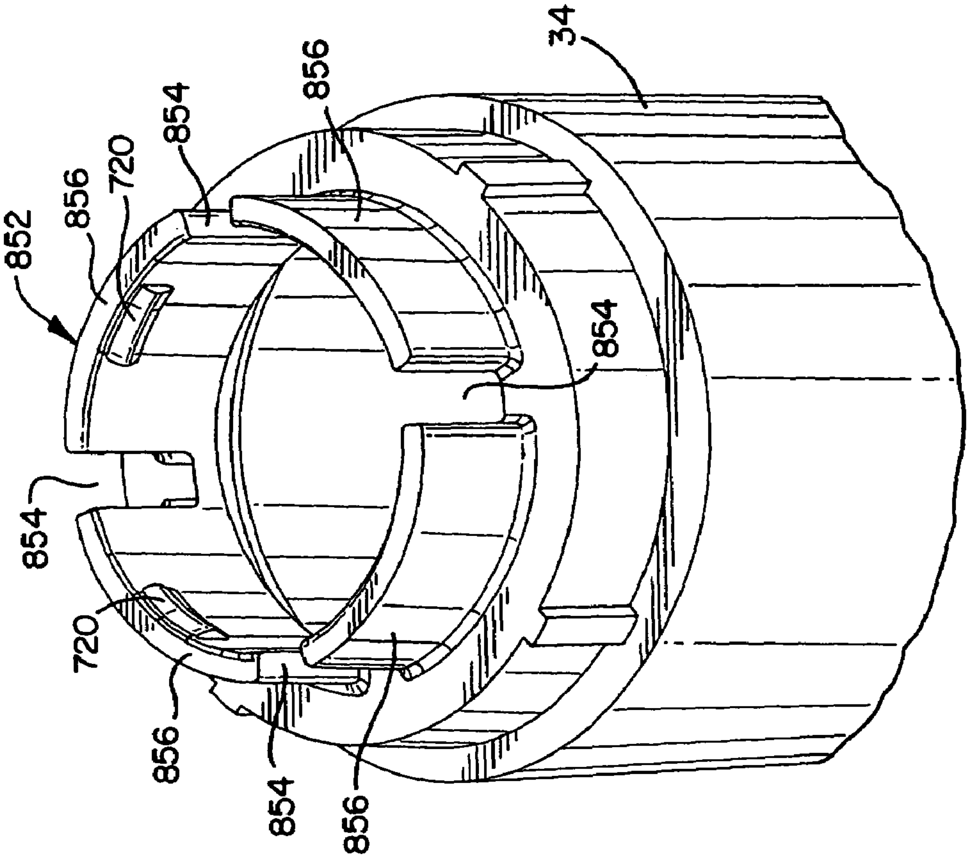
FIG. 43 is partial perspective view of the second sleeve according to another embodiment of the present invention.
Figure 42:
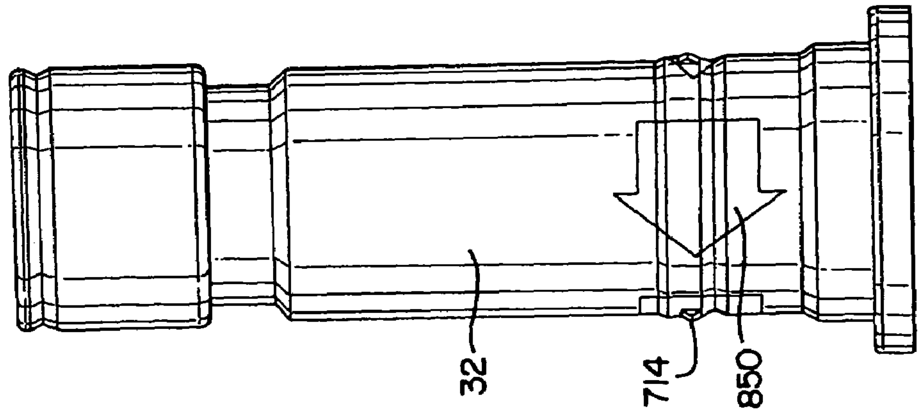
FIG. 42 is an front elevation view of the first sleeve according to another embodiment of the present invention.

It is further understood that the sleeve ridge 714 and sleeve rib 720 can be complete annular structures on the respective sleeves 702, 704, thus extending around a full circumference of the sleeves 702, 704. It is also understood that one or both of the sleeve ridge 714 and sleeve rib 720 could not extend around a full circumference and be segmented. For example, FIG. 42 shows a pair of segmented sleeve ridges 714. Also, FIG. 43 shows segmented sleeve ribs 720. If both structures 714, 720 are segmented, additional structure is provided with the sleeves 702, 704 to prevent unwanted rotation of the sleeves 702, 704 to assure proper alignment such that the ridge 714 and rib 720 would be in a position to engage one another. In one preferred embodiment, the sleeve ridge 714 is a segmented structure such as shown in FIG. 42 and the sleeve rib 720 is a full annular rib 720 on the second sleeve 704. It is further understood that the ridge 714 and rib 720 could be referred to as detents, projections, extensions, bumps, protrusions or protuberances.

The connector device 700 of the present embodiment is preferably activated, in the same manner as described in conjunction with FIG. 29 above. This includes positioning an attached second container 14 on a solid surface and applying a force to structure associated with a first container, preferably a port connector flange, such that a first attached container 12 and first sleeve 702 move in the direction of the second container 14 and into an activated position. The locking member 726 of the present embodiment provides resistance and increases the amount of force required to move the sleeves 702, 704 from an inactivated position to an activated position wherein fluid can flow between the containers 12, 14. The amount of force required to activate the connector device 700 is preferably in the range of approximately 25 lbs. or less. In one preferred embodiment, the activation force is in the range of 10-12 lbs. The activation force must overcome the resistance force provided by the locking member 726.

As shown in FIGS. 37-39, when sufficient force is applied to the port connector flange, or other structure for receiving such force, the sleeve rib 720 of the second sleeve 704 is moved out of the annular groove 712 and moves towards the sleeve ridge 714 of the first sleeve 702. The annular ridges 714 and ribs 720 are preferably sloped, and as the ridges 714 and ribs 720 are moved on top of one another the material of the sleeves 702, 704 flexes. The resistance increases as the highest point of each member, or extension, is moved towards the highest point of the other until a point of no return is reached, and the members become disassociated and move past one another. The point of no return is that point at which the two zeniths of the ridge 714 and ribs 720 are aligned, as shown in FIG. 38. Preferably, it is extremely difficult or impossible for a user to stop the axial motion of the two sleeves 702, 704 relative to one another once that point has been reached.

When the connector device 700 is moved from an inactivated position to an activated position, it goes through a transitional position. The transitional position includes any position wherein the sleeves 702, 704 have been moved towards the activated position from the inactivated position, but have not yet reached the point of no return. It is preferable that the hermetic seal between the first sleeve member 702 and the second sleeve member 704 is maintained throughout the entire transitional position. The hermetic seal is preferably provided by the sealing member 742 positioned between the first and second sleeve members 702, 704. The seal formed by the o-ring is preferably maintained throughout the transitional position by keeping the o-ring in contact with the sealing surface 716 of the first sleeve 702 and the sealing surface 724 of the second sleeve 704 throughout the transitional position. The o-ring slides along the sealing surface 724 when the first sleeve 702 is moved axially with respect to the second sleeve 704. Some movement of the o-ring along sealing surface 716 may also occur. The length of the sealing surface 724 is preferably greater than the distance traveled by the first sleeve 702 relative to the second sleeve 704 in going from the inactivated position to the point of no return. Therefore, throughout the movement of the sleeves 702, 704 through the transitional position, the hermetic seal is preserved by the o-ring. It is not until the sleeve ridge 714 of the first sleeve 702 and the sleeve rib 720 of the second sleeve 704 have moved past one another that the o-ring moves clear of the sealing surface 724, and the hermetic seal at the junction of the first and second sleeves is broken. Accordingly, as shown in FIGS. 37-41, when the sleeves 702,704 are in the inactivated position, the sleeves 702, 704 have a first relative position. The o-ring provides a seal between the sleeves 702, 704 in this position. The extension members 714, 720 are coactive to provide a force to resist displacement of the sleeves 702, 704 from the first relative position. When an activation force is provided to overcome the resistance force, the sleeves 702, 704 are displaced from the first relative position wherein the members 714, 720 are disassociated, and wherein the seal provide by the o-ring is broken.

Figure 41:
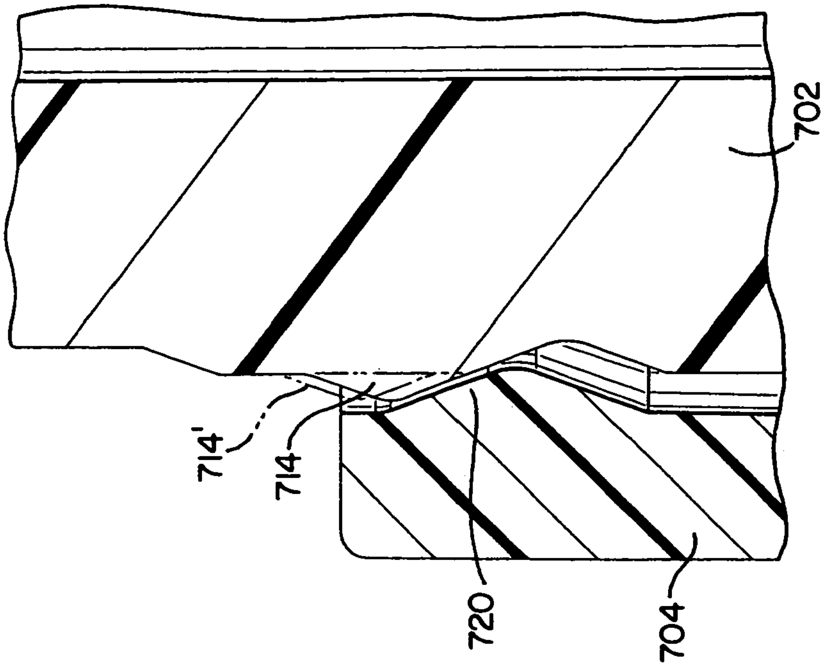
FIG. 41 is an enlarged partial cross-sectional view of the first and second sleeves of the connector device of FIG. 50.
Figure 40:
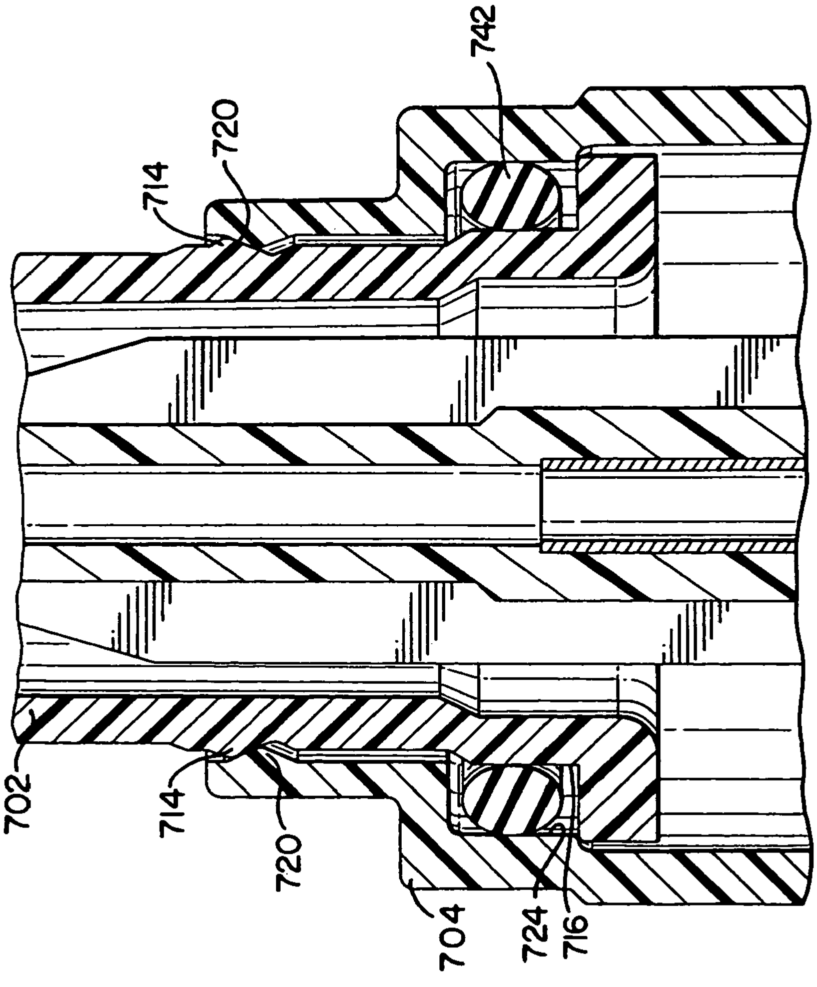
FIG. 40 is a partial cross-sectional view of first and second sleeves of the connector device according to another embodiment of the present invention, the connector device being in an inactivated position.

FIGS. 40 and 41 disclose an additional alternate embodiment of the sleeves 702, 704 having the integral locking member 726. Identical reference numerals are used in describing the alternate embodiment of FIGS. 40 and 41. As previously discussed with respect to the embodiment of FIGS. 37-39, the sleeve groove 712 and sleeve ridge 714 on the first sleeve 702 are axially spaced apart a short distance. Thus, in the inactivated position, the sleeve rib 720 on the second sleeve 704 is received in the sleeve groove 712 and is therefore spaced from the annular ridge 714. In such configuration, the sleeves 702, 704 must move a short distance before the sleeve rib 720 begins to engage the sleeve ridge 714. As shown in the alternate embodiment of FIGS. 40 and 41, the sleeve ridge 714 is moved axially along the first sleeve 702 towards the end of the first sleeve 702 closer to the gripper assembly end of the second sleeve 704. In this configuration, the ridge 714 is closer to the sleeve groove 712. FIG. 41 shows an enlarged view of the alternate position of the sleeve ridge 714 in solid lines while the position of the sleeve ridge of the embodiment of FIG. 37 is shown in phantom lines, and designated with the reference numeral 714'. Thus, in the inactivated position, axial space between the sleeve ridge 714 and the sleeve rib 720 is generally eliminated. The respective surfaces of the ridge 714 and the rib 720 are in surface-to-surface engagement. In this configuration, the sleeve ridge 714 and sleeve rib 720 begin engagement substantially simultaneously once force is applied to move the sleeves 702, 704 from the inactivated position to the activated position. Thus, the locking member 726 operates to prevent premature activation of the device quicker than in the embodiment of FIGS. 37-39 where the sleeves 702, 704 move a short distance before engagement of the ridge 714 and rib 720. Once engaged, however, the overall operation of the sleeve ridge 714 and the sleeve rib 720 is the same as described above. As previously discussed, it is understood that the stop surface 64 in the form of the second ledge 64 on the second sleeve 34 could be removed if desired. The engagement of the sleeve ridge 714 and sleeve rib 720 will prevent any premature movement of the sleeves 32,34 until desired. It is also understood that the ridge 714 and rib 720 could be on opposite sleeves 702, 704.

Figure 40A:
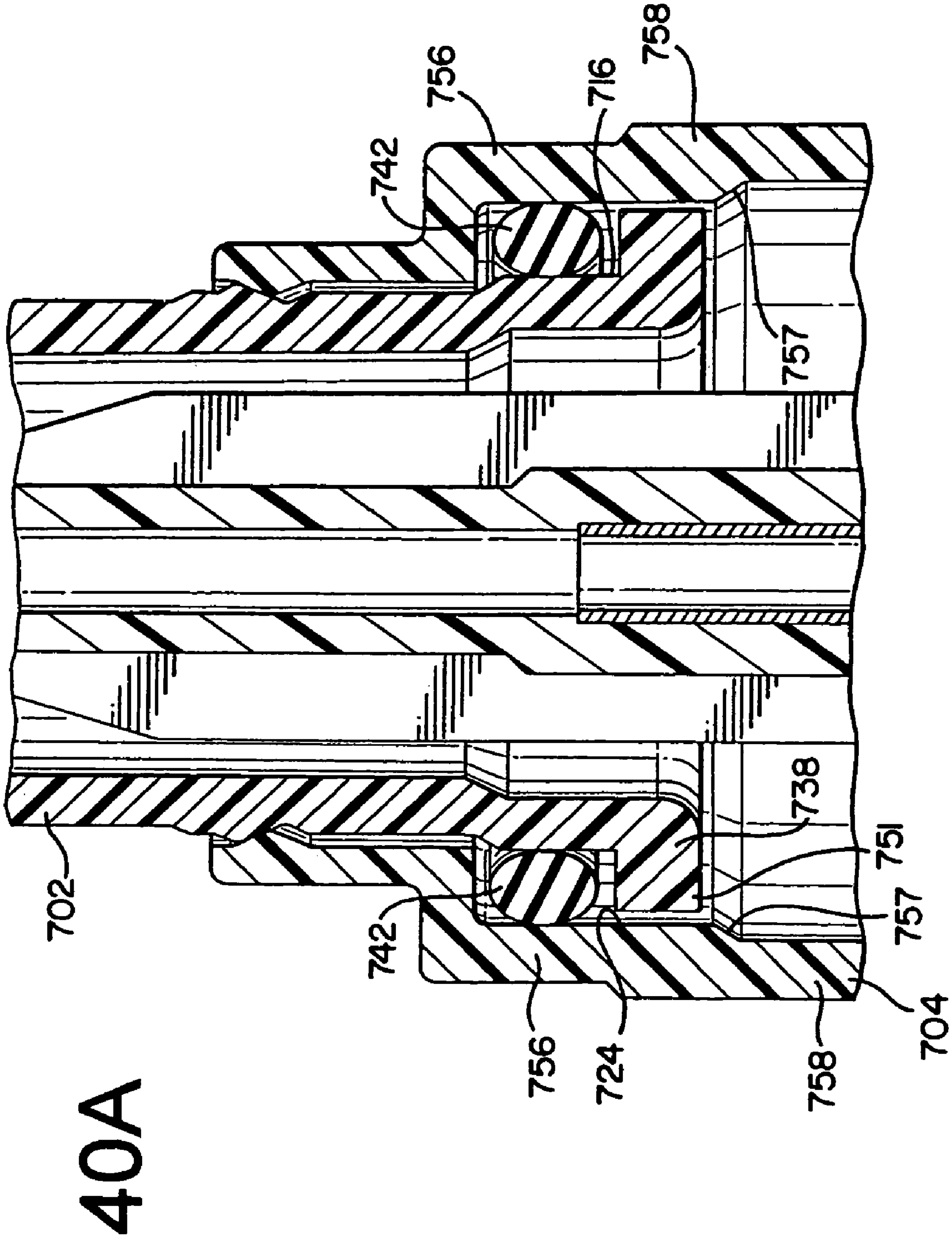
FIG. 40A is a partial cross-sectional view of the connector device of FIG. 40, the device being in an inactivated position, and the sleeves having an alternate structure according to another embodiment of the present invention.

FIG. 40A shows the connector device of FIG. 40 but wherein the sleeves 702, 704 have an alternate construction. In this particular preferred embodiment, the sealing surface 724 on the inner surface of the second sleeve 704 is elongated slightly as compared to the sealing surface 724 on the second sleeve 704 shown in FIG. 40. As with the second sleeve 34 of the previous embodiments, the second sleeve 704 of FIG. 40 can be considered to have a first section 756 and a second section 758. The second section 758 has a larger diameter and larger radial dimension than the first section 756. As opposed to a distinct ledge, such as the ledge 64 of the previous embodiments, the inner surface of the second sleeve 704 has a tapered lead-in surface 757 that transitions the second sleeve 704 between the first section 756 and the second section 758. In this structural configuration, a flanged second end 738 of the first sleeve 702 is reduced in its radial dimension such that the flanged second end 738 accommodates the longer sealing surface 724. As in previous embodiments, the o-ring 742 is compressed between the sealing surface 716 of the first sleeve 702 and the sealing surface 724 of the second sleeve 704 when the sleeves 702, 704 are in the inactivated position. Because of the longer sealing surface 724 in FIG. 40A, the o-ring 742 provides the hermetic seal for a longer period of time than in the previous embodiments as the sleeves 702, 704 move from the inactivated position to the activated position. As the sleeves 702, 704 axially move and the o-ring 742 moves from the first section 756, past the tapered surface 757, and to the larger second section 758, the seal provided by the o-ring 742 is then broken similar to the previous embodiments. It is understood that the sealing surface 724 can be varied as desired such that the o-ring 742 provides the hermetic seal between the sleeves 702, 704 for an amount of time as desired during the activation process.

As discussed above, several structures are possible and contemplated to prevent premature activation of the connector device. It is understood that these structures could be combined as desired in alternative embodiments of the device. For example, a connector device could include both the locking clip of FIGS. 25-30 and the sleeve ridge/sleeve rib structures shown in FIGS. 37-41. Other combinations are readily apparent.

FIGS. 44-47 show another embodiment of the sealing member 84, used with the connector devices of the present invention, generally designated by the reference numeral 800. The sealing member 800, or septum 800, or vial septum 800, generally has one portion made of rigid material and a collar made of a rubber-like material. In one preferred embodiment, the portions of the septum 800 are formed simultaneously together in a two-shot injection molded process. It is understood, however, that other processes can be used to connect the separate portions including an insert molding process. Adhesives or an interference fit could also be used. As shown in FIGS. 44-47, the septum generally has a base 802 and a membrane 803.

As generally shown in FIGS. 44 and 45, the base 802 is generally disk-shaped. The disk or base 802 has a first surface 804 and a second surface 806. The first surface 804 faces into the connector 10 and the second surface 806 faces the container to be attached to the connector 10. The base 802 has an opening 808 therethrough, preferably in a center of the base 802. The opening 808 defines an inner surface 810 on the base 802. The base 802 further has an annular ring 812 extending from the second surface 806 of the base 802 and around the center opening 808. The annular ring 812 is tapered wherein a distal end has a rounded protrusion 814. The annular ring 812 is capable of forming a fluid tight seal with the closure 20 of the vial 14 as described previously with respect to the septum shown, for example, in FIGS. 22-24. This embodiment of a septum is also capable of forming a fluid tight seal with the closure 20 of the vial 14 in a similar manner.

The membrane 803 is positioned in the center opening 808 and closes the opening 808. The membrane 803 has a generally planar section 816 with a depending leg 818. The leg 818 is connected to the inner surface 810 of the base 802.

As further shown in FIGS. 46-47, the base 802 preferably includes a recess 820. A collar 822 is preferably positioned in the recess 820. The collar 822 is preferably formed of a rubber-like material which is relatively less rigid and more flexible than the material of the base 802. The collar 822 has a ridge 824 which facilitates positioning the septum 800 in the connector 10. It is further understood that the second surface 806 at the outer periphery is generally planar. This surface mates with a generally planar surface of a bottom of a finger assembly 92. This can be seen, for example, in FIG. 51, which structure and operation will be described in greater detail below.

As discussed, the septum 800 is formed in one preferred embodiment by a two-shot injection molding process. The base 802 of the septum is a rigid plastic material. The collar 822 of the septum 800 is a softer rubber-like material. The components are molded together simultaneously in a two-shot injection molding process as is known in the art. The septum 800 of this embodiment therefore possesses the rigidity from the plastic material that provides rigidity to the septum 800 when it is pierced, and also posses the softness or flexibility of the rubber-like material where it contacts the connector to provide a fluid tight seal.

In yet another embodiment of the present invention, the device 10 of the present invention can be equipped with features that provide a generally consistent activation force among devices manufactured by an automated process.

In one feature, the device 10 can be configured to reduce friction between the sliding sleeves 32,34 and therefore, allow the first sleeve 32 and the second sleeve 34 to slide more easily with respect to one another. It is understood that this feature can also be utilized in the sleeves of the other embodiments such as sleeves 702, 704 of FIGS. 37-41. As discussed, in a preferred form of the invention, the first sleeve 32 and second sleeve 34 are formed from plastic in a plastic injection molding process. A lubricant additive can be used in conjunction with one or both of the first sleeve 32 and the second sleeve 34. In this embodiment, the lubricant additive is used in the injection molding process used to form the sleeves 32,34. Use of the lubricant additive further allows moderation of the activation force of the device.

For example, as shown in FIG. 42, the first sleeve 32 can be injected molded wherein a lubricant additive can be added to the injected molded material. In one preferred embodiment, the sleeves 32,34 are formed from a polycarbonate material. This functional lubricant is initially blended with the plastic resin used to form the sleeve 32 and molded at a high temperature to deliver the desired surface lubricity. The lubricant additive may bloom towards the plastic surface over time after blending and molding. This blooming kinetics dictating plastic lubricity level over time are controlled by lubricant molecular size, lubricant loadings, environmental temperature and plastic substrate chemistry. The lubricant additive loading may generally vary from 1 to 5 wt. % to yield the desired lubricity while not compromising material mechanical properties of the sleeves 32,34.

In one preferred embodiment, the first sleeve 32 is injected molded wherein a plastic lubricant additive is used such as Ultra High Molecular Weight (UHMW) polysiloxane. The lubricant additive will generally help in the sliding movement of the sleeves 32,34. In particular, the surface lubricity is useful for the portions of the sleeves 32,34 that engage one another such as the sleeve ridge 714 and the sleeve rib 720 as described above. Consequently, the sleeves 32,34, 702, 704 slide with respect to each other more uniformly therefore providing a more uniform activation force.

The polysiloxane lubricant used can be any known organosiloxane, or its chemical derivatives, and is preferably a polyalkylsiloxane, more preferably polydimethylsiloxane, and even more preferably ultra-high molecular weight ("UHMW") polydimethylsiloxane. The polysiloxane may comprise a high molecular weight polysiloxane (e.g., multibase siloxane masterbatch), low molecular silicone oil (e.g., fluorinated silicone) and mixtures thereof. Other suitable polysiloxanes include vinyl terminated siloxanes, hydroxyl terminated siloxanes, hydride terminated siloxanes, silanol terminated siloxanes, aminopropyl terminated siloxanes, carbinol(hydroxyl) siloxanes, acryloxy terminated siloxanes, polydimethylsiloxanes and mixtures thereof. In other embodiments, the polysiloxane comprises polymethylphenylsiloxane, polydiphenylsiloxane, vinylmethylsiloxane, vinyldimethyl-siloxane, vinylmethoxysiloxane, and mixtures thereof.

It is understood that other different types of plastic lubricant additives can be used in the present invention. The lubricant additive could include fatty amides (e.g., eurucamide), metallic stearates (e.g., zinc stearate), waxes/powders (e.g., PTFE or polyethylene wax), esters (e.g., sucrose ester, glycelerol ester), high molecular weight polysiloxane, low molecular silicone oil (e.g., fluorinated silicone) and process oil (e.g., mineral oil) and blends thereof. The sleeves 32,34 can be also be formed from a variety of different plastics, including polycarbonate. The lubricant additive could take various different physical forms such as a powder, bead, pellet, or liquid depending on process, condition or material requirements of the component. In addition to an injection molding process, other processes can be used such as compression and transfer molding and casting and Reaction Injection Molding (RIM). Extrusion methods could also be used.

Using the plastic lubricant additive provides several advantages. First, the surface lubricity assists in the sliding movement of the sleeves 32,34, 702, 704, particularly, for example, during the interaction of the sleeve ridge 714 and sleeve rib 720, providing a more uniform activation force. The lubricant additive further allows for moderating the activation force. Using the lubricant additive during the injection molding process is simple and efficient. This process further accelerates part assembly and lowers manufacturing costs. The lubricant additive, such as UHMW polysiloxane, is essentially non-migratable, thus minimizing contamination and functionality degradation concerns. Using the lubricant additive in the injection molding process also provides complete and uniform surface coverage. This process also eliminates the need for a solvent such as in silicone coating, making the process more environmentally friendly.

It is further understood that the plastic lubricant additive could be used in just one of the first sleeve 32 and the second sleeve 34. Lubricant additives could also be used in both sleeves 32,34 if desired. It is further understood that the plastic lubricant additive could be used in other components of the device 10. In one example, a lubricant additive could be utilized in the process forming the plastic spike of the piercing assembly. Alternatively, the plastic spike may have a silocone coating separately applied. In either case, the lubricant can help in facilitating spike insertion into the first container 12.

Lubricants can also be associated with the sleeve 32 via other methods. For example, as shown in FIG. 42, an inked segment 850 can be applied to the sleeve 32 wherein the ink contains a lubricant. The inked segment 850 can be applied at different locations or spaced about the sleeve 32. As shown in FIG. 42, the inked segment 850 is applied over the sleeve ridge 714. In another embodiment, a lubricant can be sprayed or otherwise deposited onto the sleeve 32.

FIG. 43 illustrates another feature to assist in providing a more uniform activation force. As shown in previous embodiments, the second sleeve 34 has an end flange 852 that typically is in the form of a solid annular ring. In the embodiment shown in FIG. 43, the end flange 852 has a discontinuous annulus. In particular, the end flange 852 has a notch 854 dividing the end flange 852 into flange segments 856. In one preferred embodiment, the end flange 852 has four notches 854 and four end flange segments 856. The notches 854 allow the end flange segments 856 to deflect more easily when the annular ridge 714 and annular rib 720 engage one another as the device 10 is moved from the inactivated position to the activated position. Thus, the discontinuous annulus deflects when the ridge 714 and rib 720 become displaced wherein the discontinuity enhances radial deflectability. It is further noted, that in this embodiment, the sleeve rib 720 is segmented and does not extend around a full circumference of the second sleeve 34.

Figure 48:
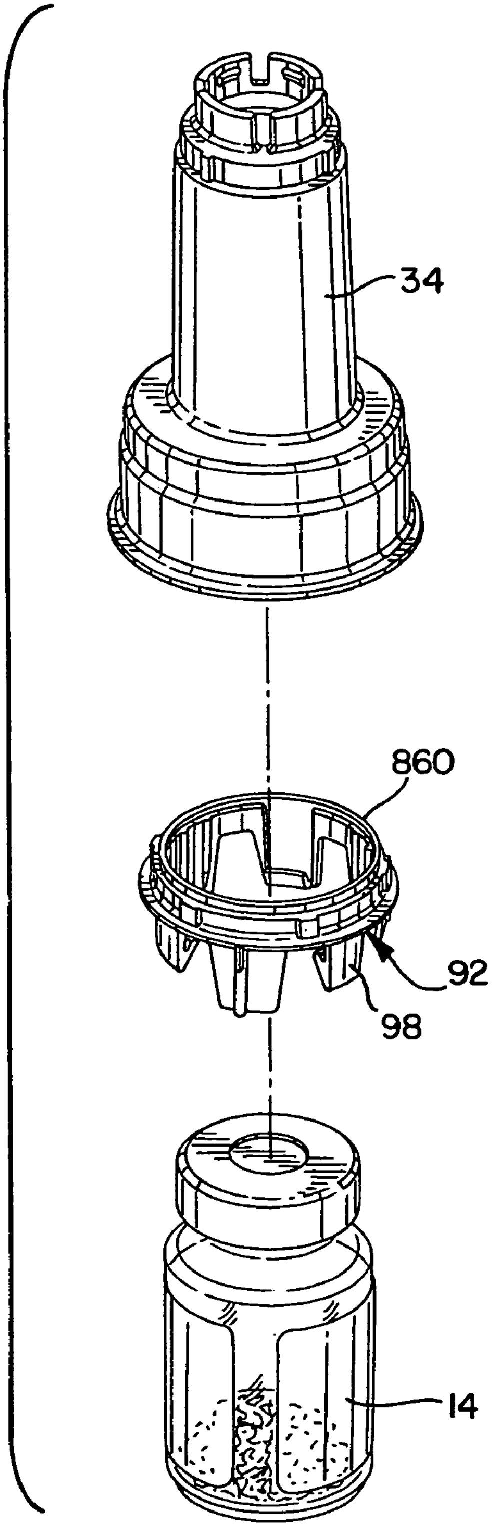
FIG. 48 is a partial exploded perspective view showing the second sleeve, gripper assembly and vial.
Figure 49:
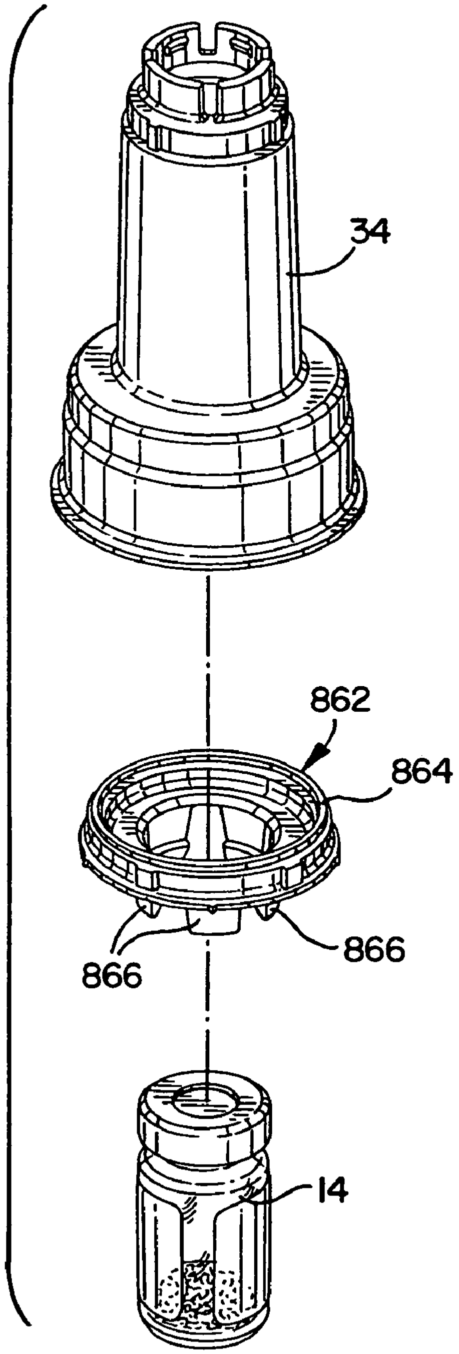
FIG. 49 is a partial exploded perspective view showing the second sleeve, an alternative portion of the gripper assembly and alternate vial.

FIGS. 48 and 49 disclose another feature of the invention wherein the reconstitution device 10 can be configured to accept one of a plurality of differently sized containers, or specifically, a number of differently sized vials 14. The device 10 can be configured with alternate gripper assemblies 28 that utilize different finger assemblies 92. In general, a finger assembly 92 can be used that is dimensioned to conform to the dimensions of the second container 14 to be used with the device 10. FIG. 48 shows an exploded view of the second sleeve 34 and finger assembly 92 consistent with the previous embodiments. In these embodiments, the finger assembly 92 is sized to generally receive vials 14 that are 20 mm in size. The finger assembly 92 has a base portion 860 that is connected to the second sleeve 34 as described above. FIG. 49 shows an exploded view of the second sleeve 34 but utilizing an alternative finger assembly 862. The finger assembly 862 has a generally identical base portion 864 as the finger assembly 92 shown in FIG. 48, and is connected to the second sleeve 34 as generally described herein. Any of the finger assemblies can be configured with the appropriate structures to be used with any of the sealing members 84 disclosed herein including the sealing member 84 or vial septum 800 of FIG. 44. The finger assembly 862 in FIG. 49, however, has different structure that can receive a vial 14 of a different size from FIG. 48. In this particular embodiment, the finger assembly 862 has three segmented fingers 866 as opposed to the six segmented fingers 98 of the finger assembly 92 of FIG. 48. The three segmented fingers 866 are sized and spaced to receive a vial 14 smaller than the vial 14 in FIG. 48. In a preferred embodiment, the finger assembly 862 of FIG. 49 is sized to receive vials 14 that are 13 mm in size. Thus, the finger assembly 92 of FIG. 48 may be considered a primary second attaching member and the finger assembly 862 of FIG. 49 may be considered a secondary second attaching member. Each second attaching member is adapted to attach to containers of different sizes. The second sleeve or gripper assembly can accept either one of the finger assemblies.

This feature allows devices 10 to be generally mass-produced and that are generally identical, but with a change in a single part, the finger assembly 92, 862, the device can then accept vials of different sizes. While two different sized finger assemblies 92, 862 and vials 14 are shown in FIGS. 48 and 49, it is understood that multiple other finger assemblies can be utilized to accept vials 14 of other sizes.

Figures 50, 51:
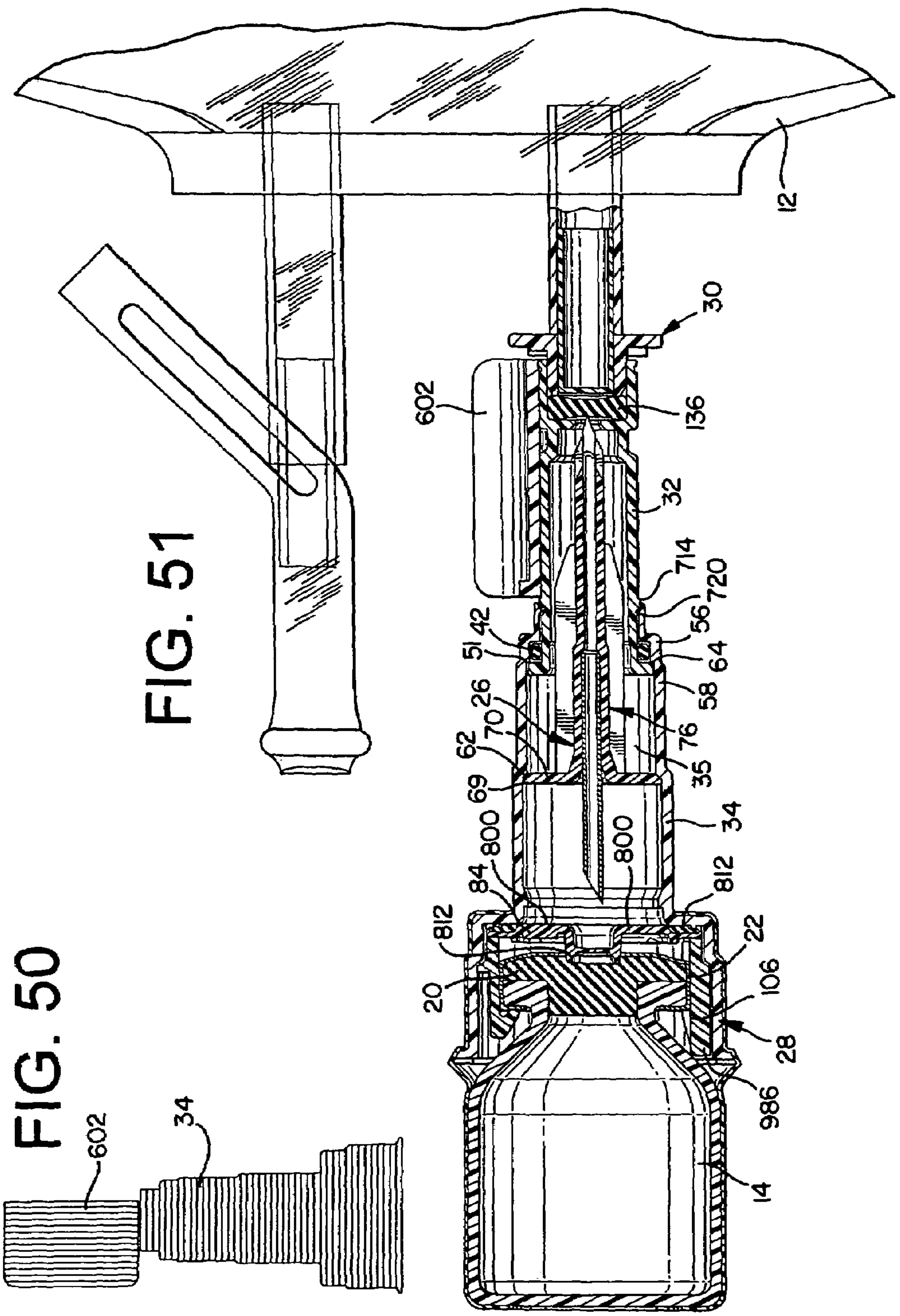
FIG. 50 is a color schematic view of the locking clip and second sleeve.
FIG. 51 is a partial cross-sectional view of the connector device of the present invention utilizing the locking clip of FIG. 25, and having a drug vial fixedly secured to the connector device, the connector device attached to the flexible container and being in an inactivated position.

FIG. 50 discloses another feature of the present invention regarding color indication. FIG. 50 shows a color schematic view of the second sleeve 34 and the locking device 602 of FIG. 25. In one preferred embodiment, the second sleeve 34 has a color that is perceptively different from a color of the locking device 602. This gives a user an indication that the device 10 is not in the activated position. In a further feature, the first sleeve 32 may also have a color that is perceptively different from both the second sleeve 34 and the locking device 602.

FIGS. 51-57 disclose an additional general operational sequence of another preferred embodiment of the connector device 10 of the present invention. The connector device 10 of this embodiment has generally similar structure, but utilizes, in combination, several of the different features of the different embodiments described above. For example, the general structure of the connector device is similar to the embodiment of FIGS. 1-8 and 21 A-D. The connector device of FIGS. 51-57, however, also utilizes the locking clip of FIG. 25, the ridge/rib structure of FIGS. 37-41, and the septum of FIGS. 44-47. For simplicity, reference numerals of the first embodiment are generally used with additional reference to reference numerals used to describe these other structures and features of the other embodiments. It is appreciated that the connector device of FIG. 51 is sterilely connected to the flexible bag 12 and the vial 14 to form a reconstitution assembly, generally referred to with the reference numeral 1. (See also FIG. 29). It can be appreciated that with such sterile connection, without breaching the hermetic seal of the piercing member, reconstitution assemblies 1 can be manufactured in pre-packaged form and inventoried by users for later use. It is also understood that the reconstitution assembly 1, based on the materials used for the containers 12, 14 and the connections made between the device 10 and containers 12, 14, the assembly 1 does not require an over-pouch to contain the entire assembly when the assembly 1 is inventoried for later use.

FIG. 51 shows the reconstitution assembly 1 wherein the connector device 10 is connected to the flexible container 12 and the vial 14. The membrane tube of the port connector assembly is suitably solvent bonded to the port tube of the flexible container 12 as can be appreciated by one skilled in the art. It is further appreciated by one skilled in the art that the polymeric membrane tube of the port connector assembly is suitably solvent bonded to the plastic port snap. The vial also has a shrink wrap element positioned around the vial 14 and portion of the second sleeve 34. While the element is not shown in FIGS. 55-57, it is understood that the shrink wrap element will remain on the assembly during the entire reconstitution process. In this embodiment, the portion of the gripper assembly forms part of, or is integral with the second sleeve 34. It is further noted that as the vial septum 800 is utilized, the finger assembly 92 has the generally planar base portion that mates with the generally planar second surface 806 of the vial septum 800. The first annular rim 108 engages the collar 824 of the vial septum 800.

Figure 52:
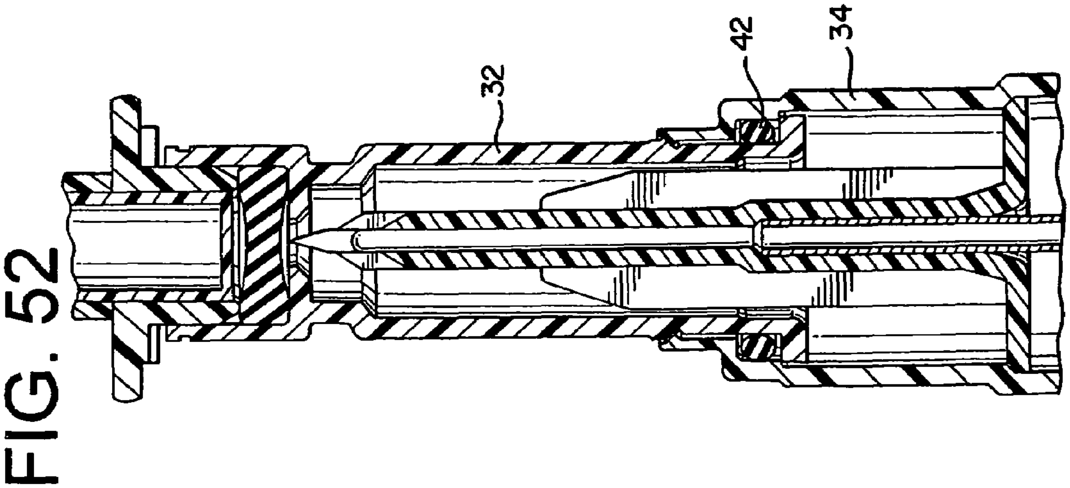
FIG. 52 is a partial cross-sectional view of the connector device of FIG. 51 and utilizing the sleeves of FIG. 40, wherein the connector device is in the inactivated position.

FIG. 51 also shows the connector 10 in its inactivated position where the connector 10 is in its most elongated state. The locking device 602 is positioned over the first sleeve 32 to assist in preventing premature activation. (See also FIG. 29). In this inactivated position, and as shown in FIG. 52, the sleeve ridge 714 is in general engagement with the sleeve rib 720 to also assist in preventing premature activation. Also in this inactivated position, the stop surface 51 of the first sleeve 32 abuts the stop surface 64 of the second sleeve 34. The hub 70 is maintained between the hub stop surface 69 and the ledge 62. As discussed, the vial 14 has already been inserted into the gripper assembly 28. As such, the standing ribs 106 on the fingers **98*b* indent a side portion of the crimp ring 22 on the vial 14. Thus, the vial 14 is fixedly attached to the connector 10. As further shown in FIG. 51, the annular ring 812 of the septum 800 forms a fluid tight seal over the top of the vial 14. The annular ring 812 is positioned within the target site defined by the crimp ring and does not contact the crimp ring. Thus, a vial 14 can be selectively docked to the connector 10 without piercing the stopper 20 of the vial 14**.

FIGS. 53-56 generally disclose the activation process for the connector 10. Once it is decided by a user that the activation process should commence, the user removes the locking clip 602. As can be understood with further reference to FIGS. 51 and 29, the connector 10 can generally be activated by placing the bottom portion of the vial 14 against, for example a table top. The user can then grasp the flange or ledge 131 of the port connector 30 and apply a downward force to the connector device 10 wherein the sleeves moves axially toward one another. The device 10 could also be activated by holding both sleeves 32,34 and moving the sleeves 32,34 toward one another.

Figure 54:
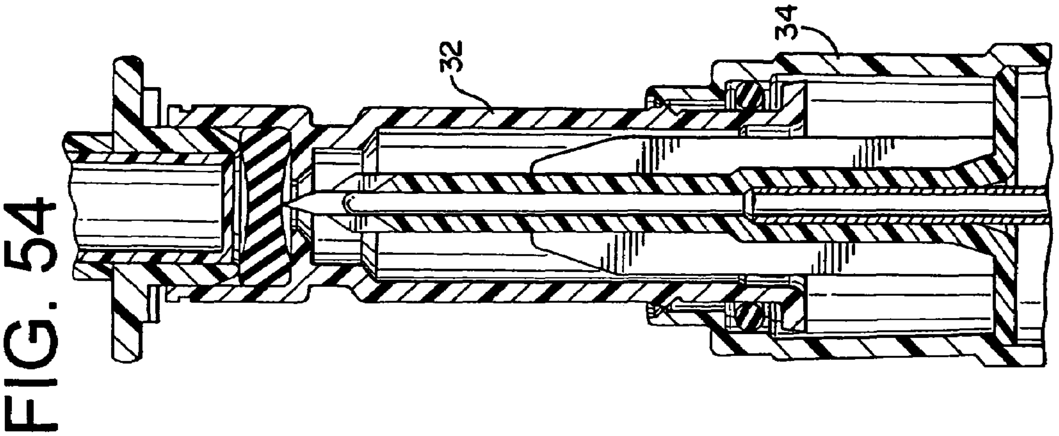
FIG. 54 is a partial cross-sectional view of the connector device of FIG. 52, wherein the connector device is in a further stage of transition from the inactivated position to the activated position.
Figure 53:
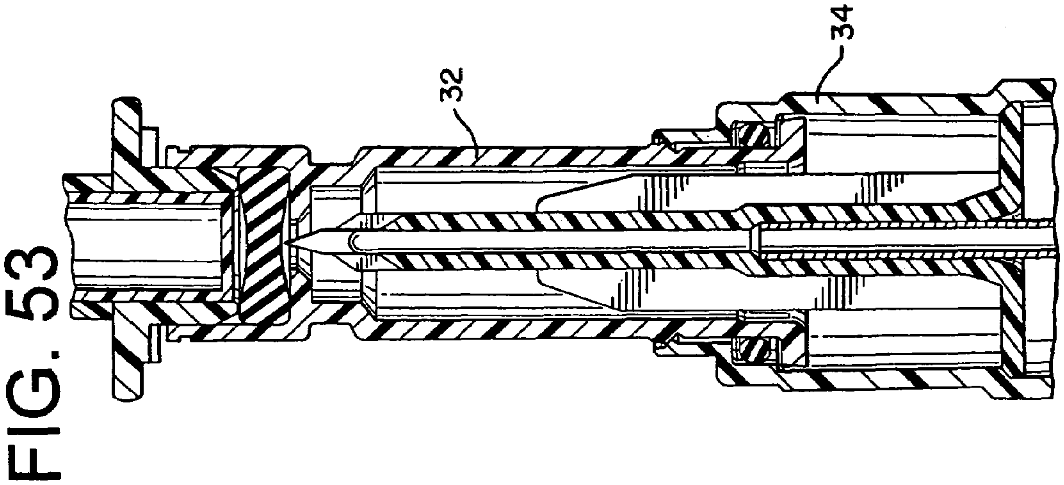
FIG. 53 is a partial cross-sectional view of the connector device of FIG. 52, wherein the connector device is in an initial stage of transition from the inactivated position to the activated position.

FIGS. 53 and 54 show a portion of the first sleeve and second sleeve as the activation process commences. As shown in FIG. 53, upon initial movement of the sleeves 32,34, the rib 720 begins to move over the ridge 714 requiring additional force. FIG. 54 shows an apex of the rib 720 in corresponding relation to an apex of the ridge 714. This position may be generally referred to as a point of no return. The structures of the ridge 714 and rib 720 are such that the device could not statically assume this position. Once the respective apexes pass one another, the force required to further move the sleeves 32,34 is reduced. As discussed, the respective portions of the sleeves 32,34 that provide the sealing surfaces against the o-ring 42 are sized such that the sliding seal provided by the o-ring between the sleeves is maintained until after the sleeve ridge 714 and sleeve rib 720 pass one another during the activation process. Accordingly, the space between the sleeves 32,34 is sized and configured such that the o-ring remains in radial compression to provide the seal between the sleeves 32,34 until the sleeve ridge 714 and sleeve 720 pass one another. Thus, it is further understood that the connector 10 remains hermetically sealed until after the sleeves 32,34 move past the point of no return.

Figure 55:
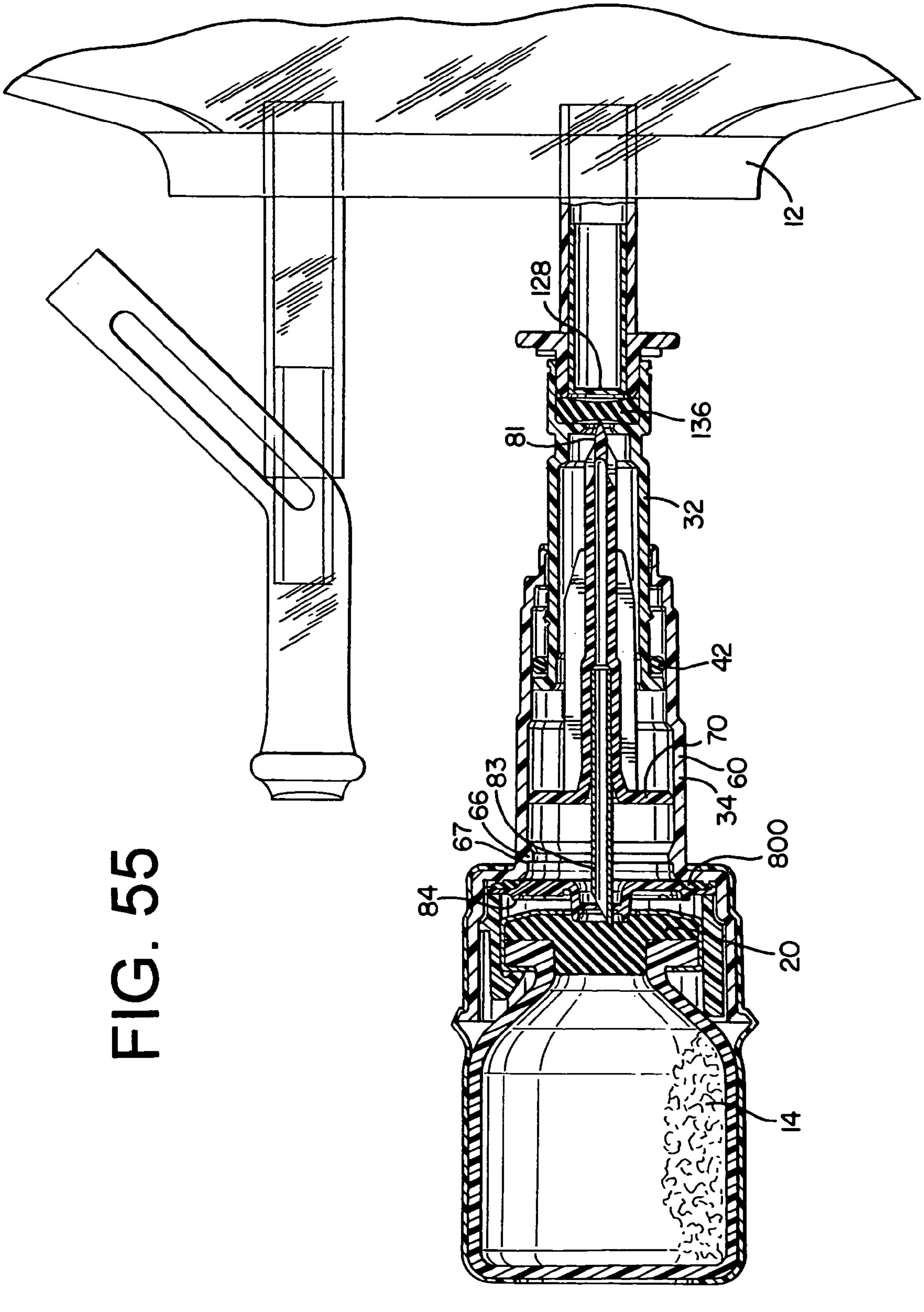
FIG. 55 is a partial cross-sectional view of the connector device of FIG. 51, wherein the connector device is proceeding to the activated position.
Figure 56:
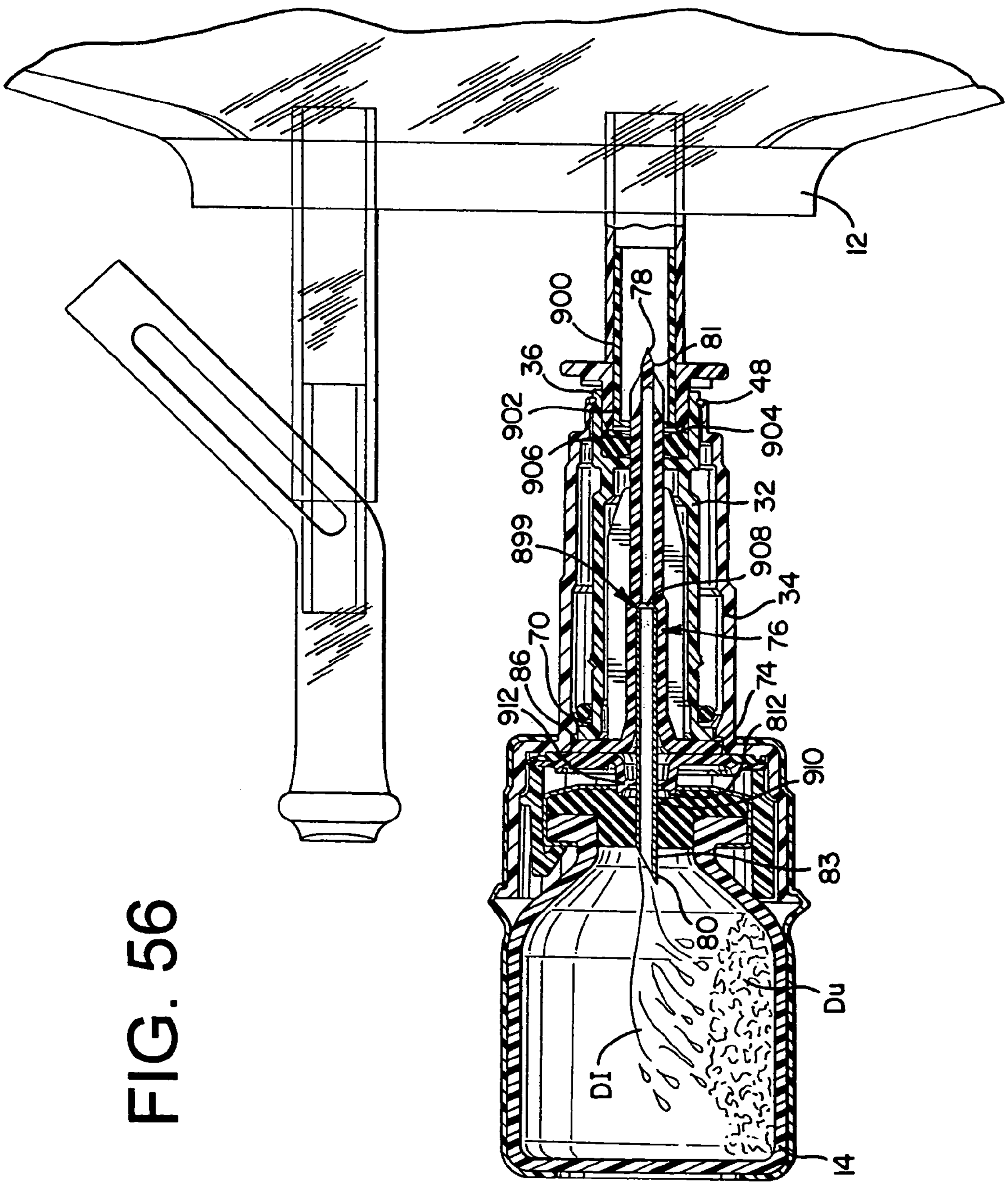
FIG. 56 is a cross-sectional view of the connector device of FIG. 51 in the activated position.

As further shown in FIG. 55, as the second sleeve 34 moves along the first sleeve 32, the plastic spike 81 engages the second sealing member 136. Because of the materials used, the plastic spike 81 will not yet pierce through the second sealing member 136. The friction associated with this engagement will cause the hub 70 to move along the second sleeve 34 wherein the metal cannula 83 will pierce the septum 800 and closure 20 of the vial 14. FIG. 55 shows the metal cannula 83 initially piercing the closure of the vial 14. As shown in FIG. 56, as the second sleeve 34 further moves along the first sleeve 32, the stop surface 74 on the first sleeve 32 moves towards and engages the stop surface 86 of the hub 70 on the piercing assembly 76. The hub 70 thus moves along the third section 60 of the second sleeve 34 wherein the hub 70 rides along the ramped protuberances 66 and eventually passes over the flanges 67. This movement forces the metal cannula 83 at the second end 80 of the piercing assembly 76 to pierce completely through the septum 800 and stopper 20 and thus into the vial 14. The second end of the piercing member 76 now experiences greater friction as it penetrates the stopper 22 of the vial 14. This friction causes the plastic spike 81 at the first end 78 of the piercing member 76 to advance towards the flexible container 12. The plastic spike 81 pierces through the second sealing member 136 and the membrane 128. Accordingly, the structure of device 10 provides for the vial 14 to be pierced before the flexible container 12.

As also shown in FIG. 56, the sleeves 32,34 translate axially wherein the hub 70 advances to against the sealing member 84; also, the first end 48 of the second sleeve 34 proceeds to the first end 36 of the first sleeve 32. This position (FIG. 56) represents the activated position. In the activated position, the metal cannula 83 at the second end 80 of the piercing member 76 is pierced through the stopper 20 of the vial 14, and the plastic spike 81 at the first end 78 of the piercing member 76 is pierced through the second sealing member 136. Thus, fluid communication is established between the flexible bag 12 and the vial 14 through the central fluid passageway 82 of the piercing member 76.

It is understood that when the connector 10 is in the inactivated position, the central passageway 35 is hermetically sealed from an outside environment at one end by the sealing member 84, at an opposite end by the second sealing member 136 and at the interface between the sleeves 32,34 by the sealing member 42. As the vial 14 and second sleeve 34 advance towards the flexible container 12 during the activation process, the volume of the central passageway 35 necessarily decreases thus pressurizing the air located in the central passageway 35. This pressurized air must be relieved before the connector 10 reaches the final activated position. Accordingly, when the o-ring 42 moves past the first section 56 of the second sleeve 34 to the larger diameter of the second section 58 of the second sleeve 34, the sealing member 42 no longer contacts the inner surface of the second sleeve 34 (FIG. 55) thus allowing the pressurized air to be relieved through the junction of the sleeves 32,34.

In the activated position shown in FIG. 56, the diluent DI contained in the flexible container 12 can pass through the piercing member 76 to reconstitute the drug DU contained in the vial 14. In this activated position that establishes fluid communication, a sealed fluid pathway 899 is defined between the flexible bag 12 and the vial 14. The sealed pathway 899 remains sealed although it is subject to forces from a user squeezing the bag 12 to force diluent from the bag 12 and into the vial 14. In one embodiment, a user squeezing the bag 12 can subject the fluid pathway to a pressure of approximately 25 psi. The sealed fluid pathway is generally defined by a plurality of seals along the device 10. A first seal 900 is defined by the solvent bond between the membrane tube of the port connector and the port tube of the flexible bag 12. A second seal 902 is defined between the membrane tube 126 and the snap ring 124 of the port connector 30. A third seal 904 is defined between the snap ring 124 and port septum 136. A fourth seal 906 is defined around the plastic spike 81 by the port septum 136. A fifth seal 908 is defined by the adhesive bond between the metal cannula 83 and the plastic spike 81. A sixth seal 910 is defined by the vial closure 20 around the metal cannula 83. The combination of these seals prevent any leakage of diluent through the connector 10 when the connector 10 is in the activated position. A secondary seal 912 to the seals of the sealed fluid pathway 899 discussed above may be considered to be defined by the annular ring 812 of the septum 800 against the closure of the vial 14. It is understood that the sealed fluid pathway 899 can be defined by more or less of the seals described above.

Figure 57:
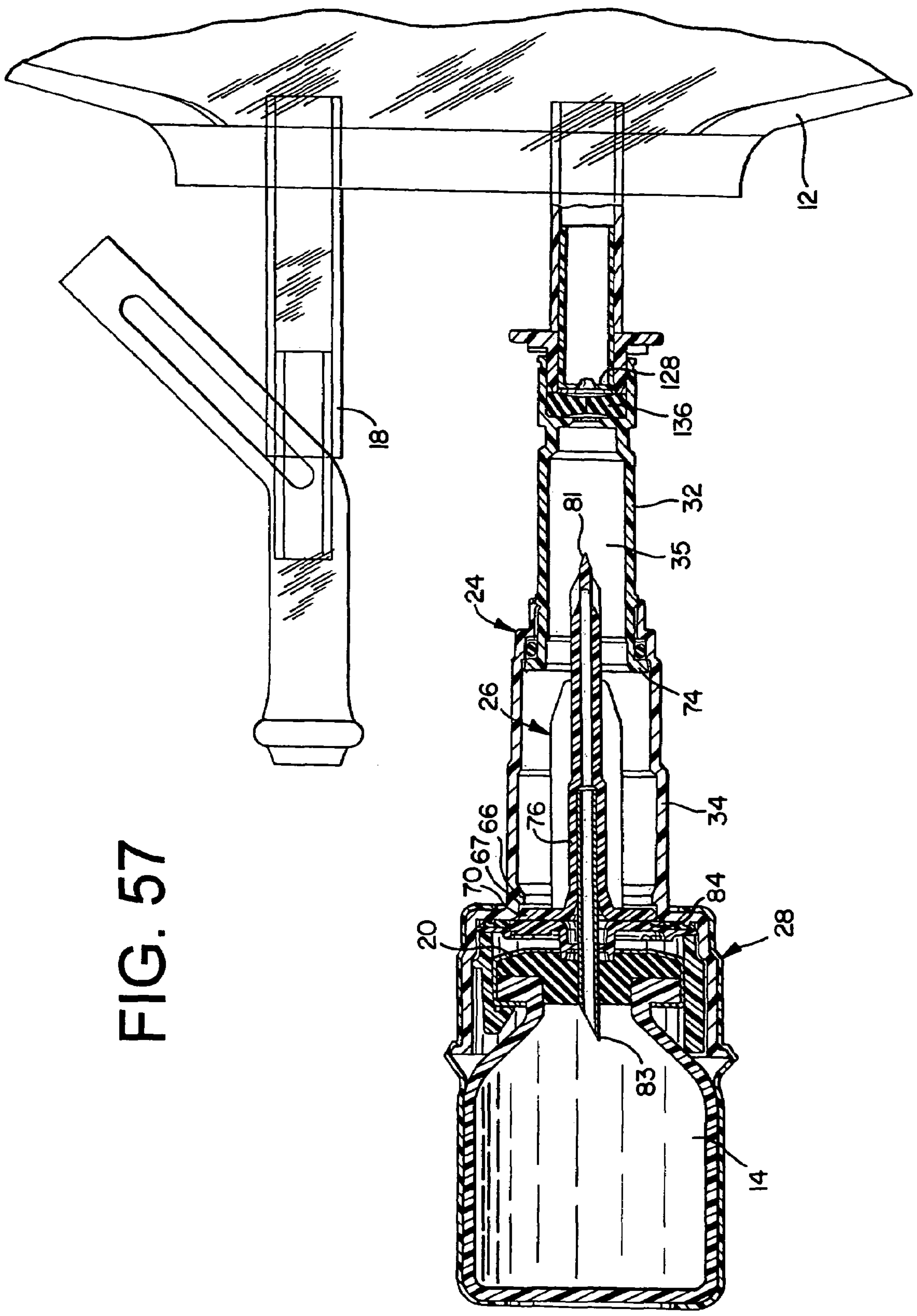
FIG. 57 is a cross-sectional view of the connector device of FIG. 51 in a deactivated position.

As discussed, the diluent from the flexible bag 12 is passed through the piercing member 76 and into the vial 14 to reconstitute the drug contained in the vial 14. Once the drug is reconstituted, the resulting mixture is then passed completely back through the piercing member 76 and into the flexible container 12, the drug vial 14 and second sleeve 34 can be pulled back away from the flexible container 12. As shown in FIG. 57, when the second sleeve 34 is pulled back, the piercing assembly 26 is retained in position by the flange 67 of the ramped protuberance 66. The stop surface 74 of the first sleeve 32, however, does not contact the ramped protuberance 66 and can be retracted. The metal cannula 83 of the piercing member 76 remains within the receiving chamber of the gripper assembly 28 and specifically in the closure of the vial 14. The plastic spike 81 of the piercing member 76 is pulled past the membrane 128 and the second sealing member 136 (FIG. 57). This position is referred to as the deactivated position, or post-reconstitution position. The second sealing member 136 is resilient and forms a seal once the plastic spike 81 passes by, thus preventing any of the resulting mixture from dripping back into the drug vial 14 or passing into the passageway 35 of the sleeve assembly 24. It is further understood that structures other than the ramped protuberance 66 can be utilized to maintain the metal cannula 83 within the vial 14 in the deactivated position. For example, the vial closure 20 or the metal cannula 83 can be structured such that friction or a sufficient interference fit maintains the cannula within the vial 14. The vial septum 84 could also be similarly structured. Additional structure could also be provided to cooperate directly with the cannula 83 rather than the hub 70.

The resulting mixture then resides in the flexible container 12. The resulting mixture can then be delivered to a patient through appropriate administration line sets (not shown) attached to the second port 18 on the flexible container 12.

As described above, the devices of the present invention contain many different features. It is understood that the different features of the several different embodiments described can be interchanged or combined as desired to form a device of the present invention that can also be used in the methods of the present invention.

While the specific embodiments have been illustrated and described, numerous modifications come to mind without significantly departing from the spirit of the invention, and the scope of protection is only limited by the scope of the accompanying claims.

What is claimed is:

1. A connector for establishing fluid communication between a first container and a second container comprising: a first sleeve adapted to be connected to the first container; a second sleeve adapted to be connected to the second container, the second sleeve being associated with the first sleeve and movable axially with respect thereto from an inactivated position to an activated position; a port septum positioned in the first sleeve proximate a port snap; and a means for preventing premature activation of the connector, wherein the first sleeve has a first attaching member, the first attaching member is a port adapter assembly, the first attaching member is adapted to connect to the first container, the port adapter assembly has the port snap connected to a membrane tube, the port snap is connected to the first sleeve, the membrane tube is adapted to be connected to a port tube of the first container, the first sleeve has a guide proximate a first end of the first sleeve, and the port septum is positioned between the guide and port snap.

2. The connector of claim 1 further comprising a piercing member positioned in the sleeves, the piercing member having a fluid pathway.

3. The connector of claim 2 wherein the fluid pathway is adapted to provide a fluid flow path between the first container and the second container when the device is in the activated position.

4. The connector of claim 2 wherein the fluid pathway is adapted to not be in fluid communication with the first container and the second container when the device is in the inactivated position.

5. The connector of claim 2 wherein the piercing member comprises a first piercing member connected to a second piercing member.

6. The connector of claim 5 wherein the first piercing member is a plastic spike.

7. The connector of claim 5 wherein the second piercing member is a metal cannula.

8. The connector of claim 2 wherein the piercing member has a hub.

9. The connector of claim 8 wherein the second sleeve has a ledge, the hub engaging the ledge when the sleeves are in the inactivated position.

10. The connector of claim 9 wherein the second sleeve has a projection, the hub positioned between the ledge and projection when the connector is in the inactivated position.

11. The connector of claim 8 wherein the second sleeve has a projection, the projection engaging the hub when the connector is in the inactivated position.

12. The connector of claim 8 wherein when the sleeves move from the inactivated position to the activated position, a second end of the sleeve contacts the hub moving the piercing member towards a second end of the second sleeve.

13. The connector of claim 12 wherein the second sleeve has a protuberance, the hub moving past the protuberance in the activated position, the protuberance preventing movement of the hub when the sleeves are moved back to the inactivated position to define a deactivated position.

14. The connector of claim 2 wherein the piercing member has a plurality of wings.

15. The connector of claim 2 wherein the piercing member comprises a plastic spike integral with a hub, and a metal cannula connected to the plastic spike.

16. The connector of claim 2 wherein the second sleeve has a protuberance, the protuberance engaging the piercing member when the connector is moved to a deactivated position.

17. The connector of claim 2 wherein the first sleeve has a first end and a second end, the first sleeve having a guide proximate the first end, the piercing member having a first end positioned proximate the guide.

18. The connector of claim 2 further comprising means for hermetically sealing the piercing member.

19. The connector of claim 1 wherein the first sleeve is positioned within the second sleeve.

20. The connector of claim 19 wherein the first sleeve has a first end and a second end, the first sleeve defining a groove proximate the second end, and a sealing member received by the groove and abutting an inner surface of the second sleeve providing a seal between the first sleeve and the second sleeve when the connector is in the inactivated position.

21. The connector of claim 20 wherein the second sleeve has a first section and a second section, the sealing member positioned at the first section.

22. The connector of claim 21 wherein the second section of the second sleeve has a larger diameter than a diameter of the first section, wherein when the sleeves move from the inactivated position to the activated position, the sealing member moves to the second section and does not provide a seal between the first sleeve and the second sleeve.

23. The connector of claim 19 wherein the first sleeve has a first end and a second end, the first sleeve having a stop surface at the second end, the second sleeve having a ledge wherein the stop surface engages the ledge in the inactivated position.

24. The connector of claim 1 further comprising a sealing member positioned between the first sleeve and the second sleeve.

25. The connector of claim 1 wherein the first attaching member is integral with the first sleeve.

26. The connector of claim 1 wherein the membrane tube has a membrane pierceable by the piercing member when the connector is in the activated position.

27. The connector of claim 1 wherein the membrane tube is adapted to be solvent bonded to the port tube of the first container.

28. The connector of claim 1 wherein the membrane tube is solvent bonded to the port snap.

29. The connector of claim 1 wherein the guide has a projection that indents the port septum.

30. The connector of claim 1 wherein the port snap has a finger that indents the port septum.

31. The connector of claim 1 wherein the first sleeve has a protrusion proximate a first end of the first sleeve, the port snap having flange, the port snap being snap fit into the first sleeve wherein the flange engages the protrusion.

32. The connector of claim 31 wherein the port snap is snap fit into the first sleeve within a low energy e-beam field.

33. The connector of claim 1 wherein the first attaching member is attached to the first sleeve within a low energy e-beam field.

34. The connector of claim 1 wherein the second sleeve has a first end and a second end, and further comprising a sealing member positioned proximate the second end of the second sleeve.

35. The connector of claim 1 wherein the second sleeve has a second attaching member, the second attaching member being adapted to connect to the second container.

36. The connector of claim 35 wherein the second attaching member is integral with the second sleeve.

37. The connector of claim 35 wherein the second attaching member is a gripper assembly.

38. The connector of claim 37 wherein the gripper assembly comprises a base, a finger assembly extending from the base, and an annular wall circumjacent the finger assembly.

39. The connector of claim 38 wherein the finger assembly comprises a plurality of fingers.

40. The connector of claim 39 wherein a finger has a tab.

41. The connector of claim 39 wherein a finger has a standing rib.

42. The connector of claim 38 further comprising a septum positioned between the base and the finger assembly.

43. The connector of claim 42 wherein the septum has rubber collar contacting the base.

44. The connector of claim 38 further comprising a seal material over the annular wall.

45. The connector of claim 1 further comprising a finger assembly connected to a second end of the second sleeve, the finger assembly adapted to connect to the second container.

46. The connector of claim 45 wherein the finger assembly is sized to conform to dimensions of the second container.

47. The connector of claim 1 further comprising a septum positioned proximate a second end of the second sleeve.

48. The connector of claim 1 wherein the second sleeve has first section and a second section defining an inner surface, the inner surface being tapered between the first section and the second section.

* * * * *